(12) United States Patent
Gong et al.

(10) Patent No.: US 9,174,944 B1
(45) Date of Patent: Nov. 3, 2015

(54) CRYSTALLINE LOPINAVIR/SURFACTANT ADDUCTS

(75) Inventors: Yuchuan Gong, Waukegan, IL (US); Geoff G. Zhang, Vernon Hills, IL (US); Matthias Degenhardt, Ludwigshafen (DE); Markus Maegerlein, Mannheim (DE)

(73) Assignee: ABBVIE INC., North Chicago, IL (US)

( * ) Notice: Subject to any disclaimer, the term of this patent is extended or adjusted under 35 U.S.C. 154(b) by 336 days.

(21) Appl. No.: 13/328,121

(22) Filed: Dec. 16, 2011

Related U.S. Application Data

(60) Provisional application No. 61/424,364, filed on Dec. 17, 2010.

(51) Int. Cl.
*C07D 239/10* (2006.01)
*A61K 31/513* (2006.01)

(52) U.S. Cl.
CPC ............ *C07D 239/10* (2013.01); *A61K 31/513* (2013.01)

(58) Field of Classification Search
CPC .......................... C07D 239/10; A61K 31/513
USPC .......................................... 544/318; 514/274
See application file for complete search history.

(56) References Cited

U.S. PATENT DOCUMENTS

| 5,914,332 | A | 6/1999 | Sham et al. |
| 6,232,333 | B1 | 5/2001 | Lipari et al. |
| 6,608,198 | B2 | 8/2003 | Chemburkar et al. |
| 6,864,369 | B2 | 3/2005 | Dickman et al. |
| 7,141,593 | B1 | 11/2006 | Alani et al. |
| 2005/0084529 | A1 | 4/2005 | Rosenberg et al. |

OTHER PUBLICATIONS

Brown J.H., et al., "Muscarinic Receptor Agonists and Antagonists" in: The Pharmacological Basis of Therapeutics, 10th Edition, Goodman & Gilman. ed., McGraw-Hill Publications, 2001, Chap. 7, pp. 155-173.
Gennaro A.R., ed., Remington's Pharmaceutical Sciences, 18th Edition, Mack Publishing Company, 1990, Table of Contents.

*Primary Examiner* — Deepak Rao
(74) *Attorney, Agent, or Firm* — J.A. Lindeman & Co., PLLC

(57) ABSTRACT

This invention relates to novel crystalline lopinavir/surfactant adducts, methods for their preparation, therapeutic uses of those crystalline lopinavir/surfactant adducts, and pharmaceutical compositions containing them or made from them.

9 Claims, 46 Drawing Sheets

CRYSTALLINE LOPINAVIR/SURFACTANT ADDUCTS

FIELD OF THE INVENTION

This invention relates to novel crystalline lopinavir/surfactant adducts, methods for their preparation, therapeutic uses of those crystalline lopinavir/surfactant adducts, and pharmaceutical compositions containing them or made from them.

BACKGROUND

Lopinavir, (2S,3S,5S)-21-2,6-dimethylphenoxyacetyl)-amino-3-hydroxy-5-(2-(1-tetrahydropyrimid-2-onyl)-3-methylbutanoyl)amino-1,6-diphenylhexane, has the following chemical structure:

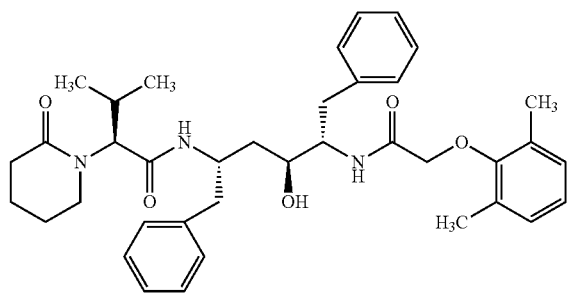 [SMILES: Cc1cccc(C)c1OCC(=O)N[C@@H](Cc1ccccc1)[C@@H](O)C[C@H](Cc1ccccc1)NC(=O)[C@H](C(C)C)N1CCCCC1=O]

Lopinavir is known to have utility for the inhibition of HIV protease, the inhibition of HIV infection, and treatment of HIV infection.

Lopinavir and processes for its preparation are disclosed in U.S. Pat. No. 5,914,332, issued Jun. 22, 1999, which is hereby incorporated herein by reference.

Crystalline forms of lopinavir and processes for their preparation are disclosed in U.S. Pat. No. 6,864,369, issued Mar. 8, 2005, which is hereby incorporated by reference.

Pharmaceutical compositions containing lopinavir or a pharmaceutically acceptable salt thereof are disclosed in U.S. Pat. No. 5,914,332, issued Jun. 22, 1999; U.S. Pat. No. 6,232,333, issued May 15, 2001; U.S. Pat. No. 7,141,593, issued Nov. 28, 2006; and U.S. Patent Application Publication No. 2005/0084529, published Apr. 21, 2005, all of which are hereby incorporated herein by reference.

SUMMARY OF THE INVENTION

This invention relates to novel crystalline lopinavir/surfactant adducts, which in many aspects have improved physiochemical and/or pharmaceutical properties over lopanivir itself.

In one aspect, a crystalline lopinavir/surfactant adduct of the invention comprises a crystal structure including lopinavir and a surfactant. A crystalline lopinavir/surfactant adduct of the invention may also comprise a crystal structure which includes lopinavir and two or more different surfactants.

The surfactant(s) in a crystalline lopinavir/surfactant adduct of the invention can be selected, for example and without limitation, from VitE TPGS, a polysorbate (e.g., Tween 80, Tween 65, Tween 20), a sobitan fatty acid ester (e.g., Span 80, Span 40, Span 20), a polyoxyethylene ester (e.g., Solutol HS15), a poloxamer or a copolymer of ethylene oxide and propylene oxide (e.g., Pluronic F68), Plurol oleique, a fatty acid (e.g., Oleic acid), a propylene glycol laurate (e.g., Lauroglycol Type 1, Lauroglycol FCC), a polyoxyethylene hydrogenated castor oil (e.g., Cremophor RH40), a polyethoxylated castor oil (e.g., Cremophor EL), a propylene glycol monocaprylate (e.g., Capryol 90), or a combination thereof. For instance, a crystalline lopinavir/surfactant adduct of the invention can include a surfactant selected from VitE TPGS, Tween 80, Tween 65, Tween 20, Span 80, Span 40, Span 20, Solutol HS15, Pluronic F68, Plurol oleique, Oleic acid, Lauroglycol Type 1, Lauroglycol FCC, Cremophor RH40, Cremophor EL, Capryol 90, or a combination thereof.

Preferably, a crystalline lopinavir/surfactant adduct of the invention comprises a crystal structure including lopinavir and a pharmaceutically acceptable surfactant. In one example, a crystalline lopinavir/surfactant adduct of the invention comprises a crystal structure which includes lopinavir and VitE TPGS. In another example, a crystalline lopinavir/surfactant adduct of the invention comprises a crystal structure which includes lopinavir and a sobitan fatty acid ester such as Span 20.

A crystalline lopinavir/surfactant adduct of the invention preferably is characterized by an XRPD pattern having peaks at 4.8, 7.3, 8.8, 9.7, 10.3, 12.2, 12.8, 14.7, 16.4, 17.6, 18.6, 20.0, 21.9, 22.5, and 23.0°2θ±0.2°2θ. Also preferably, a crystalline lopinavir/surfactant adduct of the invention is characterized by an IR spectrum having a peak at 1730 cm$^{-1}$. More preferably, a crystalline lopinavir/surfactant adduct of the invention is characterized by a Raman spectrum having peaks at 3398, 3066, 3042, 2925, 2968, 1660, 1643, 1606, 1585, 1446, 1381, 1346, 1267, 1238, 1209, 1033, 1004, 958, 883, 791, 754, 697, 622, and 532 cm$^{-1}$±1 cm$^{-1}$.

In another aspect, the invention features relatively pure crystalline lopinavir/surfactant adducts. In one embodiment, a relatively pure crystalline lopinavir/surfactant adduct of the invention is at least 50% pure (e.g., the relatively pure crystalline lopinavir/surfactant adduct contains less than 50% other lopinavir forms). In another embodiment, a relatively pure crystalline lopinavir/surfactant adduct of the invention is at least 60% pure (e.g., the relatively pure crystalline lopinavir/surfactant adduct contains less than 40% other lopinavir forms). In another embodiment, a relatively pure crystalline lopinavir/surfactant adduct of the invention is at least 70% pure (e.g., the relatively pure crystalline lopinavir/surfactant adduct contains less than 30% other lopinavir forms). In another embodiment, a relatively pure crystalline lopinavir/surfactant adduct of the invention is at least 80% pure (e.g., the relatively pure crystalline lopinavir/surfactant adduct contains less than 20% other lopinavir forms). In another embodiment, a relatively pure crystalline lopinavir/surfactant adduct of the invention is at least 90% pure (e.g., the relatively pure crystalline lopinavir/surfactant adduct contains less than 10% other lopinavir forms). In still another embodiment, a relatively pure crystalline lopinavir/surfactant adduct of the invention is at least 95% pure (e.g., the relatively pure crystalline lopinavir/surfactant adduct contains less than 5% other lopinavir forms).

In yet another aspect, the invention features substantially pure crystalline lopinavir/surfactant adducts. In one embodiment, a substantially pure crystalline lopinavir/surfactant adduct contains less than 5% impurity (e.g., less than 5% other lopinavir forms). In another embodiment, a substantially pure crystalline lopinavir/surfactant adduct contains less than 3% impurity (e.g., less than 3% other lopinavir forms). In another embodiment, a substantially pure crystalline lopinavir/surfactant adduct contains less than 1% impurity (e.g., less than 1% other lopinavir forms).

In still another aspect, the invention features pharmaceutical compositions comprising an effective amount of a crystalline lopinavir/surfactant adduct of the invention. In one embodiment, at least 50% of lopinavir in a pharmaceutical composition of the invention is in the form of a crystalline lopinavir/surfactant adduct of the invention. In another embodiment, at least 60% of lopinavir in a pharmaceutical composition of the invention is in the form of a crystalline lopinavir/surfactant adduct of the invention. In another embodiment, at least 70% of lopinavir in a pharmaceutical composition of the invention is in the form of a crystalline lopinavir/surfactant adduct of the invention. In another embodiment, at least 80% of lopinavir in a pharmaceutical composition of the invention is in the form of a crystalline lopinavir/surfactant adduct of the invention. In another embodiment, at least 90% of lopinavir in a pharmaceutical composition of the invention is in the form of a crystalline lopinavir/surfactant adduct of the invention. In another embodiment, at least 95% of lopinavir in a pharmaceutical composition of the invention is in the form of a crystalline lopinavir/surfactant adduct of the invention. In yet another embodiment, at least 99% of lopinavir in a pharmaceutical composition of the invention is in the form of a crystalline lopinavir/surfactant adduct of the invention.

The present invention also features processes of making pharmaceutical compositions comprising lopinavir. In one embodiment, the process comprises mixing a crystalline lopinavir/surfactant adduct of the invention with one or more excipients. The mixing can be, for example and without limitation, a simple mechanical mixing, a melt extrusion-based mixing, or a solvent-based mixing.

In another embodiment, the process comprises dissolving a crystalline lopinavir/surfactant adduct of the invention. In one example, the crystalline lopinavir/surfactant adduct of the invention is dissolved in a molten water-soluble polymer. The melt that comprises the crystalline lopinavir/surfactant adduct and the water-soluble polymer can be subsequently cooled or solidified. In another example, the crystalline lopinavir/surfactant adduct of the invention is dissolved in a volatile solvent. The solvent can be subsequently removed from the solution, for example, through drying (e.g., spray drying, freeze drying, or other evaporation methods), to convert the solution into a powder.

The present invention also features methods of treating HIV infection. The methods comprise administering to a patient in need thereof an effective amount of a crystalline lopinavir/surfactant adduct of the invention.

In addition, the present invention features processes for preparation of a crystalline lopinavir/surfactant adduct of the invention. In one embodiment, the processes comprise grinding a mixture of amorphous lopinavir and a surfactant under conditions sufficient to obtain a crystalline lopinavir/surfactant adduct.

In the following description, various aspects and embodiments of the invention will become evident. In its broadest sense, the invention could be practiced without having one or more features of these aspects and embodiments. Further, these aspects and embodiments are exemplary. Additional objects and advantages of the invention will be set forth in part in the description which follows, and in part will be obvious from the description.

BRIEF DESCRIPTION OF THE DRAWINGS

The following figures, which are described below and which are incorporated in and constitute a part of the specification, illustrate exemplary embodiments according to the invention and are not to be considered limiting of the scope of the invention, for the invention may admit to other equally effective embodiments. The figures are not necessarily to scale, and certain features and certain views of the figures may be shown exaggerated in scale or in schematic in the interest of clarity and conciseness

DETAILED DESCRIPTION

Figure 1:
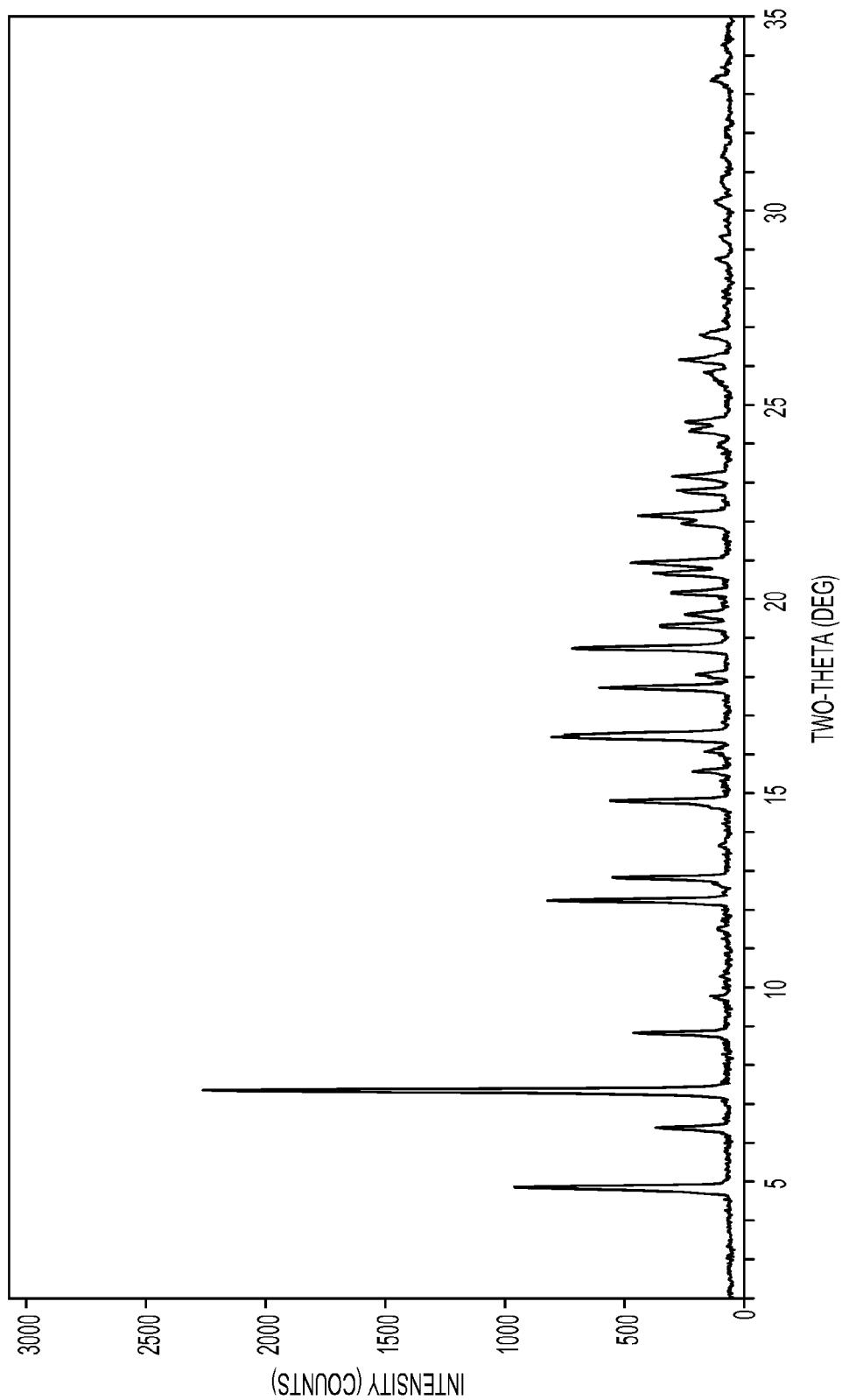
FIG. 1 shows an XRPD pattern of a Type III lopinavir crystal solvate (lopinavir/EtOAc solvate).
Figure 2:
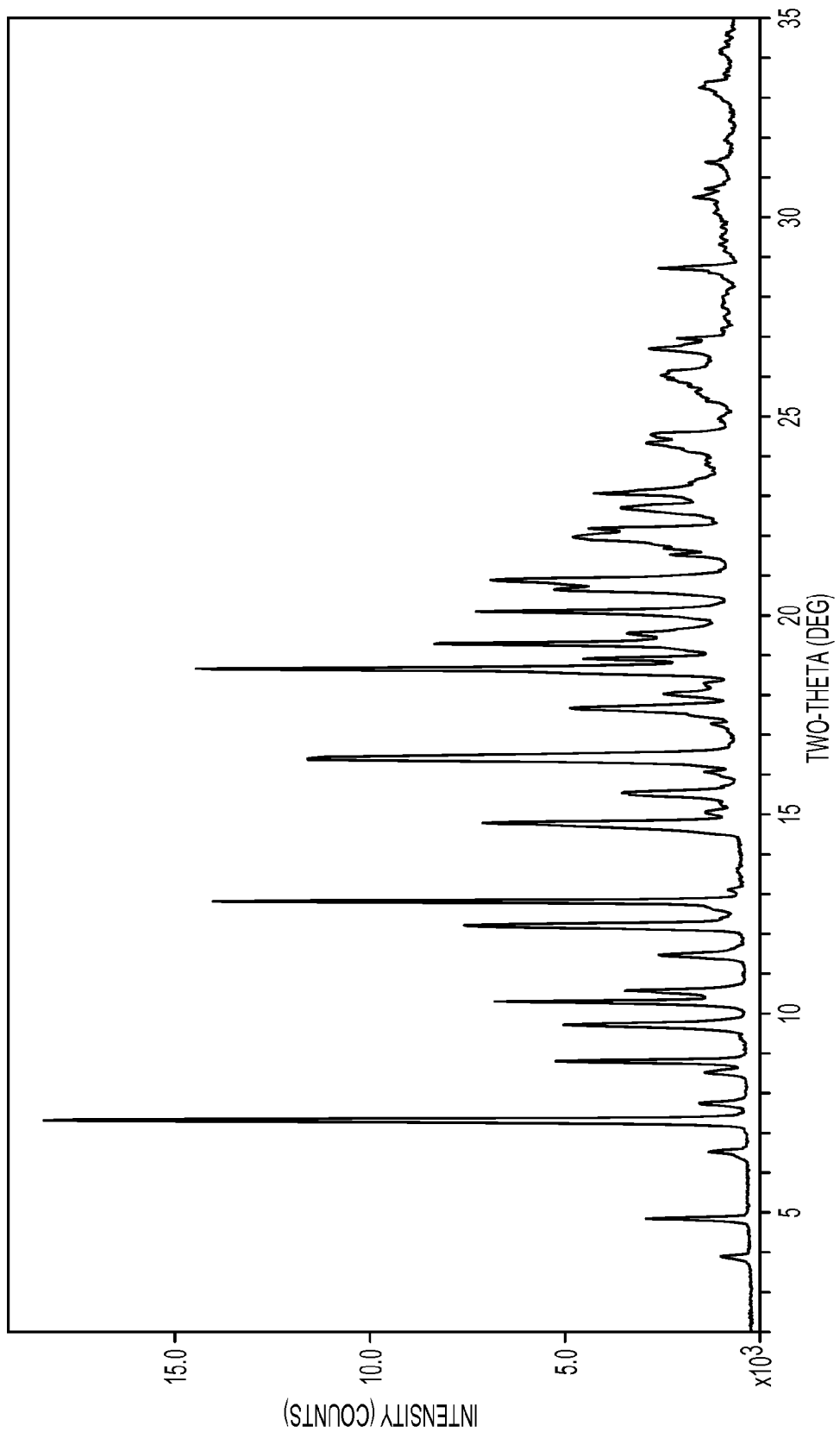
FIG. 2 shows an XRPD pattern of a crystalline adduct of lopinavir/VitE TPGS.
Figure 3:
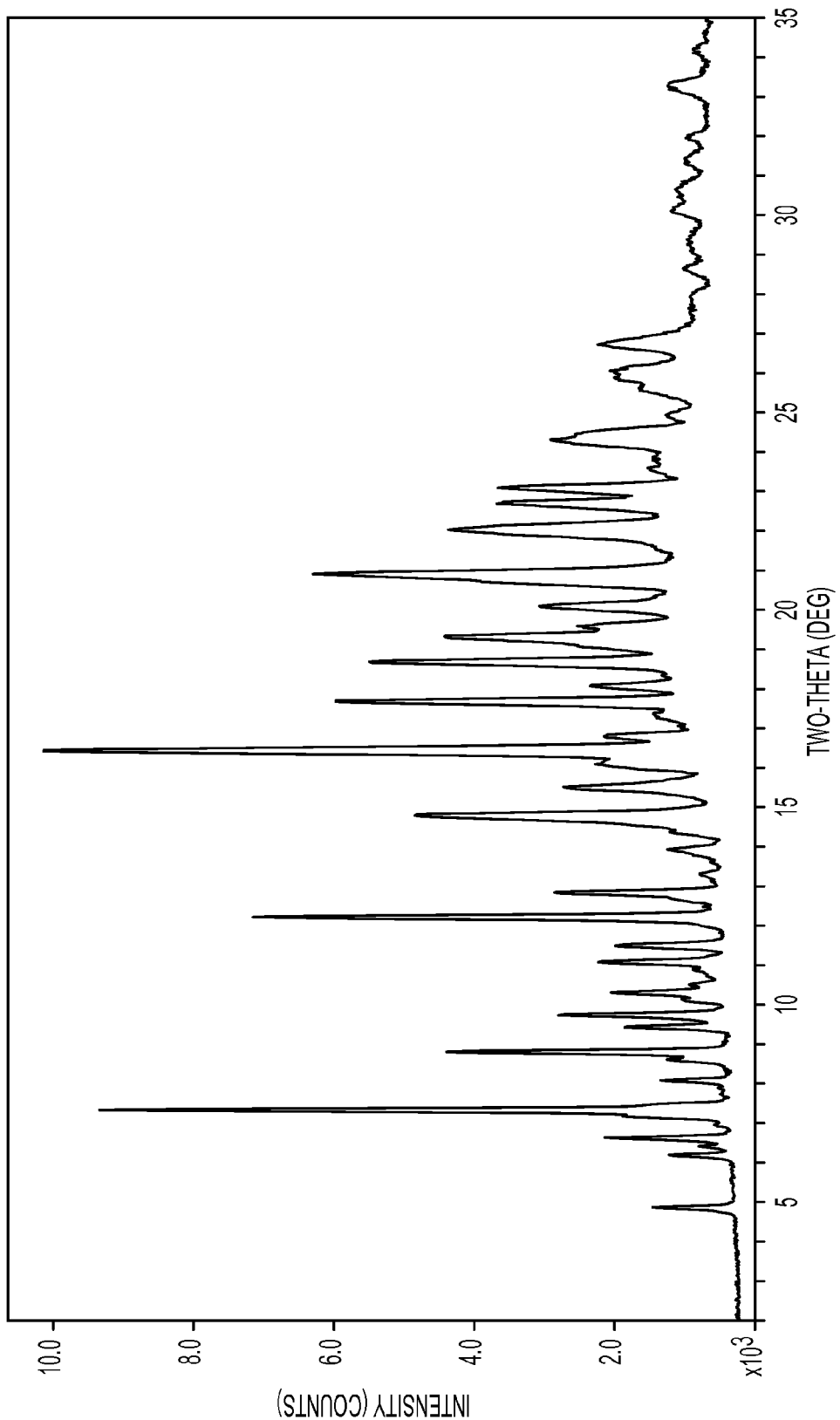
FIG. 3 shows an XRPD pattern of a crystalline adduct of lopinavir/Tween 80.
Figure 4:
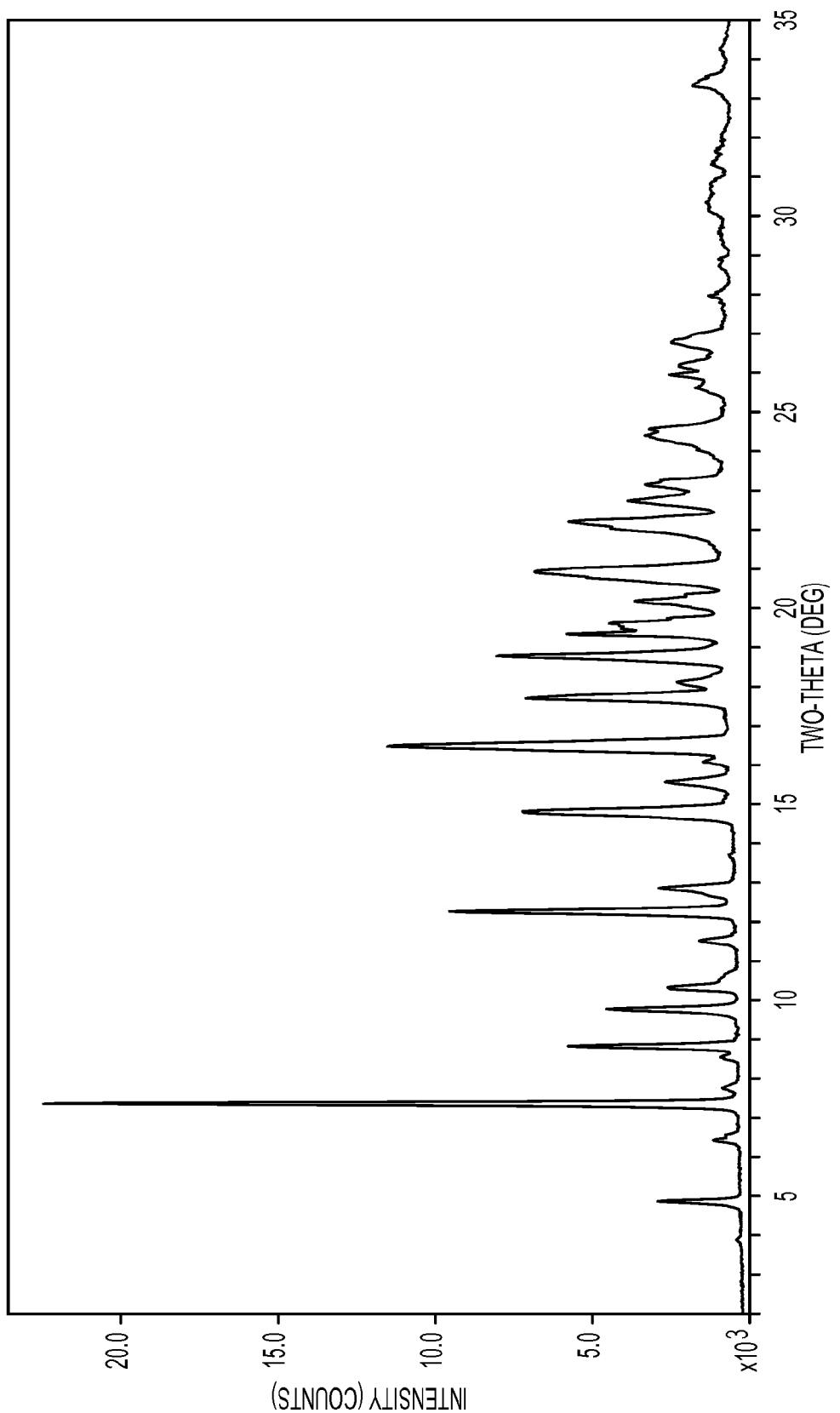
FIG. 4 shows an XRPD pattern of a crystalline adduct of lopinavir/Tween 65.
Figure 5:
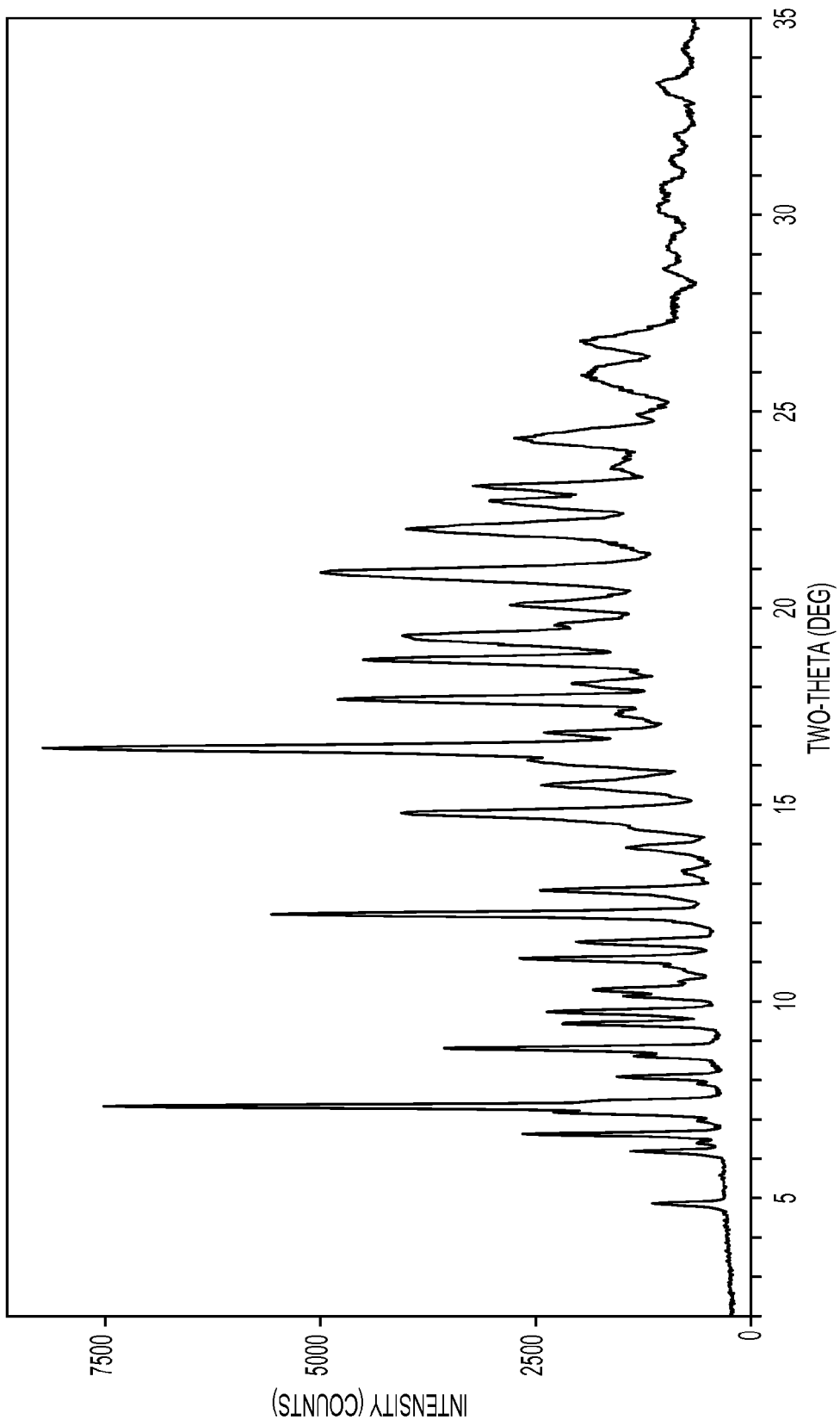
FIG. 5 shows an XRPD pattern of a crystalline adduct of lopinavir/Tween 20.
Figure 6:
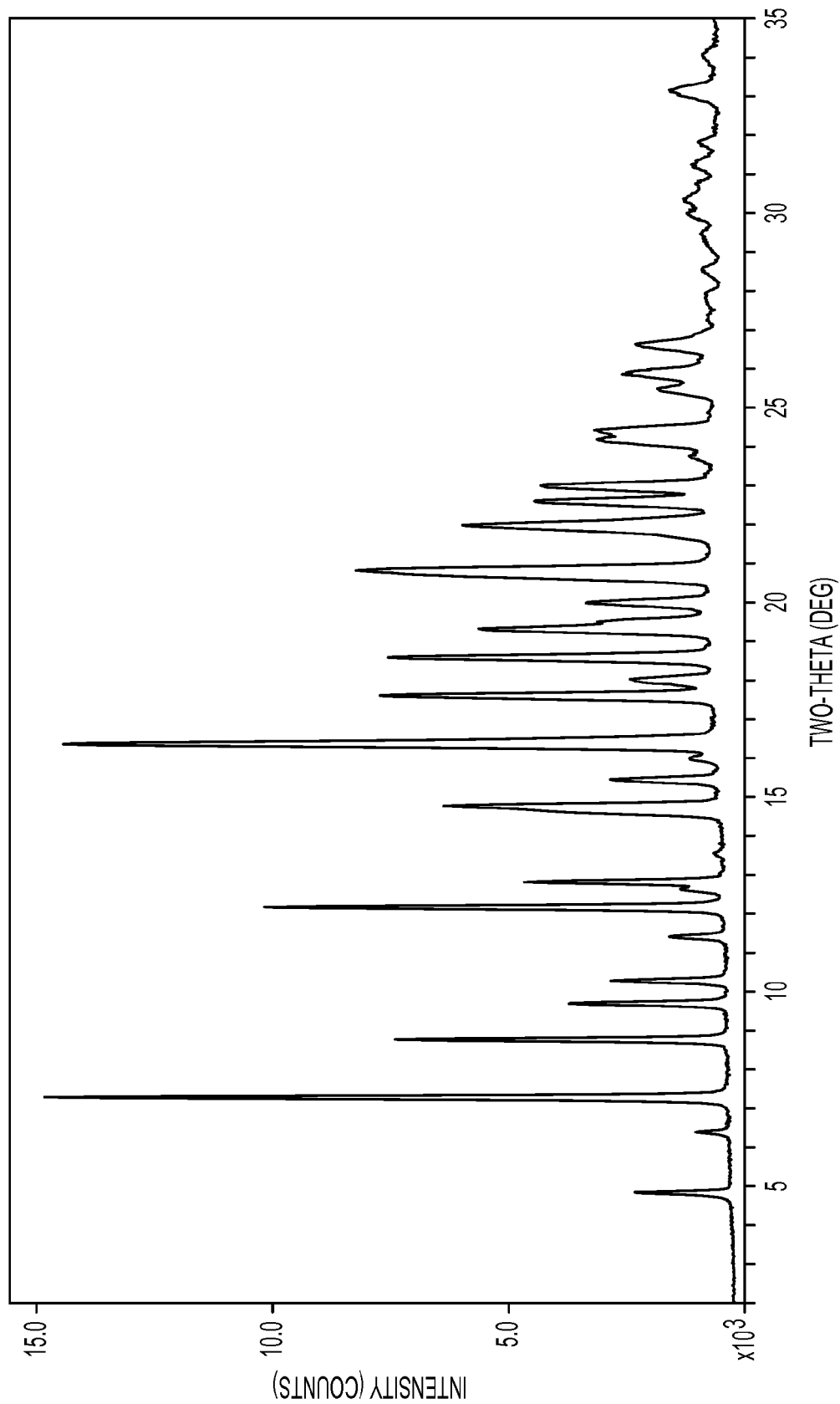
FIG. 6 shows an XRPD pattern of a crystalline adduct of lopinavir/Span 80.
Figure 7:
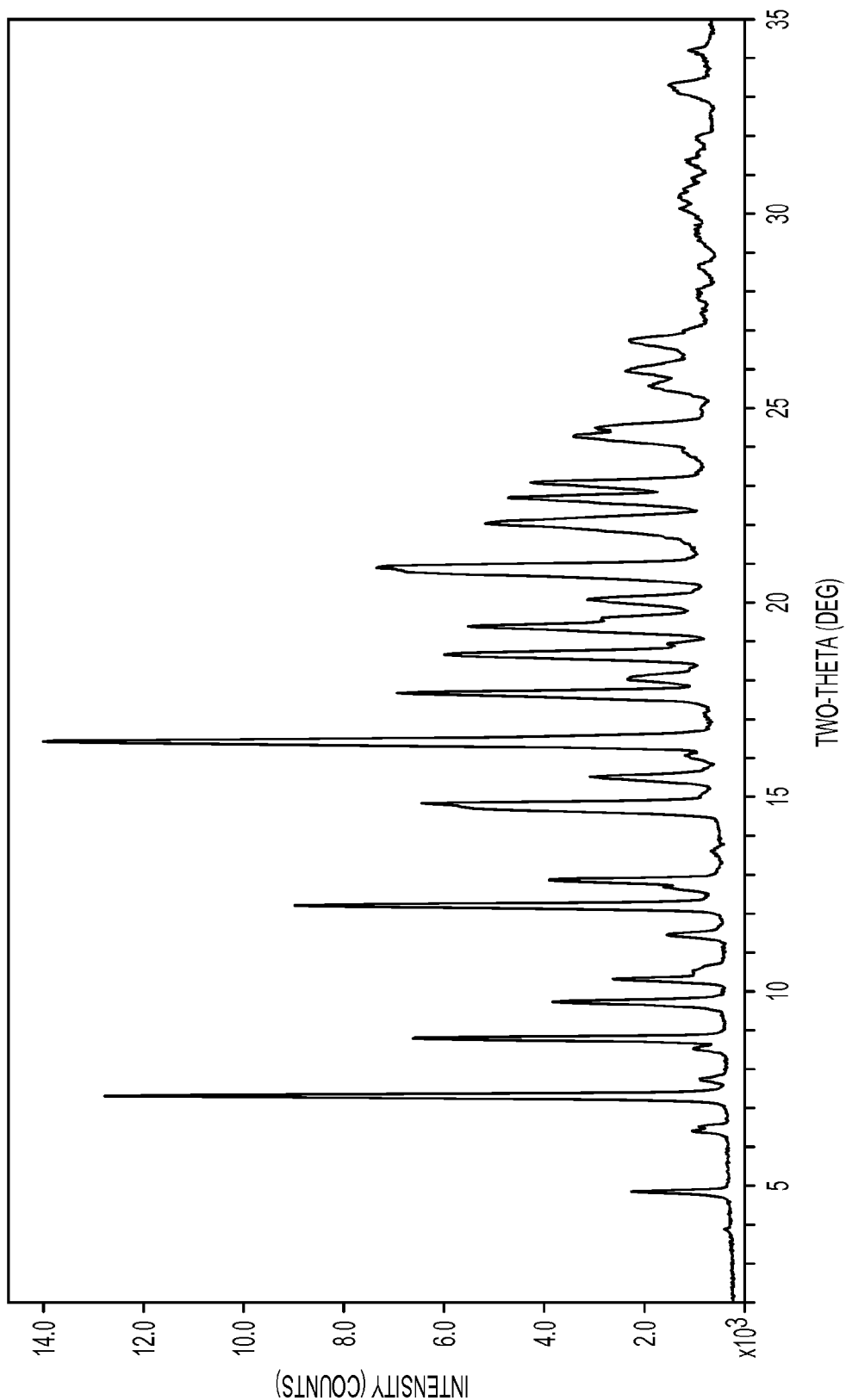
FIG. 7 shows an XRPD pattern of a crystalline adduct of lopinavir/Span 40.
Figure 8:
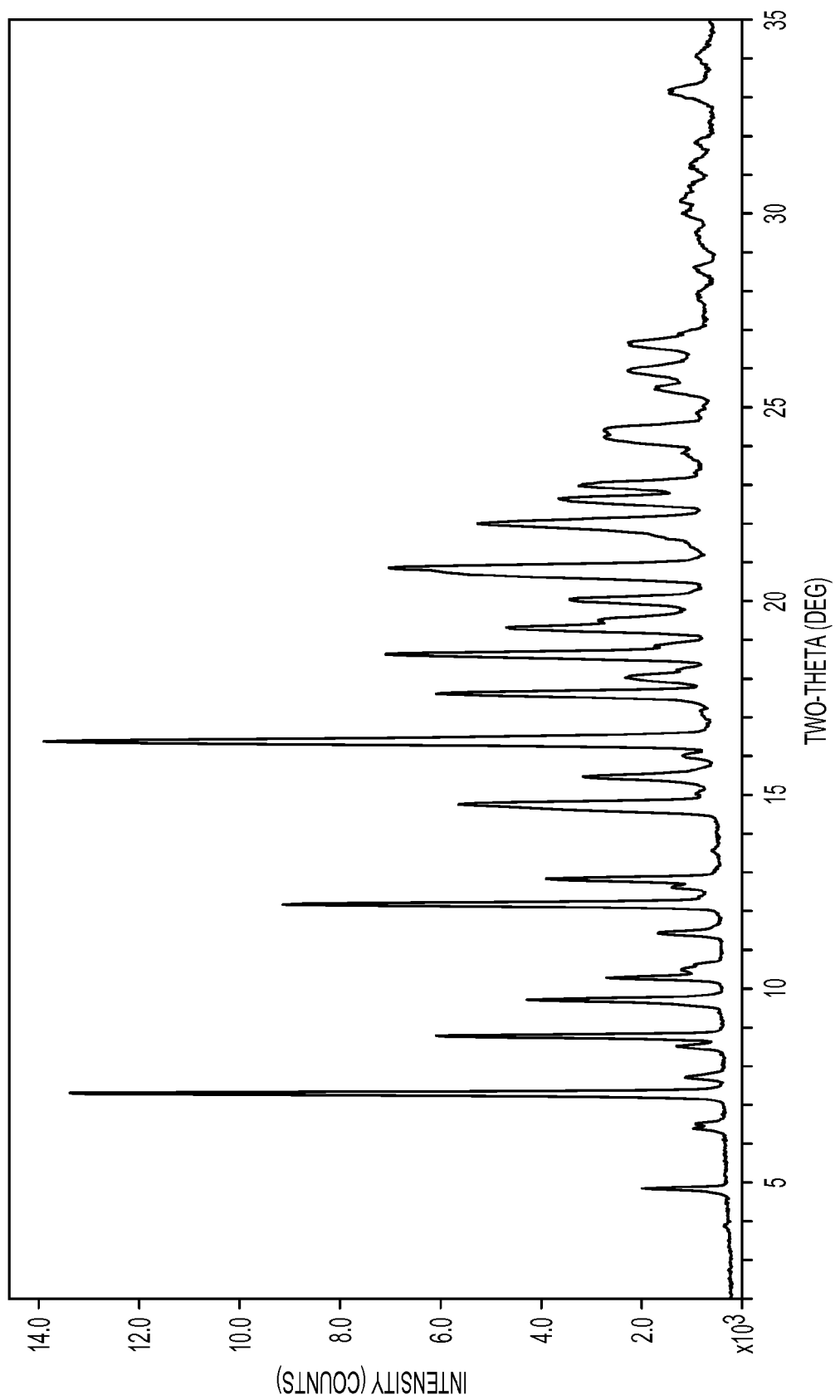
FIG. 8 shows an XRPD pattern of a crystalline adduct of lopinavir/Span 20.
Figure 9:
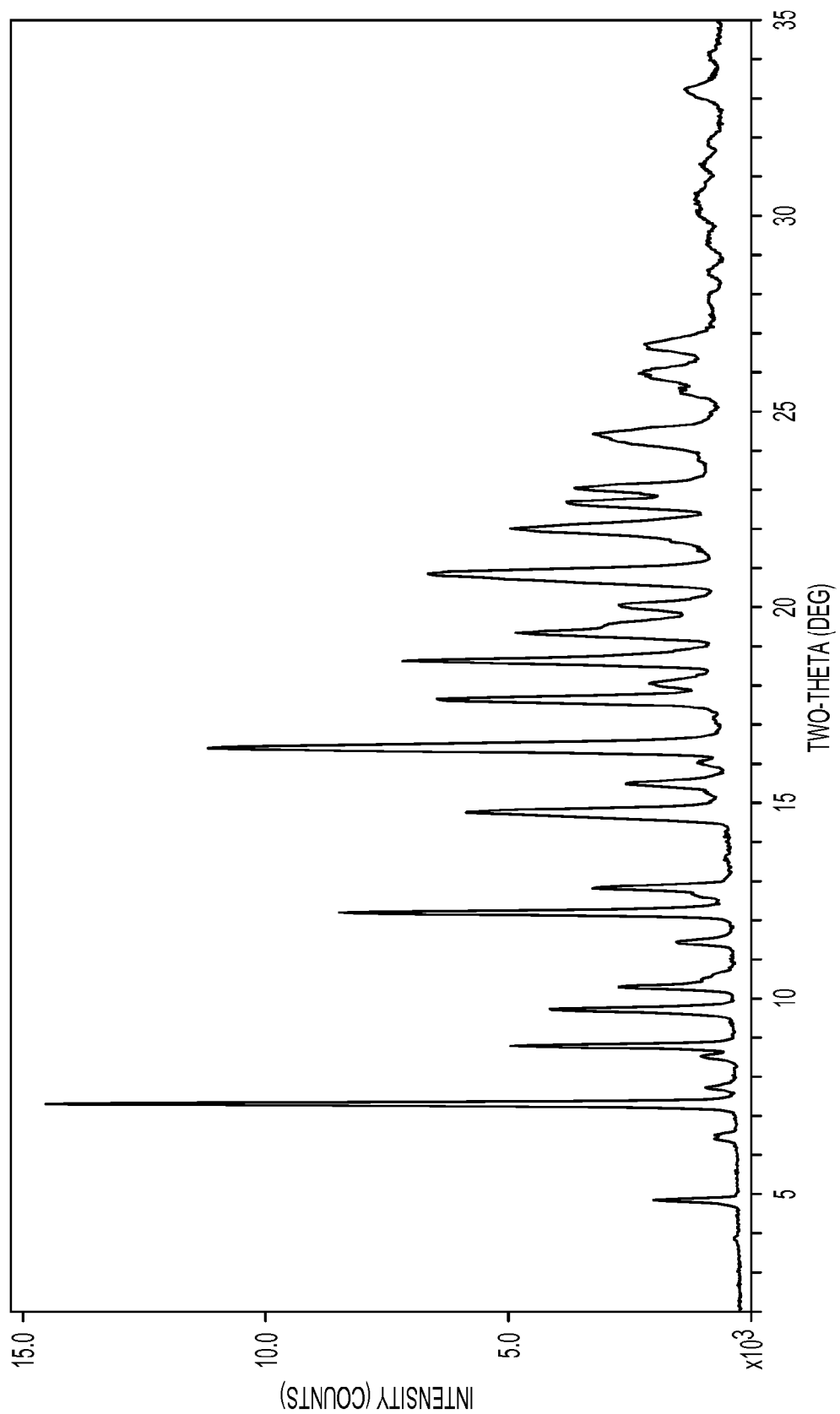
FIG. 9 shows an XRPD pattern of a crystalline adduct of lopinavir/Solutol HS15.
Figure 10:
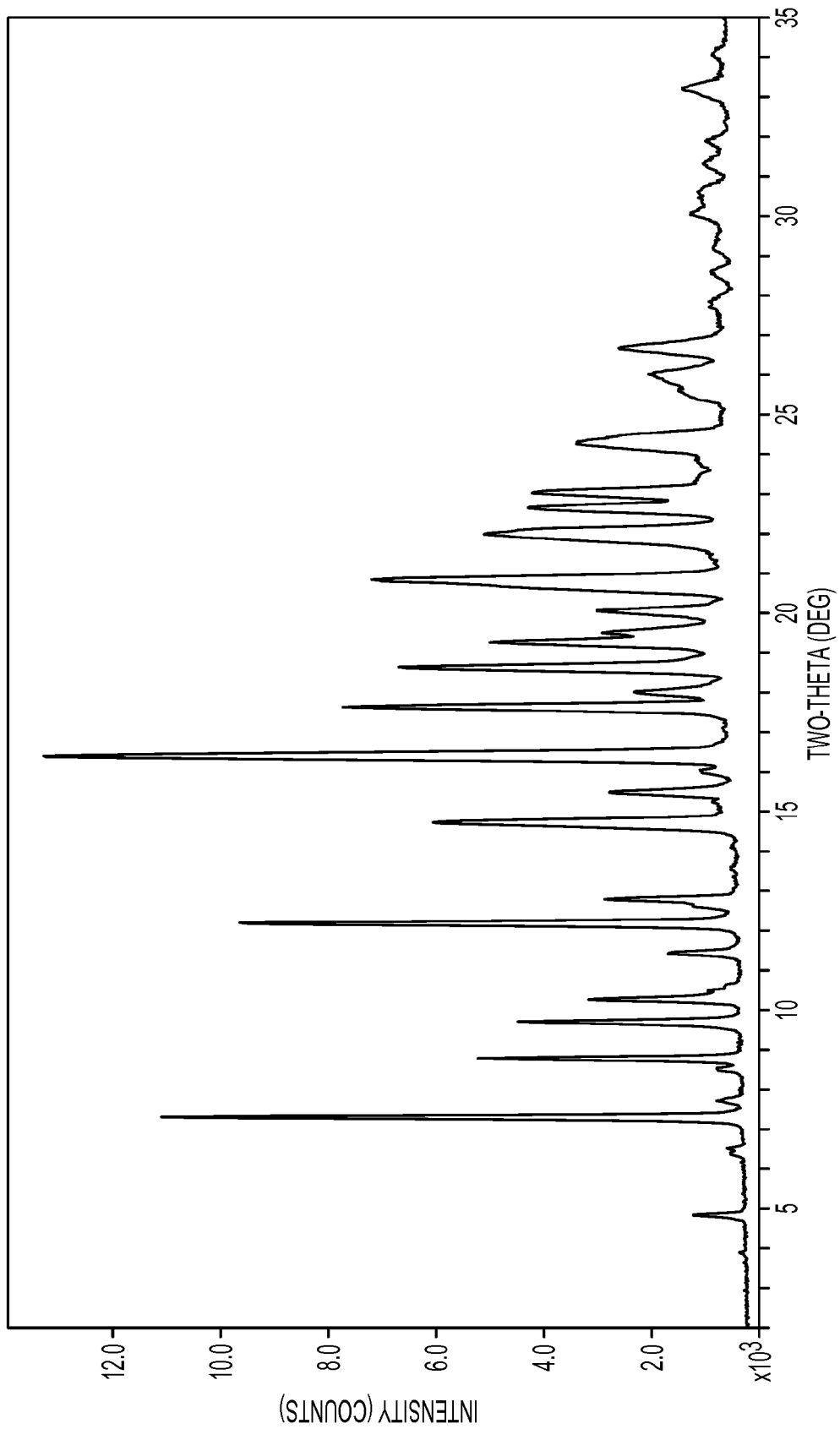
FIG. 10 shows an XRPD pattern of a crystalline adduct of lopinavir/Pluronic F68.

Disclosed herein are novel crystalline adducts of lopinavir and surfactants, processes for making the crystalline adducts, therapeutic uses of these crystalline adducts, and compositions containing the crystalline adducts or made from them.

Type III crystalline forms of lopinavir are described in U.S. Pat. No. 6,864,369. Type III forms are believed to have a crystal structure in which the molecules of lopinavir are hydrogen bonded in sheets. The sheets of hydrogen bonded lopinavir molecules are wrinkled, producing channels that are occupied by varying amounts of solvent molecules. It was believed that these channels typically have restricted space, and only small solvent molecules are expected to fit into these channels.

It was entirely unexpected that large surfactant molecules can also fit into the channels within lopinavir Type III crystalline lattice. Conventionally, to form cocrystals with drug molecules, foreign molecules either form strong interaction with drug molecules, or have a small molecular size to fill the voids in the crystal lattice. Many surfactants are not expected to have strong interaction with lopinavir. In addition, many surfactants have a large molecular size and it would be difficult for them to fill in the voids in the crystal lattice. Therefore, it was counterintuitive that surfactants, which typically have a much larger size than small organic solvents, would form crystalline adducts with lopinavir. However, as disclosed herein and without limiting the invention to any particular theory, lopinavir formed crystalline adducts with various surfactants despite the larger size of the surfactant molecules and lack of strong intra-molecular bonding.

Crystalline Lopinavir/Surfactant Adducts

In one embodiment, the invention relates to crystalline lopinavir/surfactant adducts, which contain at least one surfactant. Preferably, the surfactant is a non-ionic surfactant. Also preferably, the surfactant has a molecular weight of at least 100 grams per mole. More preferably, the surfactant has a molecular weight of at least 200 grams per mole, or at least 300 grams per mole. The following non-limiting surfactants may be present in the crystalline lopinavir/surfactant adduct: VitE TPGS, a polysorbate (e.g., Tween 80, Tween 65, Tween 20), a sobitan fatty acid ester (e.g., Span 80, Span 40, Span 20), a polyoxyethylene ester (e.g., Solutol HS15), a poloxamer or a copolymer of ethylene oxide and propylene oxide (e.g., Pluronic F68), Plurol oleique, a fatty acid (e.g., Oleic acid), a propylene glycol laurate (e.g., Lauroglycol Type 1, Lauroglycol FCC), a polyoxyethylene hydrogenated castor oil (e.g., Cremophor RH40), a polyethoxylated castor oil (e.g., Cremophor EL), and a propylene glycol monocaprylate (e.g., Capryol 90).

In another embodiment, the crystalline lopinavir/surfactant adduct is characterized by an XRPD pattern having peaks at 4.8, 7.3, 8.8, 9.7, 10.3, 12.2, 12.8, 14.7, 16.4, 17.6, 18.6, 20.0, 21.9, 22.5, and 23.0°2θ±0.2°2θ or a subset of these peaks.

In one embodiment, the at least one surfactant of the crystalline lopinavir/surfactant adduct characterized by an XRPD pattern having peaks at 4.8, 7.3, 8.8, 9.7, 10.3, 12.2, 12.8, 14.7, 16.4, 17.6, 18.6, 20.0, 21.9, 22.5, and 23.0°2θ±0.2°2θ (or a subset of these peaks) is selected from, for example, VitE TPGS, Tween 80, Tween 65, Tween 20, Span 80, Span 40, Span 20, Solutol HS15, Pluronic F68, Plurol oleique, Oleic acid, Lauroglycol Type 1, Lauroglycol FCC, Cremophor RH40, Cremophor EL, and Capryol 90.

In one embodiment, the crystalline lopinavir/surfactant adduct is characterized by an IR spectrum having a peak at 1730 $cm^{-1}$.

In one embodiment, the crystalline lopinavir/surfactant adduct is characterized by Raman spectrum having peaks at 3398, 3066, 3042, 2925, 2968, 1660, 1643, 1606, 1585, 1446, 1381, 1346, 1267, 1238, 1209, 1033, 1004, 958, 883, 791, 754, 697, 622, and 532 $cm^{-1}$±1 $cm^{-1}$ or a subset of these peaks.

In one embodiment, the at least one surfactant of the crystalline lopinavir/surfactant adduct characterized by Raman spectrum having peaks at 3398, 3066, 3042, 2925, 2968, 1660, 1643, 1606, 1585, 1446, 1381, 1346, 1267, 1238, 1209, 1033, 1004, 958, 883, 791, 754, 697, 622, and 532 $cm^{-1}$±1 $cm^{-1}$ (or a subset of these peaks) is selected from, for example, VitE TPGS, Tween 80, Tween 65, Tween 20, Span 80, Span 40, Span 20, Solutol HS15, Pluronic F68, Plurol oleique, Oleic acid, Lauroglycol Type 1, Lauroglycol FCC, Cremophor RH40, Cremophor EL, and Capryol 90.

In one embodiment, the crystalline lopinavir/surfactant adduct is substantially pure. As used herein, the term "substantially pure" means a purity that is greater than about 95 weight percent pure, i.e., it contains less than about five weight percent, such as, for example, less than about one, two, three, or four weight percent of an impurity or impurities. In a preferred embodiment, the crystalline lopinavir/surfactant adduct is substantially pure, relative to other forms of lopinavir, including amorphous, solvated forms, non-solvated, and desolvated forms.

The amount of surfactant present in the crystalline lopinavir/surfactant adducts may vary depending on the surfactant used. For example, the crystalline lopinavir/surfactant adducts may contain at least 5% (weight) of surfactant, e.g., about 5-12% (weight) or about 15-25% (mole) of surfactant. For example, in one embodiment, the crystalline lopinavir/lauroglycol adduct contains about 8.5-10.5% (weight) and about 18-22% (mole) of lauroglycol.

Processes for the Preparation of the Crystalline Lopinavir/Surfactant Adducts

In one embodiment, the invention relates to a process for the preparation of the crystalline lopinavir/surfactant adduct, comprising: co-extruding a melt comprising primarily amorphous lopinavir and a surfactant to form a lopinavir-surfactant extrudate, and storing the lopinavir/surfactant extrudate under proper stress conditions sufficient to obtain a crystalline lopinavir/surfactant adduct.

In another embodiment, the crystalline lopanivir/surfactant adduct is prepared by grinding a mixture of amorphous lopanivir and surfactant or by crystallizing from neat surfactant solutions under conditions sufficient to obtain a crystalline lopinavir/surfactant adduct.

The examples discussed below further illustrate the preparation of the novel crystalline lopinavir/surfactant adducts of the invention.

Therapeutic Uses of the Crystalline Lopinavir/Surfactant Adducts

The invention further relates to the therapeutic use of at least one crystalline lopinavir/surfactant adduct of the invention to inhibit HIV protease, inhibit HIV infection, and/or treat HIV infection. Accordingly, the invention relates to method of inhibiting HIV protease, inhibiting HIV infection, and/or treating HIV infection comprising the step of administering to a patient in need thereof a therapeutically effective amount of at least one crystalline lopinavir/surfactant adduct of the invention or of a therapeutic composition containing at least one crystalline lopinavir/surfactant adduct.

Additionally, the at least one crystalline lopinavir/surfactant adduct disclosed herein may also be used in a method of treatment of a warm-blooded animal such as, for example, man, by therapy. For example, the at least one crystalline lopinavir/surfactant adduct according to the invention may be useful in a method of inhibiting HIV protease, inhibiting HIV infection, and/or treating HIV infection.

Moreover, the at least one crystalline lopinavir/surfactant adduct according to the invention may be used in the method of treating a human suffering from HIV infection. The use of the at least one crystalline lopinavir/surfactant adduct in any of the methods of treating a human described above also form aspects of this invention The treatment defined herein may be applied as a sole therapy or may involve, in addition to the at least one crystalline lopinavir/surfactant adduct of the invention, combination with at least one reverse transcriptase inhibitors, and/or at least one other HIV protease inhibitors, such as, for example, ritonavir. The present invention also features a pharmaceutical composition comprising (1) a lopinavir/surfactant adduct of the invention and (2) ritonavir, cobicistat (GS 9350), or another pharmacokinetics enhancer.

Such joint treatment may be achieved by way of the simultaneous, sequential, or separate dosing of the individual components of the treatment. Such combination products may employ at least one compound of this invention within the dosage range described herein and the other at least one pharmaceutically-active agent within its approved dosage range. Combination products may be formulated into a single dosage form.

Pharmaceutical Compositions Containing Crystalline Lopinavir/Surfactant Adducts

The invention also relates to pharmaceutical compositions comprising a therapeutically effective amount of at least one crystalline lopinavir/surfactant adduct according to the invention and, optionally, a pharmaceutically acceptable carrier (also known as a pharmaceutically acceptable excipient). As mentioned above, these pharmaceutical compositions are therapeutically useful for inhibiting HIV protease, inhibiting HIV infection, and treating HIV infection.

A pharmaceutical composition of the invention may be in any pharmaceutical form which contains at least one crystalline lopinavir/surfactant adduct according to the invention. The pharmaceutical composition may be, for example, a tablet, capsule, liquid suspension, injectable, topical, or transdermal. The pharmaceutical compositions generally contain, for example, about 1% to about 99% by weight of at least one crystalline lopinavir/surfactant adduct of the invention and, for example, 99% to 1% by weight of at least one suitable pharmaceutical excipient. In one embodiment, the composition may be between about 5% and about 75% by weight of at least one crystalline lopinavir/surfactant adduct of the invention with the rest being at least one suitable pharmaceutical excipient or at least one other adjuvant, as discussed below.

A "therapeutically effective amount" of at least one crystalline lopinavir/surfactant adduct according to the invention is that which correlates to about 0.1-about 500 mg of lopinavir itself, such as, for example, about 10-about 200 mg of lopinavir itself, further such as, for example, about 80-about 100 mg of lopinavir itself. The actual amount required for treatment of any particular patient may depend upon a variety of factors including, for example, the disease being treated and its severity; the specific pharmaceutical composition employed; the age, body weight, general health, sex and diet of the patient; the mode of administration; the time of administration; the route of administration; and the rate of excretion of lopinavir; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. The at least one crystalline lopinavir/surfactant adduct according to the invention and pharmaceutical compositions containing it may be used in combination with antiretroviral or other agents that are generally administered to a patient being treated for HIV or AIDS. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition of the invention, that is one having at least one crystalline lopinavir/surfactant adduct of the invention, a carrier should be chosen that maintains the crystalline form. In other words, the carrier should not substantially alter the crystalline lopinavir/surfactant adduct. Nor should the carrier be otherwise incompatible with the crystalline lopinavir/surfactant adduct used, such as by producing any undesirable biological effect or otherwise interacting in a deleterious manner with any other component(s) of the pharmaceutical composition.

The pharmaceutical compositions of the invention may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, at least one crystalline lopinavir/surfactant adduct may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that may be prepared by mixing at least one crystalline lopinavir/surfactant adduct according to the invention with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Because the crystalline lopinavir/surfactant adduct is maintained during preparation, solid dosage forms are preferred for the pharmaceutical composition of the invention. Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier). The crystalline lopinavir/surfactant adducts according to the invention may also be used as precursors in the formulation of liquid pharmaceutical compositions. Administration of the crystalline lopinavir/surfactant adducts in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, intrasystemically, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the musculoskeletal condition to be treated.

The invention also relates to preparation of a medicament using the crystalline liponavir/surfactant adducts of the invention for inhibiting HIV protease, inhibiting HIV infection, and treating HIV infection.

Pharmaceutical Compositions Containing Lopinavir Prepared from Crystalline Lopinavir/Surfactant Adducts The invention also relates to pharmaceutical compositions comprising a therapeutically effective amount of lopinavir prepared by melting at least one crystalline lopinavir/surfactant adduct according to the invention and at least one excipient to produce a melt and solidifying the melt. In another embodiment, pharmaceutical compositions comprising a therapeutically effective amount of lopinavir may be prepared by dissolving at least one crystalline lopinavir/surfactant adduct according to the invention and at least one excipient in a solvent, and drying the solvent. In another embodiment, pharmaceutical compositions comprising a therapeutically effective amount of lopinavir may be prepared by milling at least one crystalline lopinavir/surfactant adduct according to the invention and at least one excipient. In another embodiment, pharmaceutical compositions comprising a therapeutically effective amount of lopinavir may be prepared by dissolving at least one crystalline lopinavir/surfactant adduct according to the invention in a solution.

Any of the crystalline lopinavir/surfactant adducts according to the invention may be used to prepare a pharmaceutical composition comprising a therapeutically effective amount of lopinavir. These pharmaceutical compositions are also therapeutically useful for inhibiting HIV protease, inhibiting HIV infection, and treating HIV infection.

EXAMPLES

The following analytical methods were used to characterize the crystalline lopinavir/surfactant adducts of the invention:

X-Ray Powder Diffraction:

X-ray powder diffraction studies were performed on a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromator provided monochromatic K$\alpha$1 radiation. The diffractometer was calibrated using the attenuated direct beam at one-degree intervals. Calibration was checked using a silicon powder line position reference standard (NIST 640c). The instrument was computer controlled using the Symphonix software (Inel Corp., Artenay, France) and the data was analyzed using the Jade software (version 6.5, Materials Data, Inc., Livermore, Calif.). The sample was loaded onto an aluminum sample holder and leveled with a glass slide.

Single Crystal X-Ray Diffraction (SCXRD):

Data were collected on a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromator provided monochromatic K$\alpha$1 radiation. The diffractometer was calibrated using the attenuated direct beam at one-degree intervals. Calibration was checked using a silicon powder line position reference standard (NIST 640c). The instrument was computer controlled using the Symphonix software (Inel Corp., Artenay, France) and the data was analyzed using the Jade software (version 6.5, Materials Data, Inc., Livermore, Calif.). The sample was loaded onto an aluminum sample holder and leveled with a glass slide.

Differential Scanning Calorimetry (DSC):

A DSC (Q-2000, TA Instruments, New Castle, Del.) equipped with Universal Analysis 2000 software (Version 4.5A, TA Instruments, New Castle, Del.) was used to determine the DSC thermal traces. The temperature axis was calibrated with biphenyl, indium, and tin standards. The cell constant was calibrated with indium. Unless otherwise stated, the sample (2-5 mg) was encapsulated in a ventilated aluminum pan, and heated at a rate of 10° C./min under a nitrogen gas flow of 50 mL/min during the study.

Thermo-Gravimetric Analysis (TGA):

TGA traces were collected on a thermal balance (Q-500, TA Instruments, New Castle, Del.) equipped with a data analyzer (Universal Analysis 2000, version 4.5A, TA Instruments, New Castle, Del.). During experiments, the furnace was purged with nitrogen at 60 mL/min, while the balance chamber was purged at 40 mL/min. Temperature of the TGA furnace was calibrated using curie points of alumel and nickel. Sample size ranged from 2 to 20 mg, and a heating rate of 10° C./min was used.

Dynamic Moisture Sorption Balance:

Hygroscopicity was evaluated on a dynamic moisture sorption balance (IGAsorp, Hiden Isochema, Warrington, UK) equipped with a data analyzer (IGAsorp, version 6.0.0.23, Hiden Isochema, Warrington UK). The balance was calibrated using standardized weights of 20, 50, and 100 mg. The RH probe was calibrated using standardized salt solutions of Lithium Chloride, Potassium Carbonate, and Sodium Chloride. During the experiment, the flow rate of nitrogen gas at different relative humidity was 250 mL/min. For anhydrous materials, the sample was first dried with dry nitrogen at 50° C. for two hours. The temperature was then set to 25° C. and the relative humidity was changed from 0% to 90% and back to 0% at 10% interval. For hydrated samples, the temperature was set to 25° C. and the relative humidity was changed at 10% interval from 30% to 90%, back to 10%, and then to 90%. One hour equilibration time was used at each step.

Solution Nuclear Magnetic Resonance (NMR) ($^1$H):

NMR data were collected on a Varian Mercury NMR Spectrometer (Varian Inc, Palo Alto, USA) operating at 400 MHz $^1$H frequency. This instrument is controlled by a Sun Ultra 10 workstation running solaris 5.8 and spectrometer software VNMR 6.1 C. Typical acquisition parameters are: 32-128 scans of 32 K complex points; a sweep width of −2 to 20 ppm; acquisition time of 3.5 sec with a relaxation delay of 1 sec using a 45° pulse width. Probe temperature is set to 25° C. Spectra are referenced to internal TMS or the residual protonated solvent resonance.

FT-Raman Spectroscopy:

Raman spectra of the solid samples were recorded using a FT-Raman system (Nicolet) equipped with a 200-mW diode pumped Nd:YAG laser operating at 765 nm as the excitation source. Backscattered radiation was collected from the sample pre-filled in a glass vial using a liquid nitrogen-cooled germanium detector. The solid sample was filled in a borosilicate glass vial and measured in the sample compartment where the laser power was approximately 100 mW at the sample. For solid form identification purpose, an average of 256 scans was typically used to achieve an adequate signal-to-noise ratio.

IR Microscopy:

Transmission infrared spectra of the solids were obtained using a Fourier-transform infrared spectrometer (Nicolet Magna 750 FT-IR Spectrometer) equipped with a Nicolet NIC-PLAN microscope. The microscope has an MCT-A liquid nitrogen cooled detector. The samples were rolled on a 13 mm×1 mm BaF$_2$ disk sample holder; 64 scans were collected at 4 cm$^{-1}$ resolution.

Example 1

Crystalline Lopinavir/Surfactant Adducts 1.1 Materials Used

Amorphous lopinavir and the following surfactants listed in Table 1 were used in the preparation of the crystalline adducts of lopinavir and surfactant. Table 1 also provides the weight ratio of the crystalline adducts of lopinavir and surfactant.

TABLE 1

Crystalline Adducts of Lopinavir/Surfactants

| Crystalline Adduct | Weight Ratio |
|---|---|
| LPV/Capyrol 90 | 9/1 |
| LPV/Cremophor EL | 9/1 |
| LPV/Cremophor RH40 | 9/1 |
| LPV/Lauroglycol FCC | 9/1 |
| LPV/Lauroglycol Type 1 | 10/1 |
| LPV/Oleic acid | 10/1 |
| LPV/Plurol Oleique | 9/1 |
| LPV/Pluronic F68 | 9/1 |
| LPV/Soluto HS15 | 10/1 |
| LPV/Span 20 | 9/1 |
| LPV/Span 40 | 10/1 |

TABLE 1-continued

Crystalline Adducts of Lopinavir/Surfactants

| Crystalline Adduct | Weight Ratio |
|---|---|
| LPV/Span 80 | 9/1 |
| LPV/Tween 20 | 9/1 |
| LPV/Tween 65 | 9/1 |
| LPV/Tween 80 | 9/1 |
| LPV/VitE TPGS | 9/1 |

1.2 Preparation of Amorphous Lopinavir

Amorphous lopinavir was prepared by dehydration of crystalline lopinavir hydrate Type I at 90° C. under vacuum overnight.

1.3 Preparation of Crystalline Lopinavir/Surfactant Adducts by Melt Extrusion

Sixteen crystalline adducts of the mixtures of lopinavir and surfactants identified in Table 1 above were prepared by melt extrusion. The crystalline adducts were stored in closed glass vials at 60° C. for 10 weeks prior to shipment. The crystalline adducts were stored in the same closed glass vial at ambient conditions until measurements.

1.4 Preparation of Crystalline Lopinavir/Lauroglycol Adduct by Grinding 5001.71 mg of crystalline lopinavir hydrate Type I was added to a mortar. 1036.37 mg of lauroglycol FCC was added to lopinavir by droplets while mixed by a spatula. Mixture was ground for 10-20 minutes by a pestle, then, left aging at ambient temperature for several hours. Grinding and aging were repeated for 4-5 times until lopinavir completely converted to Type III crystals.

1.5 XRPD and Raman Characterization of Crystalline Lopinavir/Surfactant Adducts

The XRPDs of the crystalline lopinavir/surfactant adducts show very similar patterns (FIGS. 2-18). The XRPD patterns of the solid samples contain all the characteristic peaks of that of Type III crystalline lopinavir/surfactant form, which suggests that the solid samples have the same or similar crystal lattices to that of the Type III lopinavir crystal form (FIG. 1). The entire list of peaks, or a subset thereof, may be sufficient to characterize each of the crystalline lopinavir/surfactant adducts, including: 4.8, 7.3, 8.8, 9.7, 10.3, 12.2, 12.8, 14.7, 16.4, 17.6, 18.6, 20.0, 21.9, 22.5, and 23.0°2θ±0.2°2θ.

Figure 19:
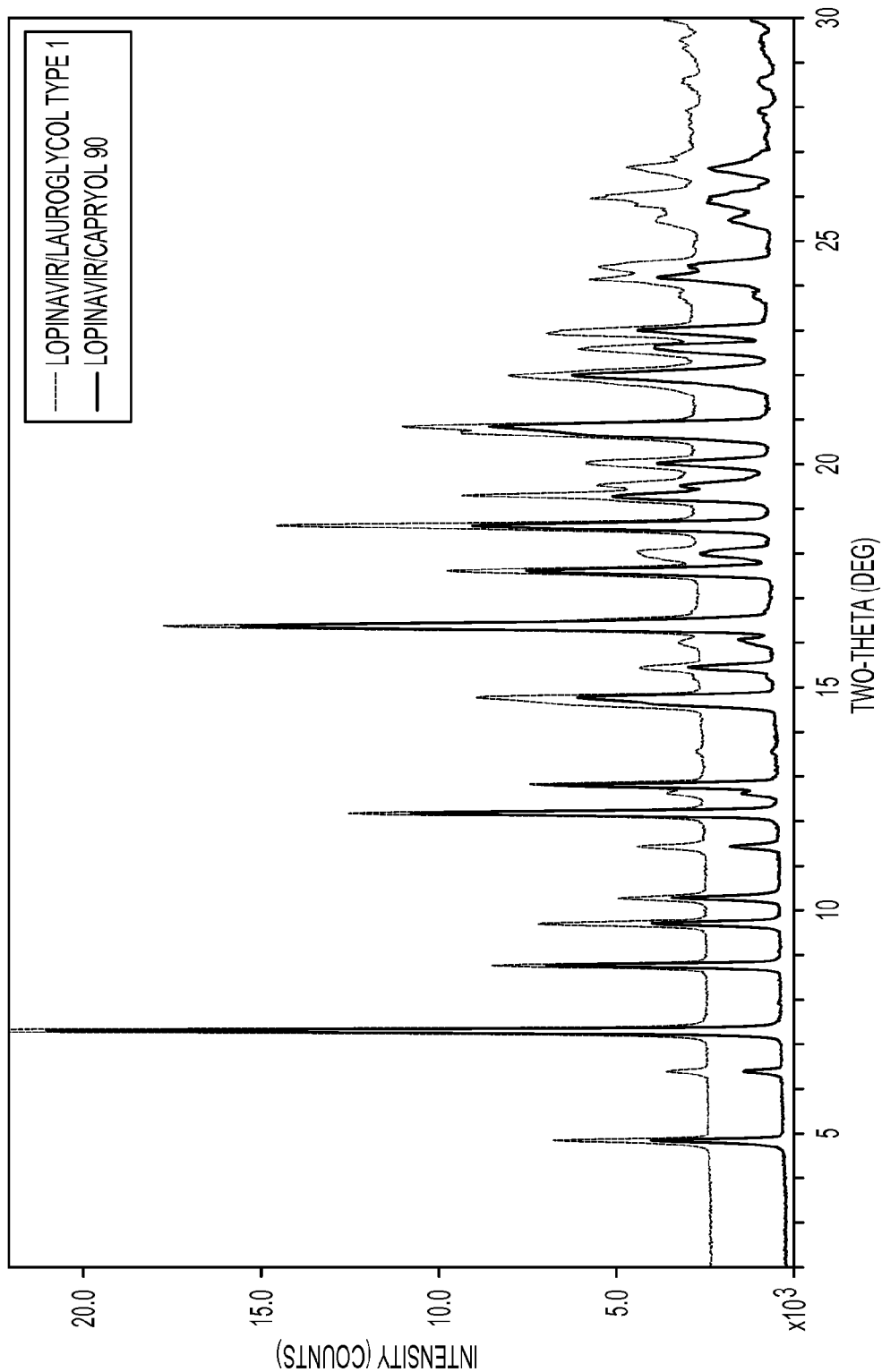
FIG. 19 shows XRPD patterns of crystalline adducts of lopinavir/Lauroglycol Type I and lopinavir/Capryol 90.
Figure 20:
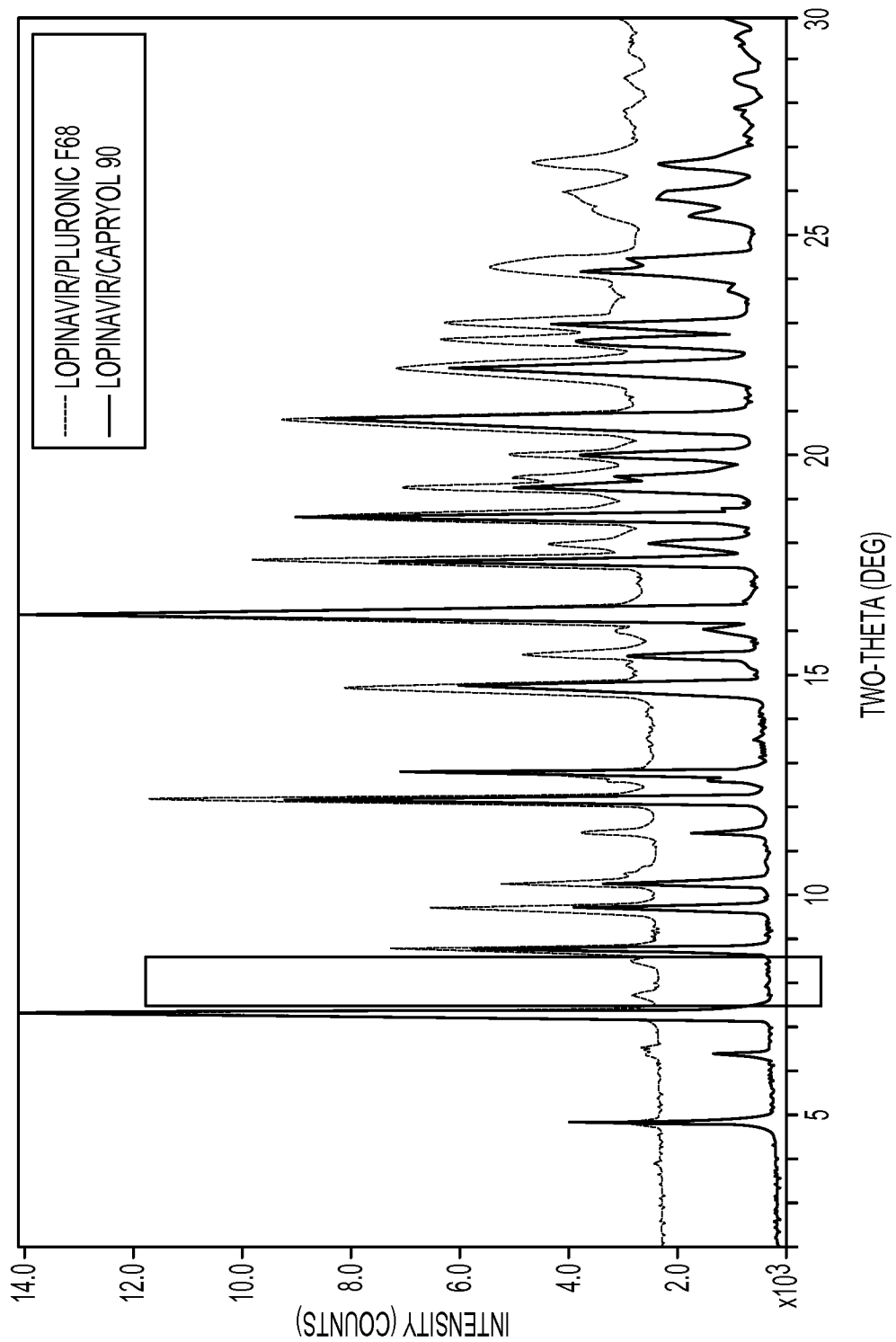
FIG. 20 shows XRPD patterns of crystalline adducts of lopinavir/Pluronic F68 and lopinavir/Capryol 90.
Figure 21:
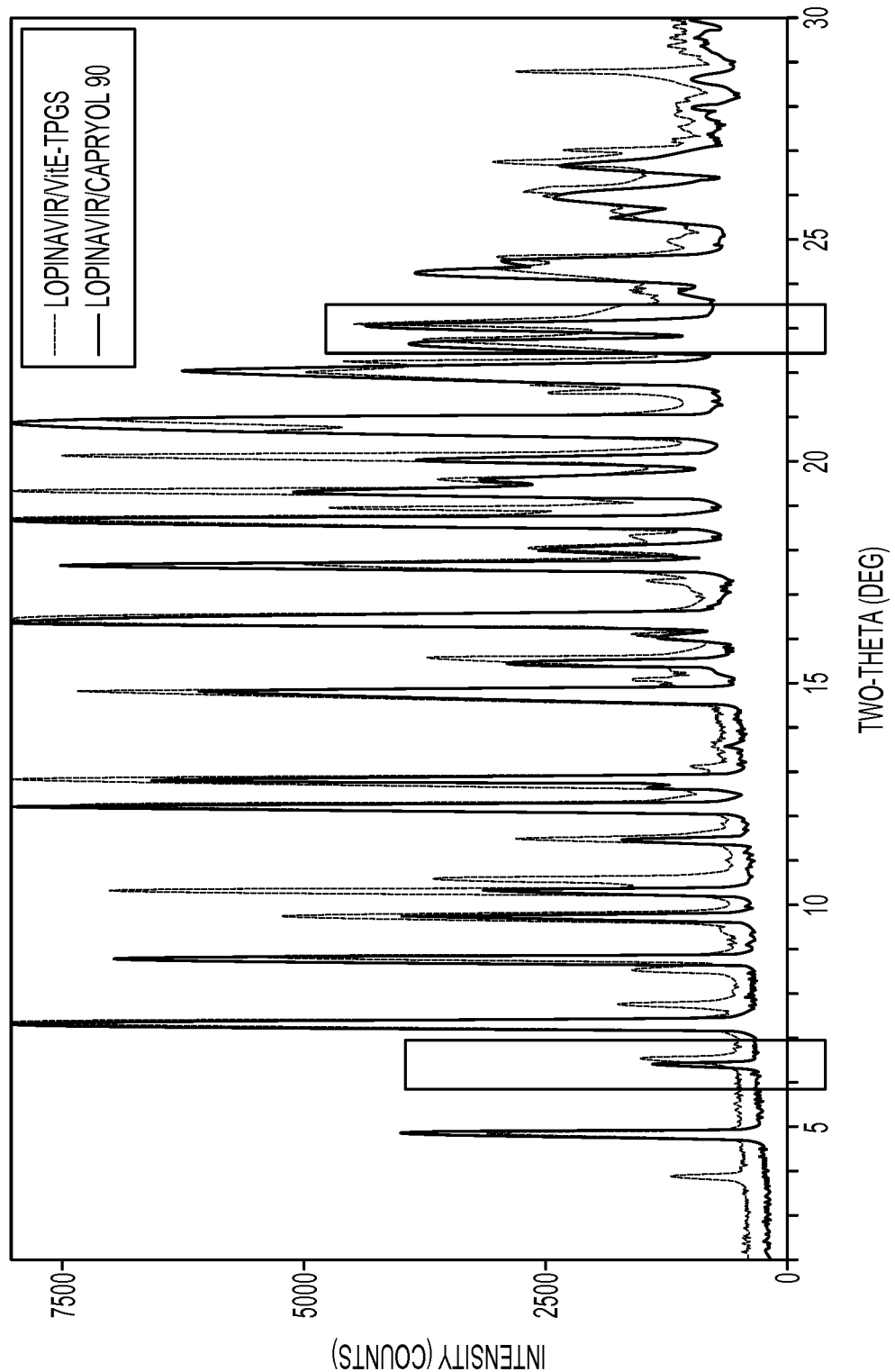
FIG. 21 shows XRPD patterns of crystalline adducts of lopinavir/VitE TPGS and lopinavir/Capryol 90.
Figure 22:
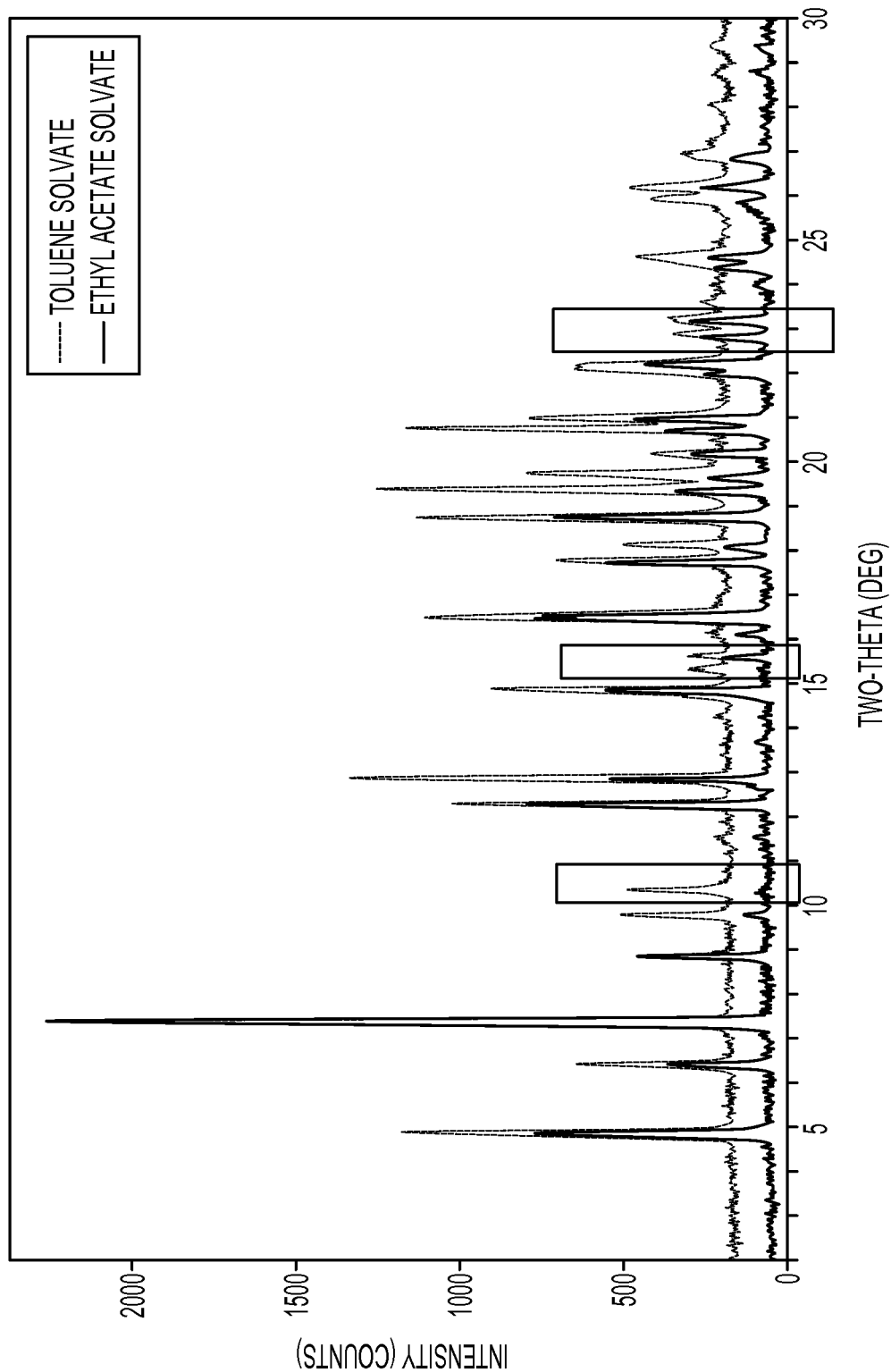
FIG. 22 shows XRPD patterns of toluene and EtOAc Type III solvates of lopinavir.
Figure 23:
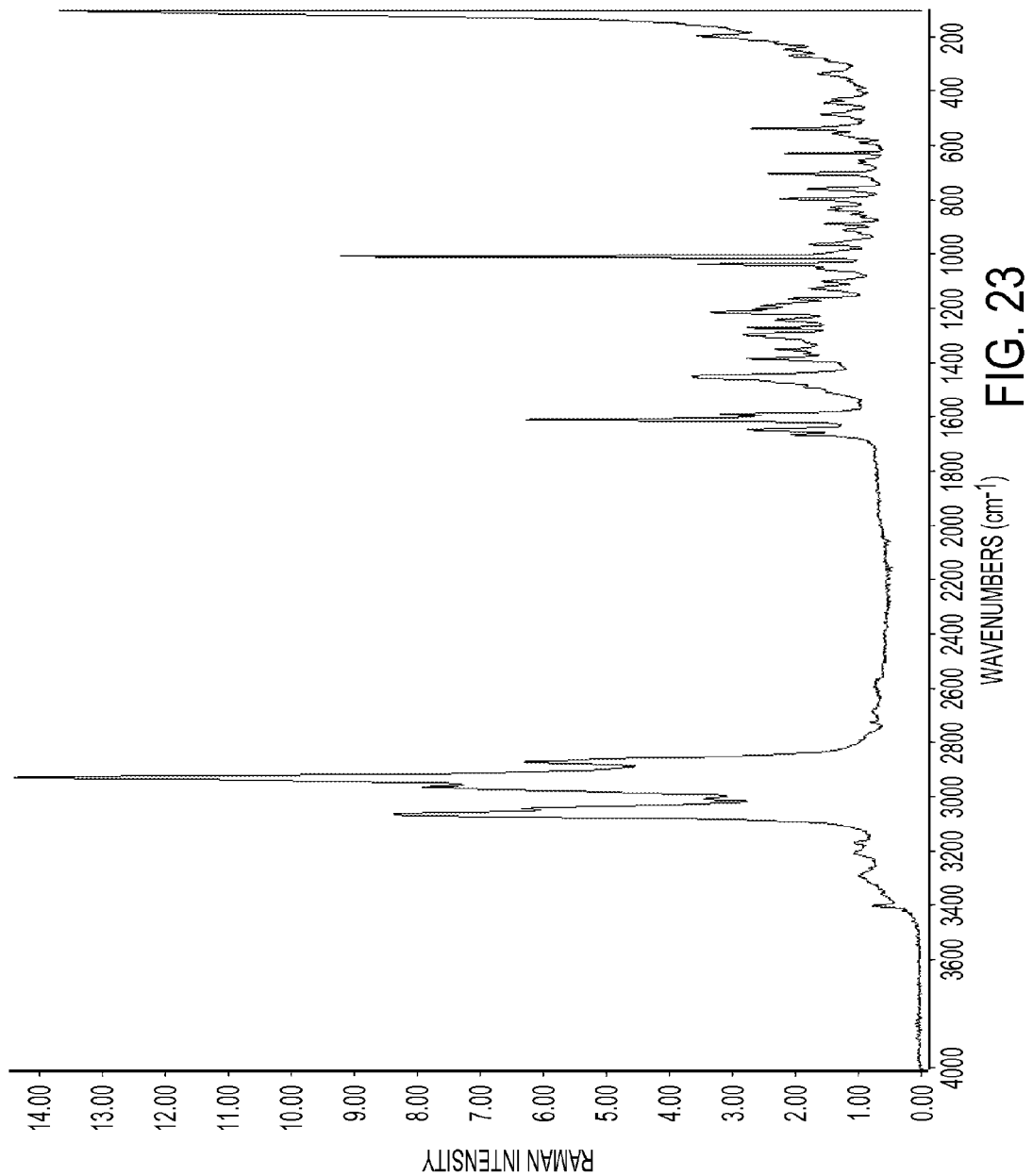
FIG. 23 shows a Raman spectra of a crystalline adduct of lopinavir/VitE TPGS.
Figure 24:
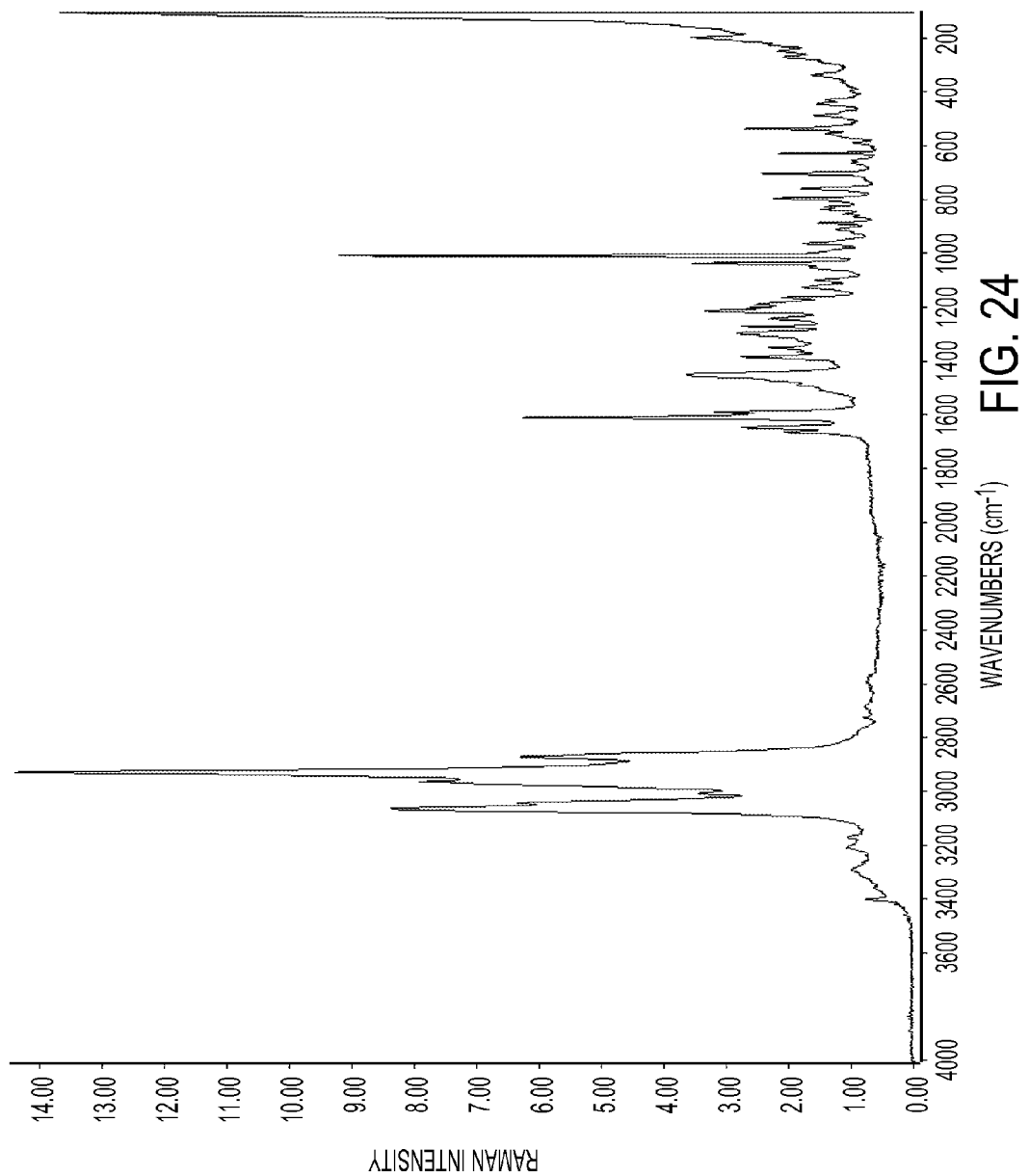
FIG. 24 shows a Raman spectra of a crystalline adduct of lopinavir/Tween 80.
Figure 25:
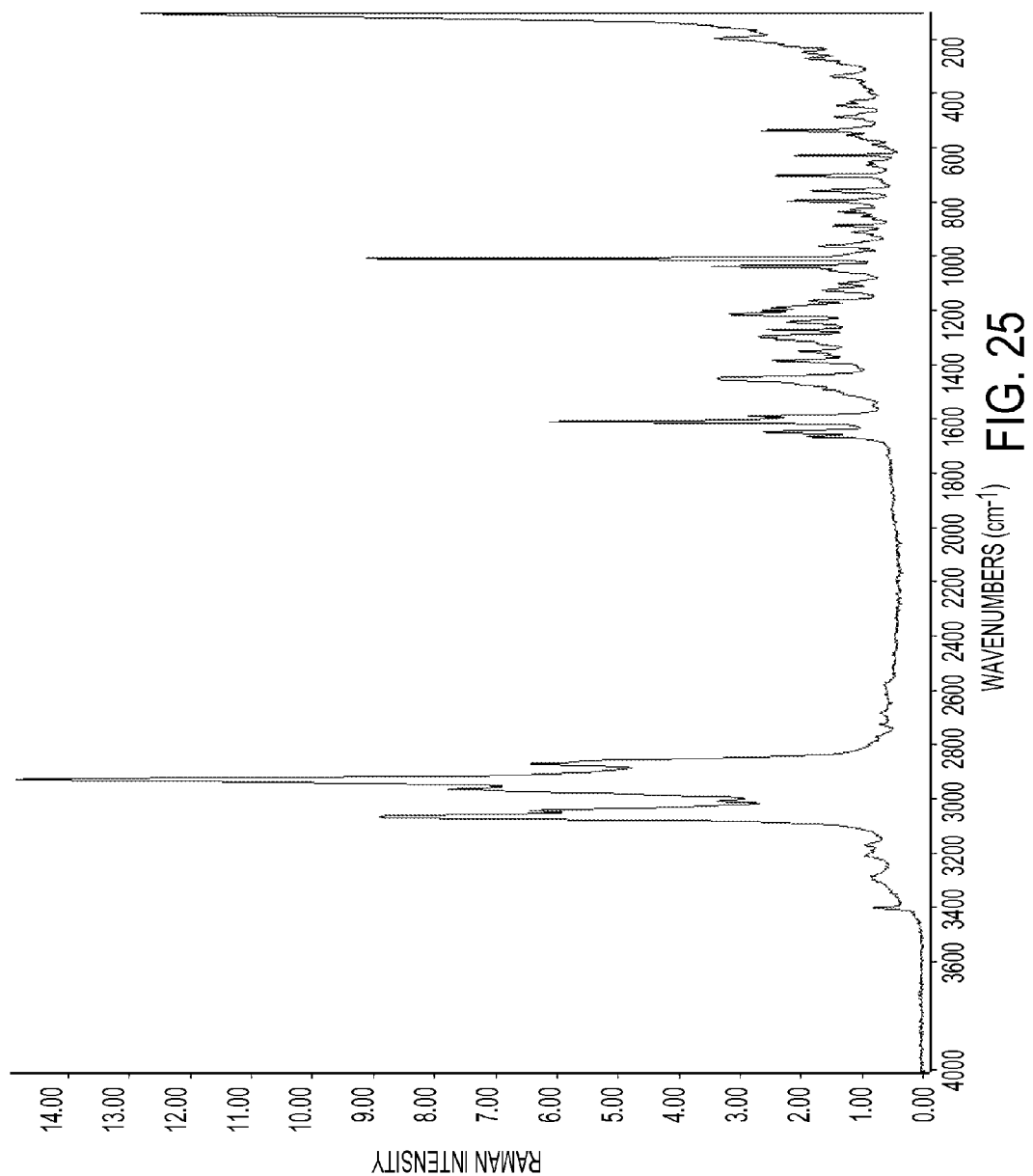
FIG. 25 shows a Raman spectra of a crystalline adduct of lopinavir/Tween 65.
Figure 26:
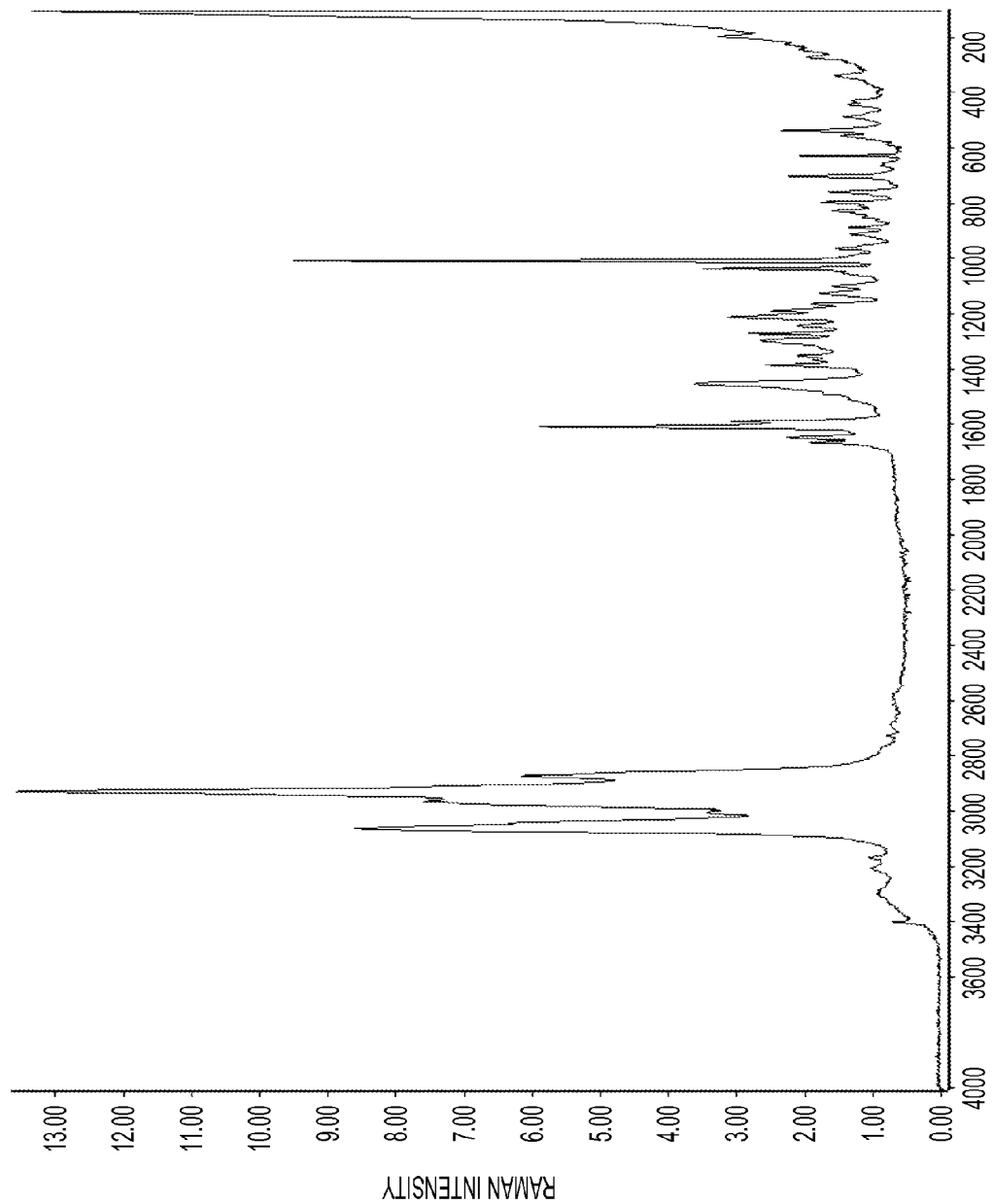
FIG. 26 shows a Raman spectra of a crystalline adduct of lopinavir/Tween 20.
Figure 27:
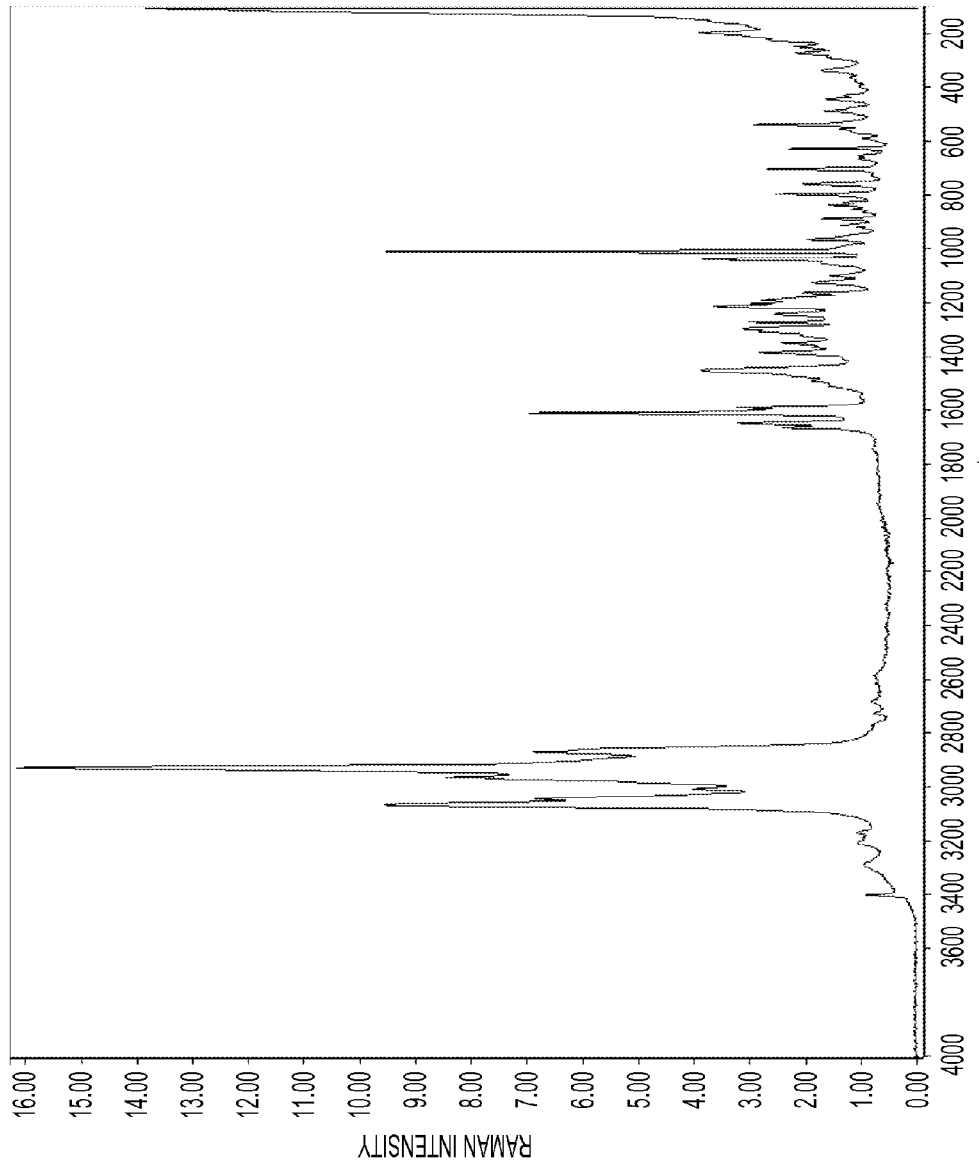
FIG. 27 shows a Raman spectra of a crystalline adduct of lopinavir/Span 80.
Figure 28:
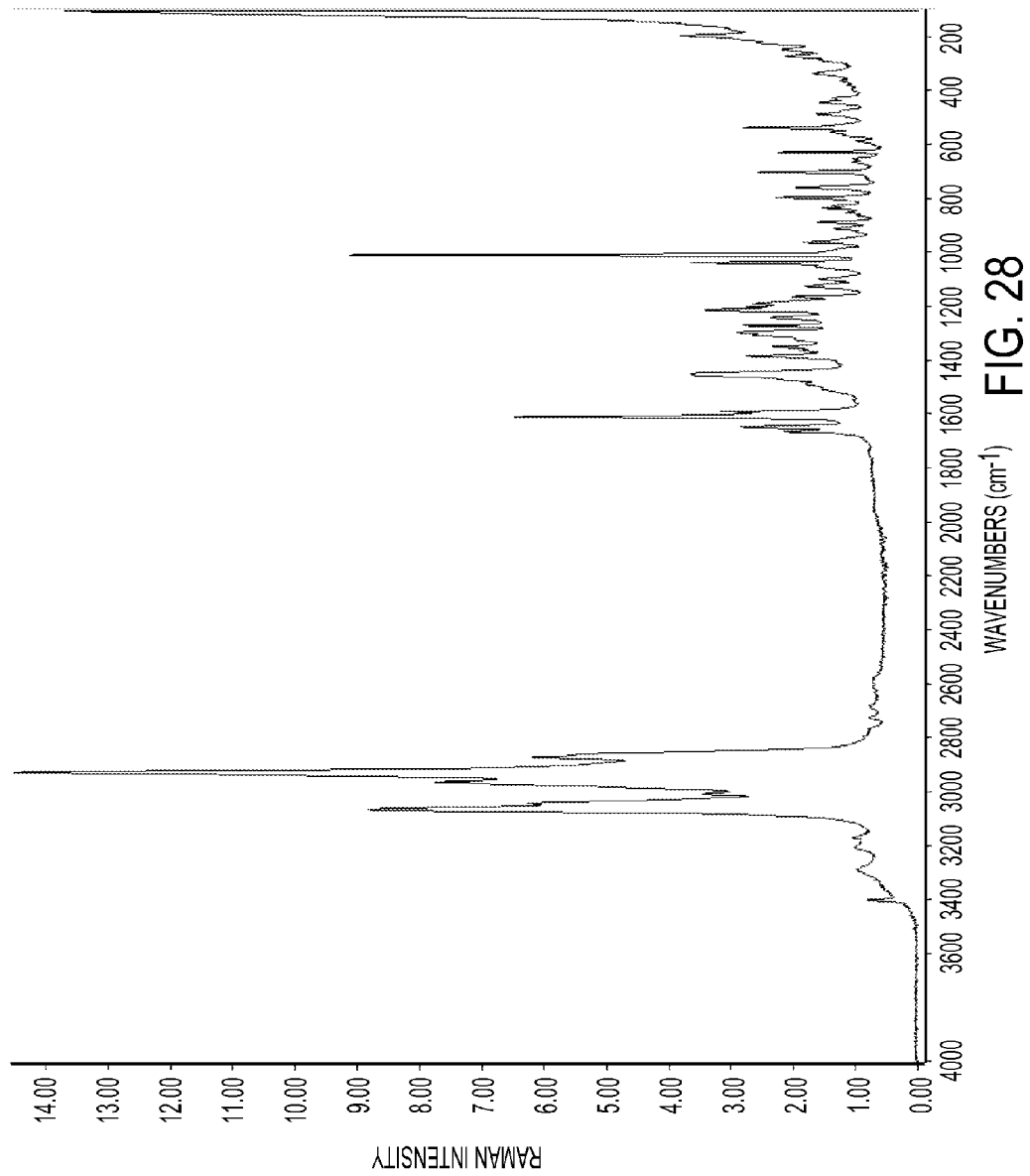
FIG. 28 shows a Raman spectra of a crystalline adduct of lopinavir/Span 40.
Figure 29:
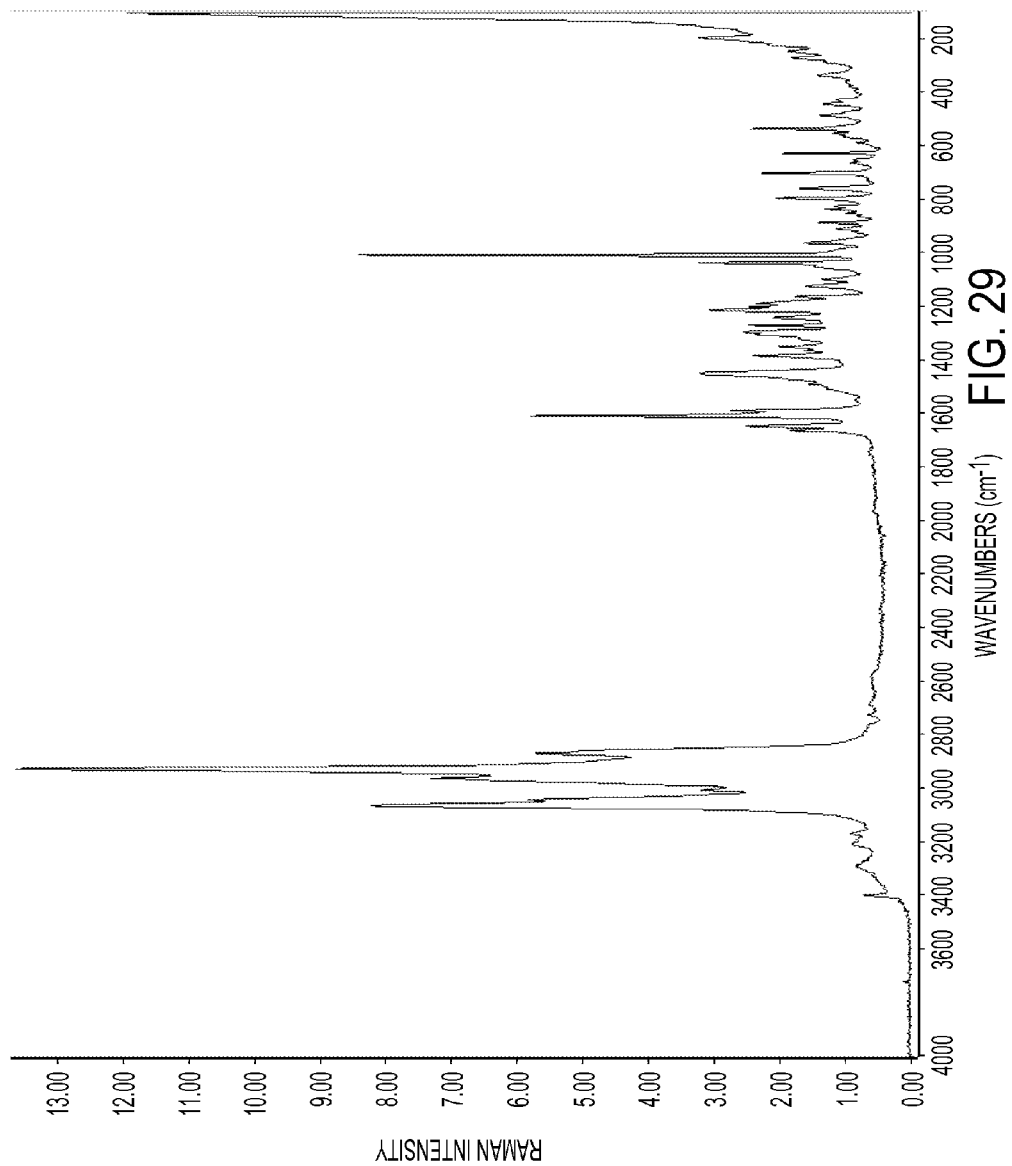
FIG. 29 shows a Raman spectra of a crystalline adduct of lopinavir/Span 20.
Figure 30:
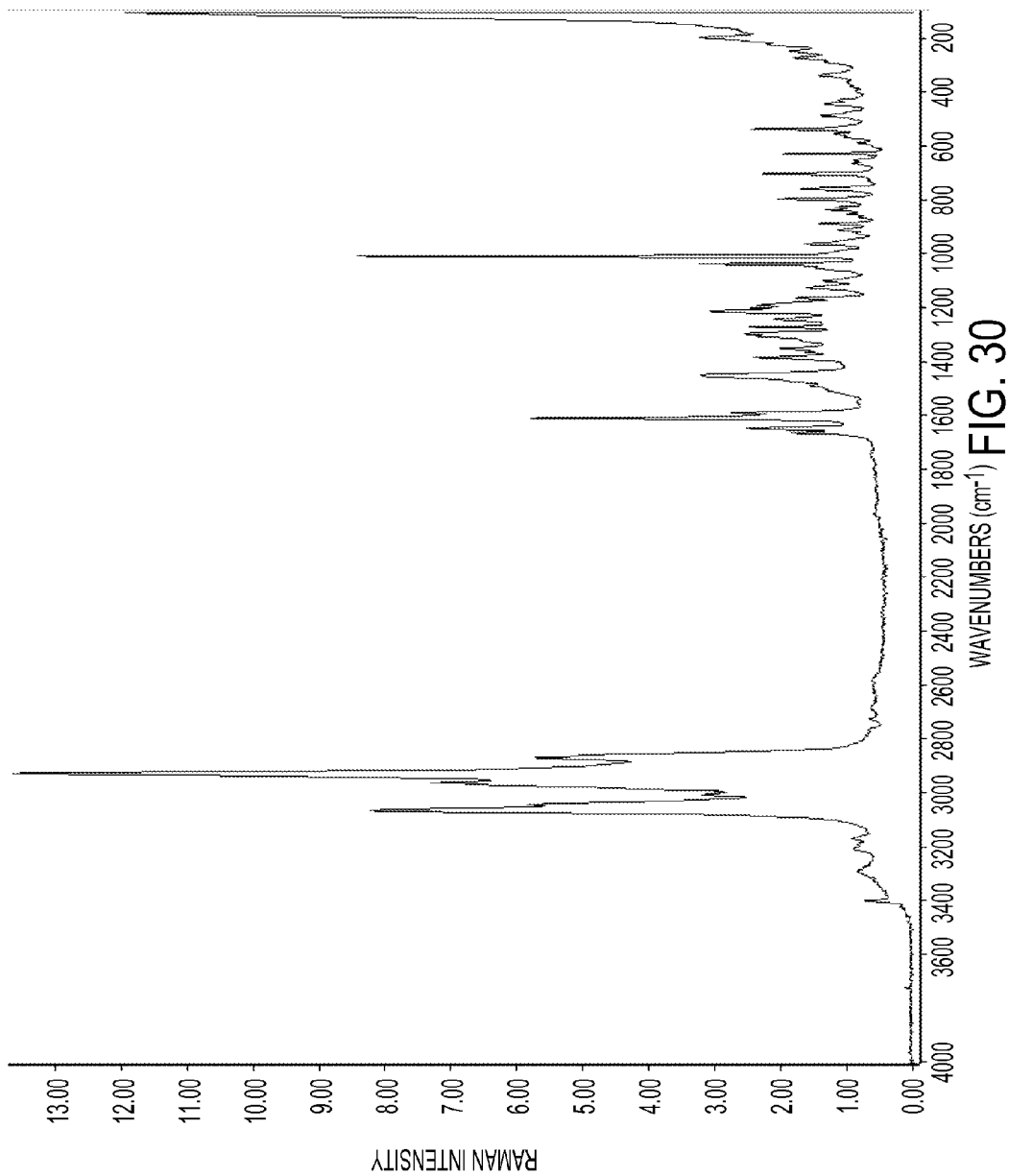
FIG. 30 shows a Raman spectra of a crystalline adduct of lopinavir/Solutol HS15.
Figure 31:
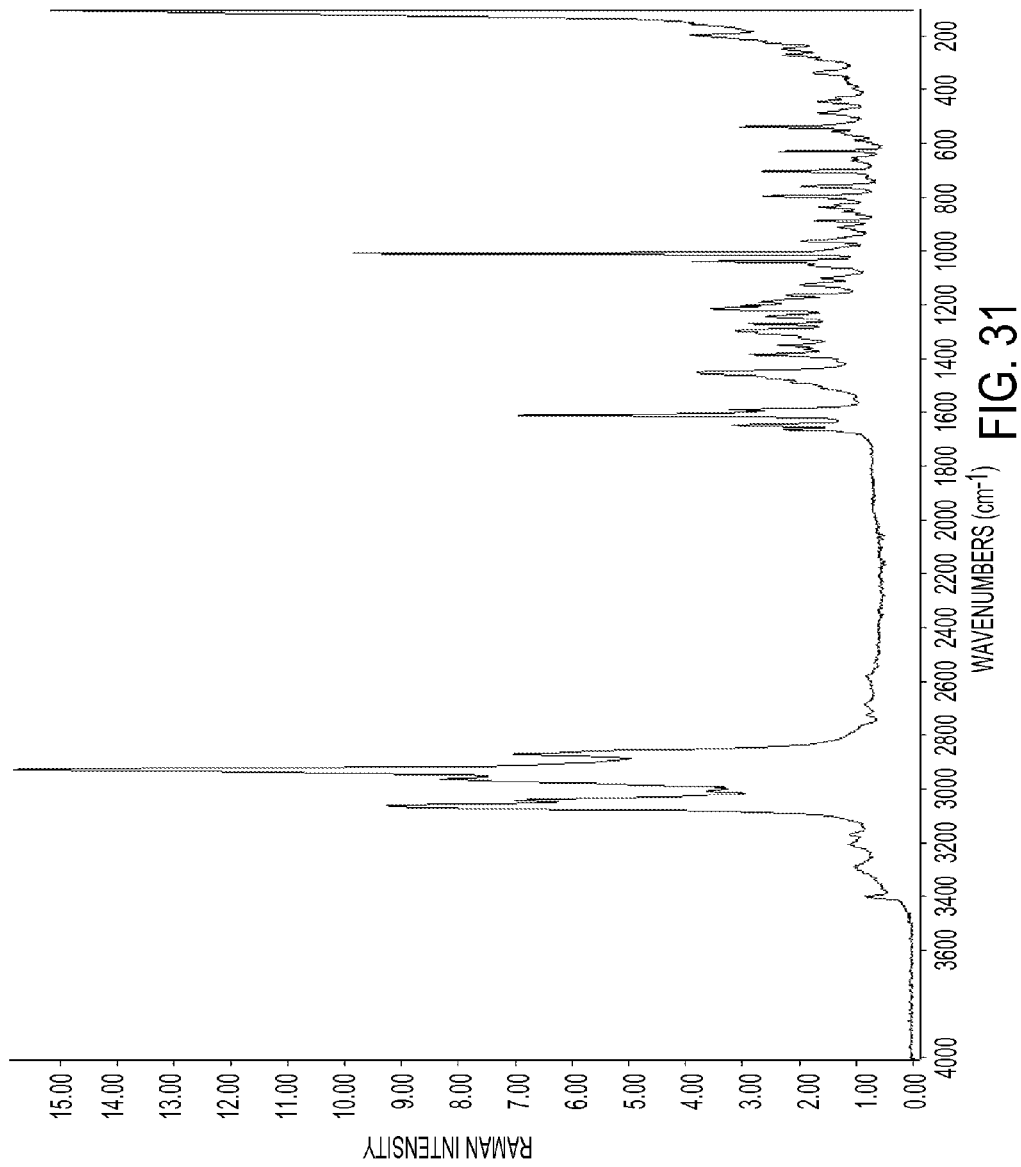
FIG. 31 shows a Raman spectra of a crystalline adduct of lopinavir/Pluronic F68.
Figure 32:
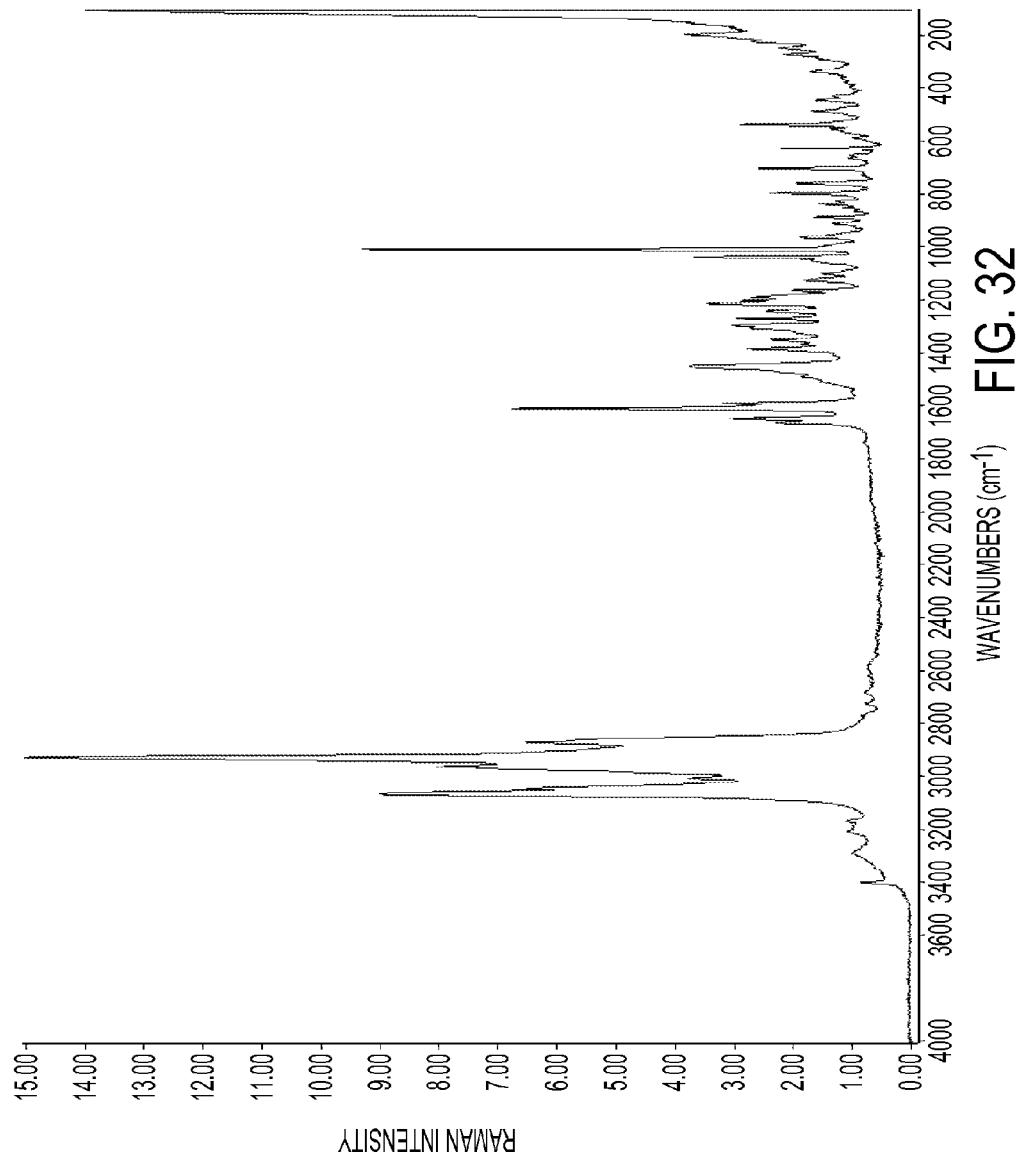
FIG. 32 shows a Raman spectra of a crystalline adduct of lopinavir/Plurol oleique.
Figure 33:
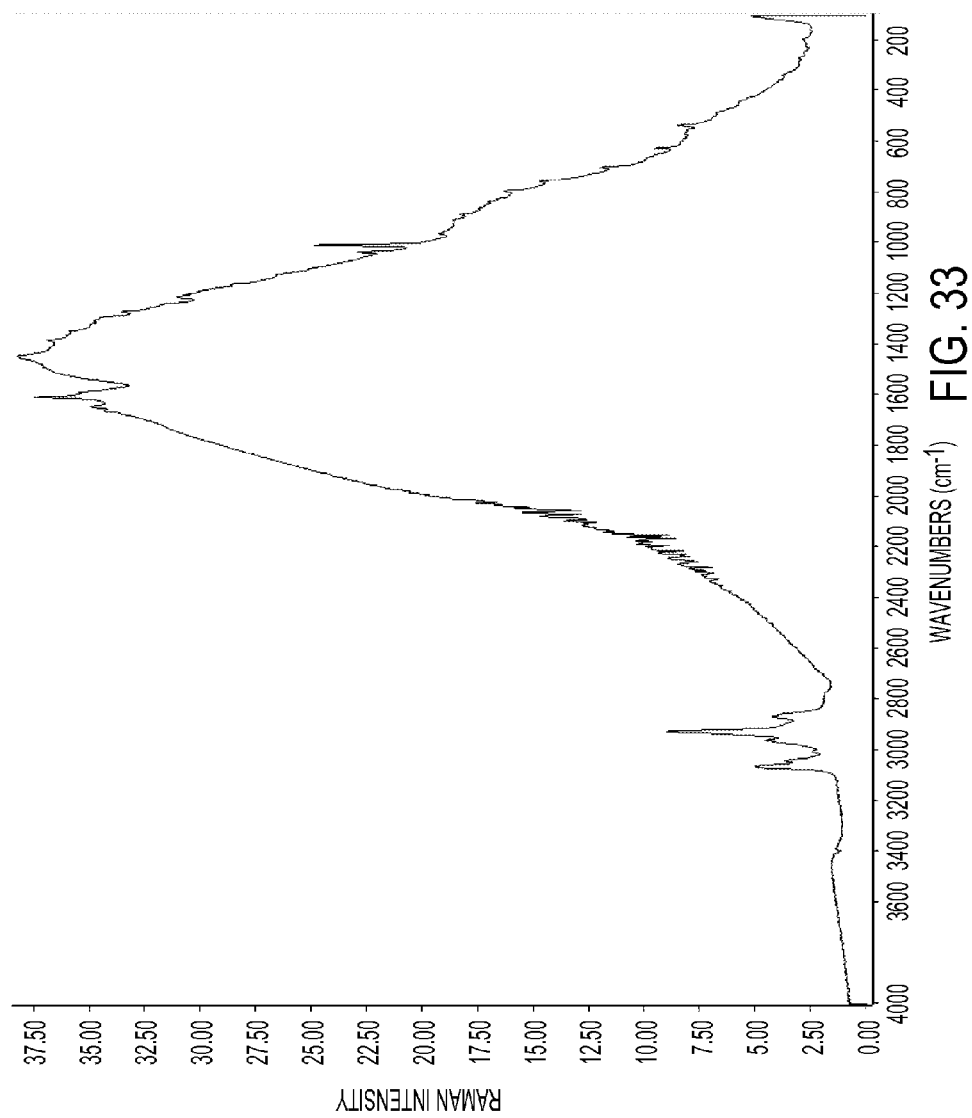
FIG. 33 shows a Raman spectra of a crystalline adduct of lopinavir/Oleic acid.
Figure 34:
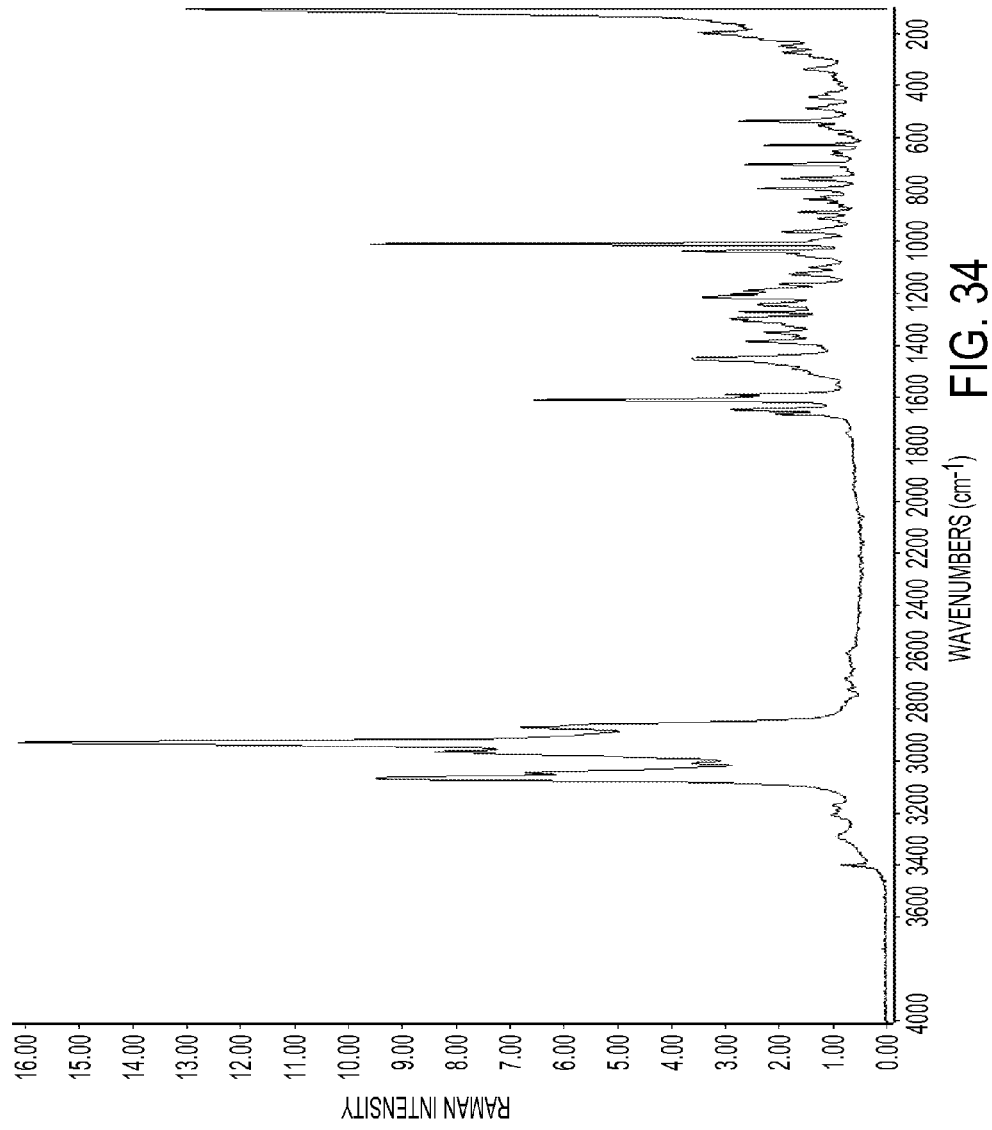
FIG. 34 shows a Raman spectra of a crystalline adduct of lopinavir/Lauroglycol Type I.
Figure 35:
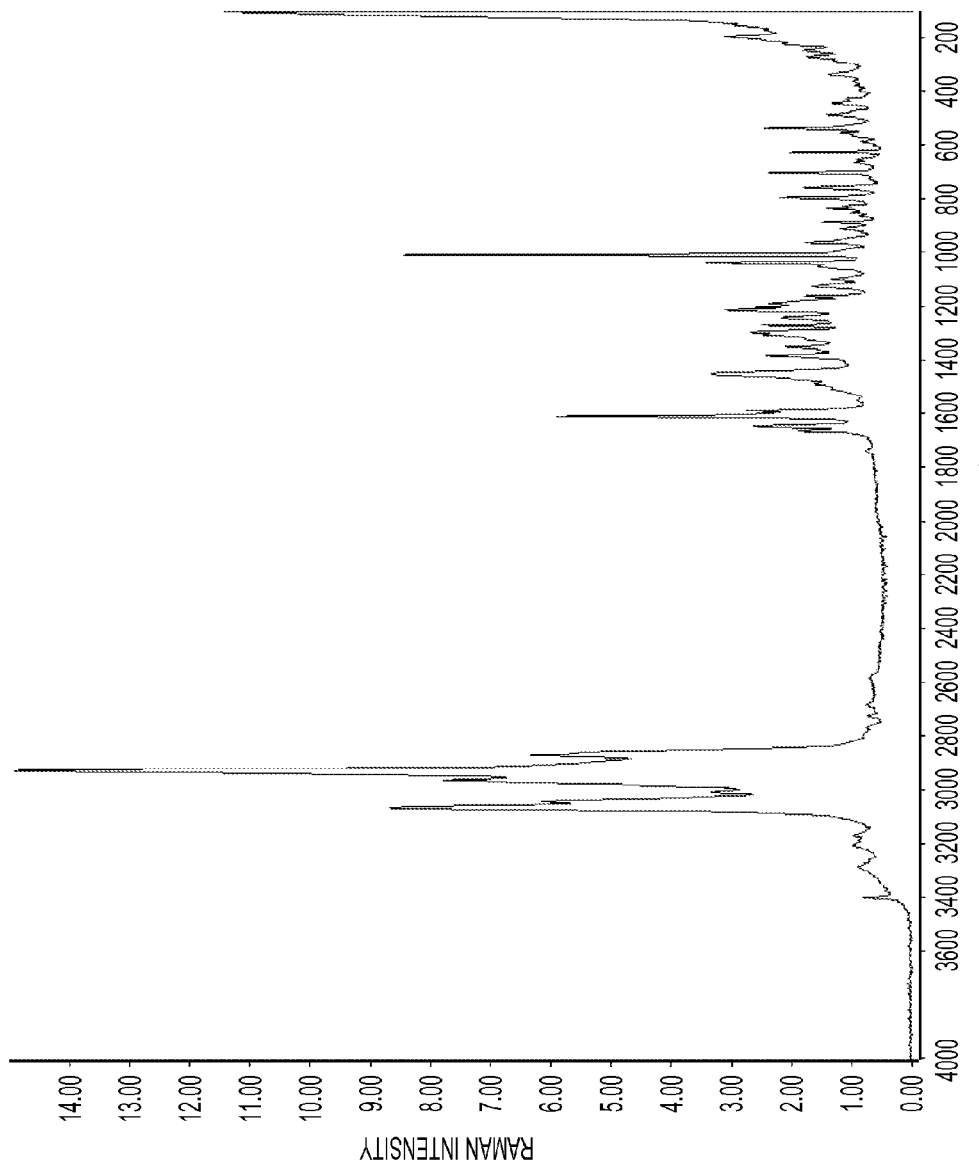
FIG. 35 shows a Raman spectra of a crystalline adduct of lopinavir/Lauroglycol FCC.
Figure 36:
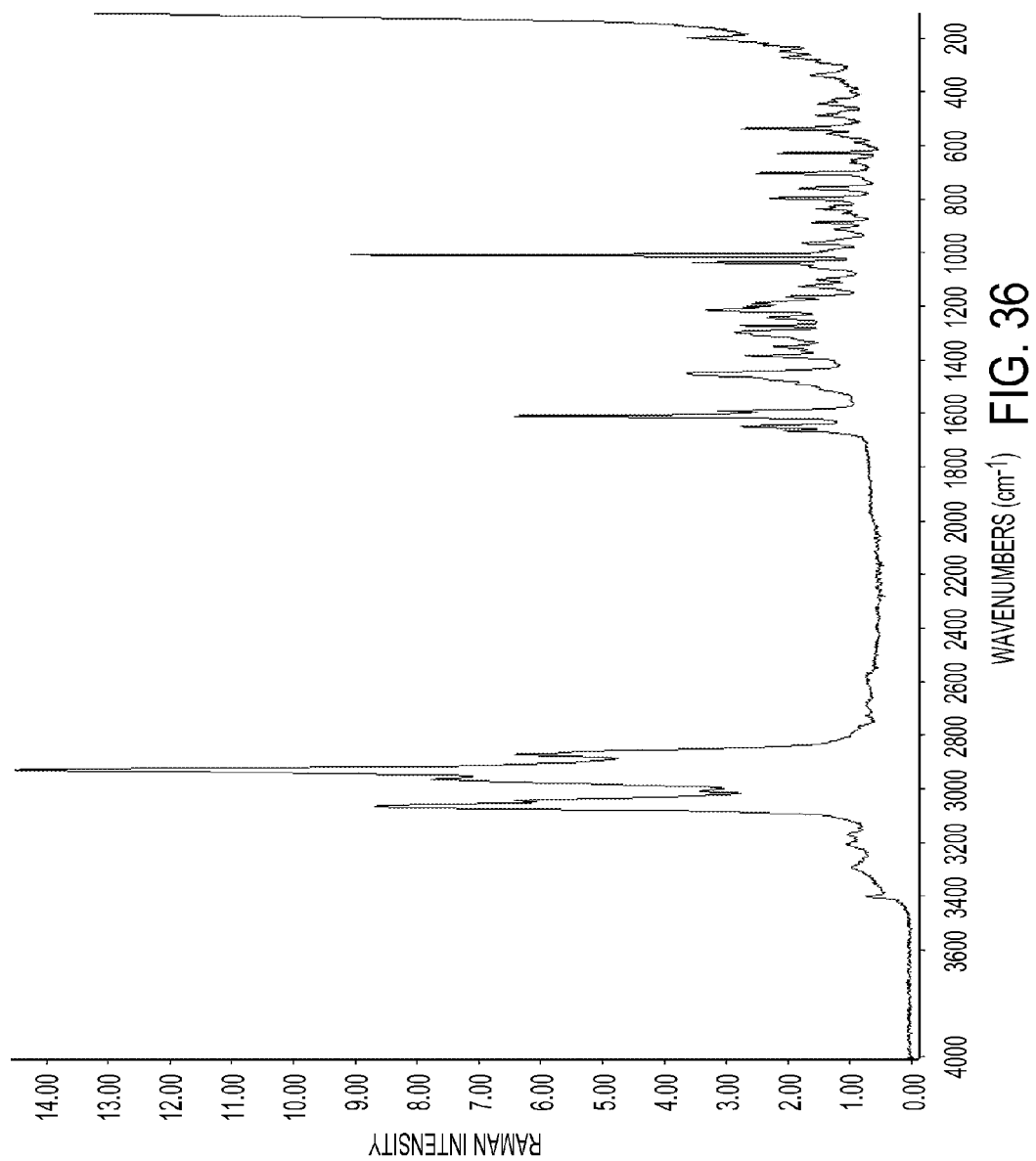
FIG. 36 shows a Raman spectra of a crystalline adduct of lopinavir/Cremophor RH40.
Figure 37:
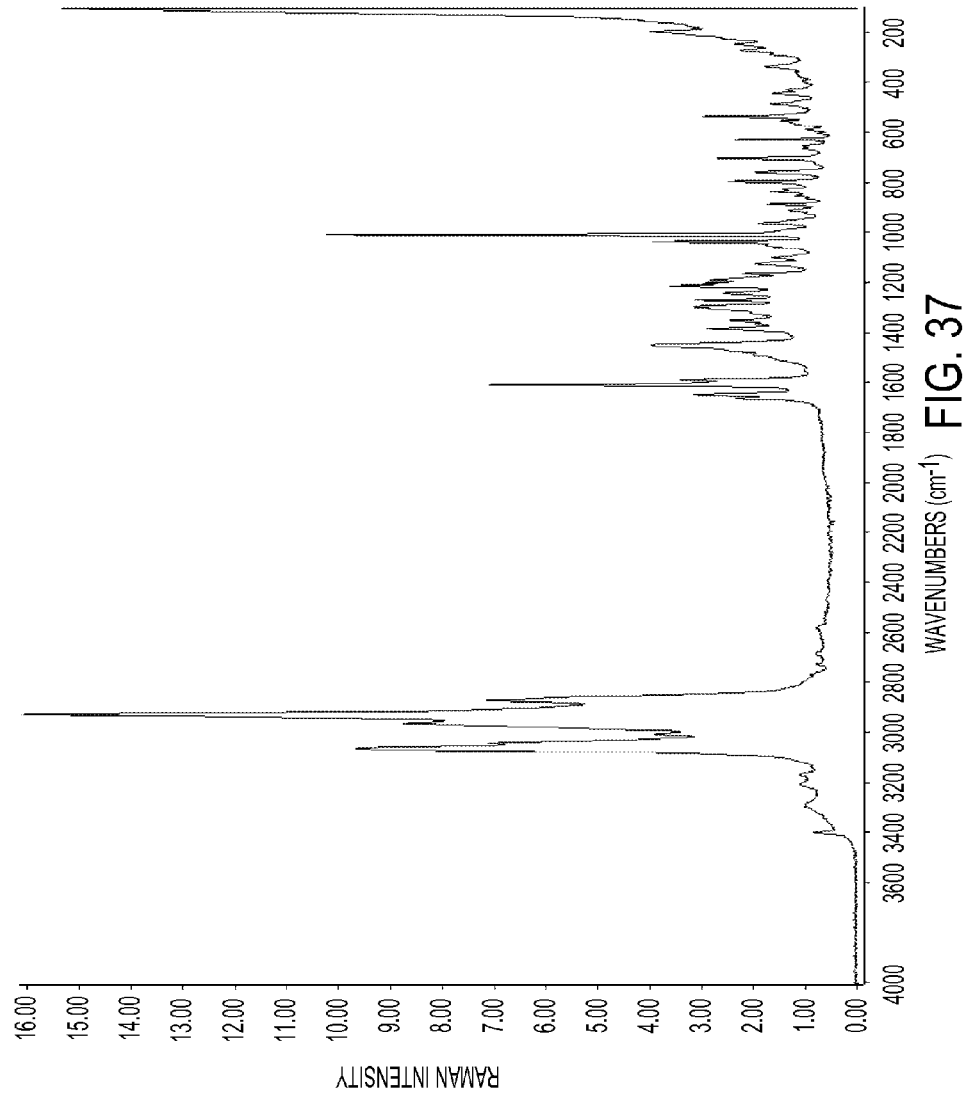
FIG. 37 shows a Raman spectra of a crystalline adduct of lopinavir/Cremophor EL.
Figure 38:
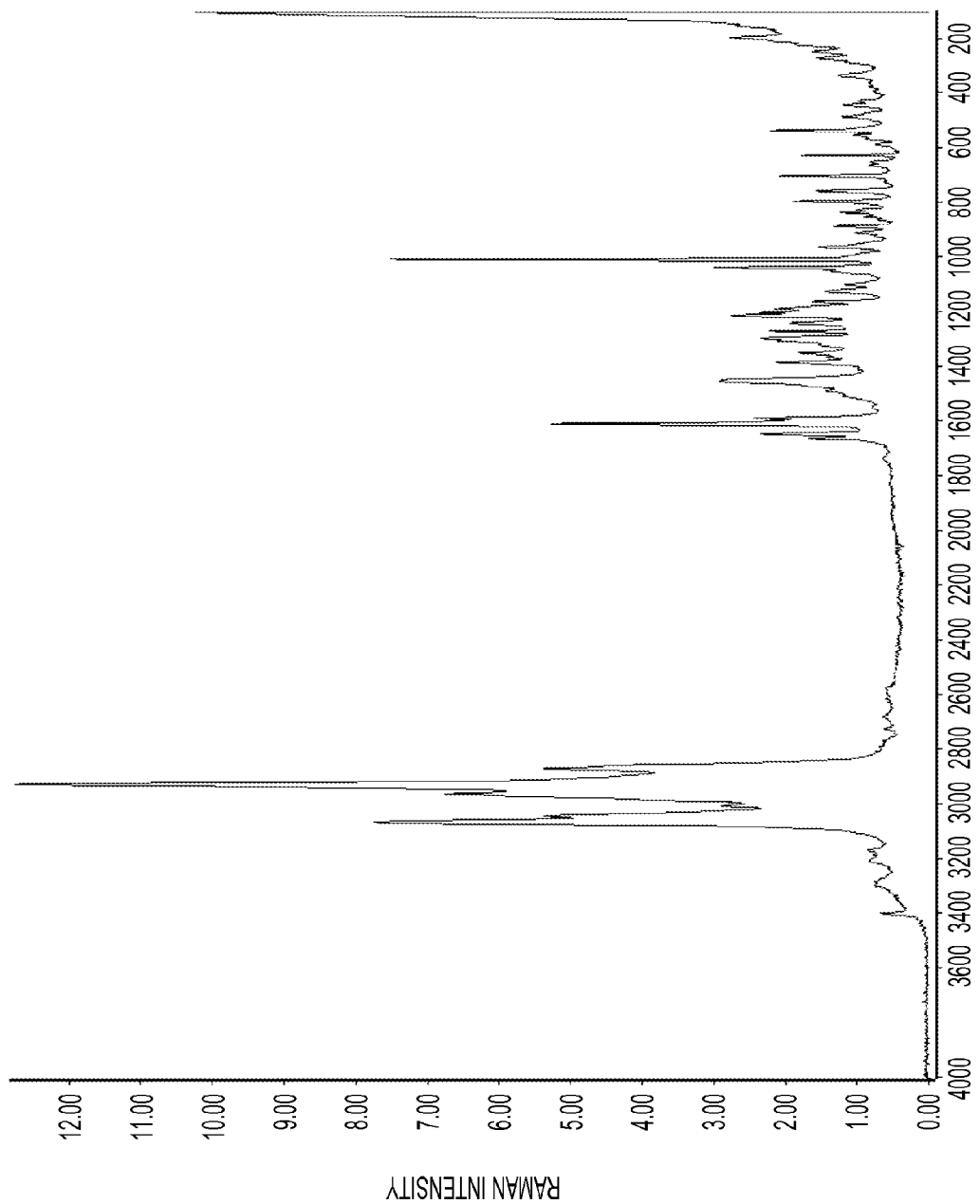
FIG. 38 shows a Raman spectra of a crystalline adduct of lopinavir/Capryol 90.
Figure 39:
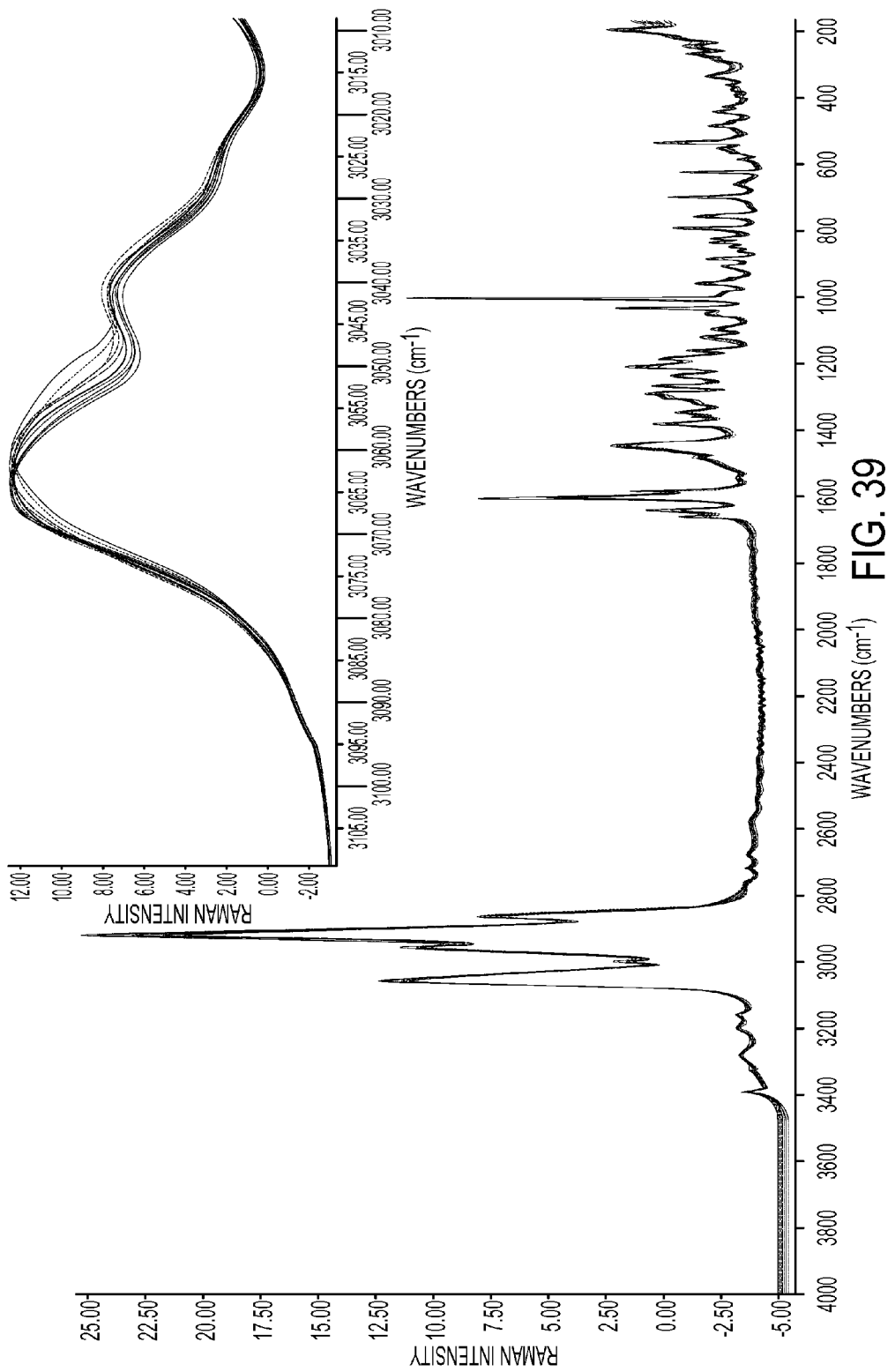
FIG. 39 shows an overlay of Raman spectra of crystalline lopinavir/surfactant adducts of the invention, including lopinavir/VitE TPGS, lopinavir/Tween 80, lopinavir/Tween 65, lopinavir/Tween 20, lopinavir/Span 80, lopinavir/Span 40, lopinavir/Span 20, lopinavir/Solutol HS15, lopinavir/Pluronic F68, lopinavir/Plurol oleique, lopinavir/Oleic acid, lopinavir/Lauroglycol Type I, lopinavir/Lauroglycol FCC, lopinavir/Cremophor RH40, lopinavir/Cremophor EL, and lopinavir/Capryol 90.

While XRPD patterns of some of the crystalline lopinavir/surfactant adducts overlay perfectly (FIG. 19), some patterns show extra peaks or peak shifts, which indicate subtle differences in the crystal lattices. For example, the XRPD pattern of lopinavir/Pluronic F68 shows two extra peaks at 7.8° and 8.5°/2θ (FIG. 20), and that of lopinavir/VitE TPGS shows slight peak shift at 6.4° and 22.6°/2θ (FIG. 21). Extra diffractions peaks are also present in the XRPD pattern of lopinavir/Vit E TPGS (FIG. 21). Similar differences, i.e., extra peaks and peak shifts, are also found between toluene and EtOAc Type III solvates of lopinavir, disclosed in U.S. Pat. No. 6,608,198, that are known to be both Type III crystalline form (FIG. 22).

These variations in XRPD patterns suggest slight differences in crystal lattice due to the way the solvent molecule fills the voids in the lattice channels. For the same reason, the slight differences in the XRPD patterns of the disclosed crystalline lopinavir/surfactant adducts were likely caused by surfactant molecules incorporated in the crystal lattices.

Raman spectra of the crystalline lopinavir/surfactant adducts show only the signals corresponding to lopinavir due to its high content in the samples (FIGS. 23-39). Similar Raman spectra suggest the same binding characteristic among all crystalline lopinavir/surfactant adducts. The entire list of peaks, or a subset thereof, may be sufficient to characterize each of the crystalline lopinavir/surfactant adducts, including: 3398, 3066, 3042, 2925, 2968, 1660, 1643, 1606, 1585, 1446, 1381, 1346, 1267, 1238, 1209, 1033, 1004, 958, 883, 791, 754, 697, 622, and 532 $cm^{-1} \pm 1$ $cm^{-1}$. A slight shift in the peak at 3066 $cm^{-1}$ was observed for some of the crystalline lopinavir/surfactant adducts.

The XRPD pattern and Raman spectra of crystalline lopinavir/surfactant adducts suggest that the crystalline solids are slightly different, i.e., the environment of lopinavir molecules in crystal lattices of lopinavir/surfactants may differ slightly. This difference may be explained by the fact that the surfactant molecules are located in the crystal lattices. The surfactant molecules have different sizes. Therefore, the local environment of lopinavir molecules may be changed to different extents depending on the size of the surfactant molecules.

However, there is no evidence of strong interaction between lopinavir and surfactant molecules in the crystal lattices. Therefore, it is possible that the difference is simply due to the defects in the crystal lattice. Characterization of bulk lopinavir/surfactant makes the conclusion especially difficult because the measured properties reflect a combination of that in the crystal lattice and that of crystal surface. Moreover, a significant amount of free surfactant molecules may be present in the space between the agglomerated crystal particles.

Single crystals of the crystalline lopinavir/surfactant adducts may be used to avoid confusion between surfactant molecules in the crystal lattice and those on the surface. Specifically, the surfactant molecules on the crystal surface can be washed away. Therefore, the measured properties of lopinavir/surfactant single crystals would correspond to the internal structure of the crystal.

Example 2

Single Crystals of Crystalline Lopinavir/Surfactant Adducts 2.1 Materials Used

Amorphous lopinavir, prepared in the manner discussed above, and the following pure surfactants listed in Table 2 were used in the preparation of single crystals of crystalline lopinavir/surfactant adducts.

TABLE 2

| Pure Surfactants |
|---|
| Surfactant |
| Pluronic F68 (Sigma) |
| Pluronic F127 (Sigma) |
| Hydroxy-propyl cellulose (Nippon Soda) |
| Sodium dodecyl sulfate (EMD) |
| Plasdone (ISP Technology) |
| Plasdon K29/32 (ISP Technology) |
| Tween 20 (Sigma) |
| Tween 80 (Sigma) |
| Vit E/TPGS (Eastman) |
| Cremophor EL (BASF) |
| Plurol Oleique (Gattefosse) |
| Lauroglycol 90 (Gattefosse) |
| Lauroglycol FCC (Gattefosse) |
| Capryol (Gattefosse) |
| Oleic acid (Nu-Chek) |

2.2 Preparation of Single Crystals of Crystalline Lopinavir/Surfactant Adducts Crystallization of lopinavir was conducted in the pure surfactants that are liquid at ambient temperature, i.e., Cremophor EL, Plurol Oleique, Tween 20, Tween 80, Lauroglycol 90, Lauroglycol FCC, Capryol, and Oleic acid. About 1 g of liquid surfactant was weighed into a 4 ml vial and heated to 65° C. Amorphous lopinavir was added to the heated surfactant incrementally while stirred until saturation was reached. The solution was then cooled to room temperature naturally. Single crystals were observed in Cremophor EL and Lauroglycol FCC. Single crystals were aged in solution by repeatedly heating to 50° C. and cooling to room temperature.

2.3 Structure of Single Crystal of Crystalline Lopinavir/Lauroglycol Adduct

Figure 40:
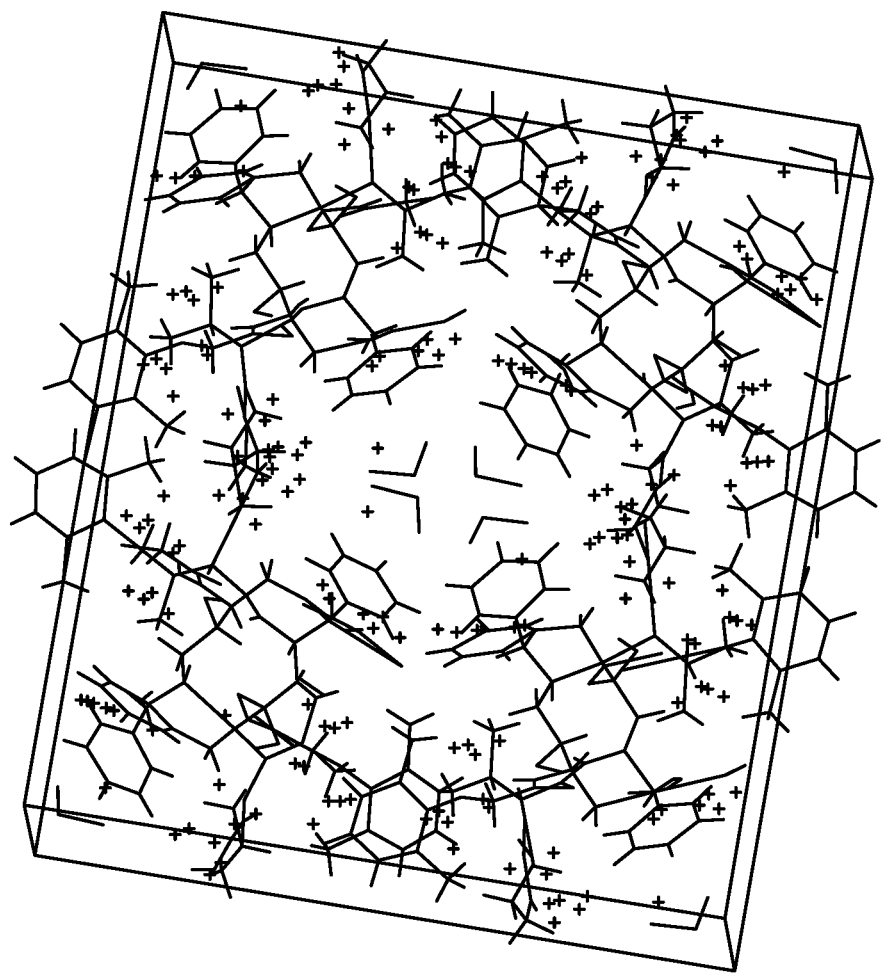
FIG. 40 shows the single crystal structure of a lopinavir/lauroglycol adduct.

The structure of the single crystal of crystalline lopinavir/lauroglycol adduct is shown in FIG. 40. The crystal has a structure like that of the other Type III lopinavir crystals. The single crystal structure does not reveal lauroglycol molecules, but shows high electron density between lopinavir molecules in the lattice. This observation suggests that the space between lopinavir molecules is not empty, but filled with some molecules. The molecules filling the space are not repeatedly allocated at a symmetric point in the lattice. The single crystal was prepared in neat lauroglycol. Therefore, the space-filling component is most likely lauroglycol.

Presence of lauroglycol in the crystal lattice does not necessarily mean the single crystal is a crystalline adduct of lopinavir with lauroglycol. Lauroglycol molecule may be trapped in the crystal defects during crystal growth. Otherwise, lauroglycol molecules should be homogeneously distributed in single crystal of lopinavir/lauroglycol.

2.4 Progressive Dissolution of Single Crystals of Crystalline Lopinavir/Lauroglycol Adduct 274.5 mg of single crystals of crystalline lopinavir/lauroglycol adduct were weighed into a 1 mL centrifuge vial. Crystals were loosely packed to the bottom of the vial in order to assure submerging of crystals in solvent. 500 µL of heptane was added to the centrifuge vial. The vial was capped and vortexed for 30 seconds. Heptane was removed immediately following vortex by centrifuging for 5 minutes. The single crystals were washed with heptane twice in order to remove the residual lauroglycol on the surface. The single crystals with a clean surface were further washed three times with 200 µL of $CDCl_3$. Each wash included a 10 second vortexing followed by centrifugation. The $CDCl_3$ solution of lopinavir/lauroglycol passed each centrifuge and was collected and diluted. The ratio between lopinavir and lauroglycol in the solutions were determined using $H^1$-NMR spectroscopy.

Figure 41:
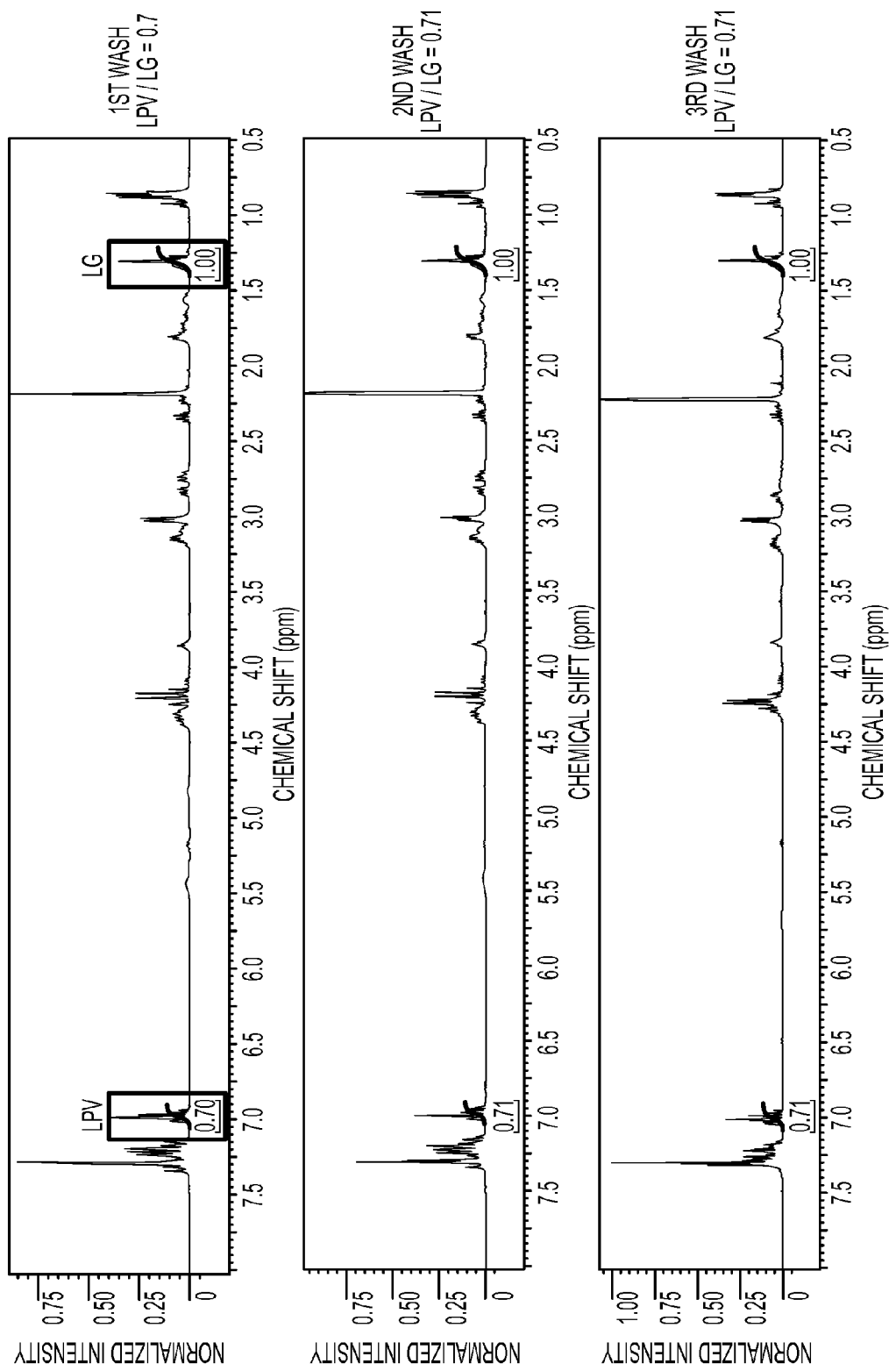
FIG. 41 shows solution $H^1$-NMR spectra of solutions collected after $1^{st}$, $2^{nd}$, and $3^{rd}$ $CDCl_3$ wash of single crystals of crystalline lopinavir/lauroglycol adduct.

Progressive dissolution was used to dissolve single crystals of lopinavir/lauroglycol layer by layer. A constant ratio between lopinavir and lauroglycol demonstrates that lopinavir and lauroglycol are homogeneously populated throughout the crystal. $H^1$-NMR spectra of the solutions collected after $1^{st}$, $2^{nd}$, and $3^{rd}$ wash of single crystals using $CDCl_3$ are shown in FIG. 41. Proton resonance at chemical shifts of 7.0 and 1.3 ppm correspond to lopinavir and lauroglycol, respectively. They are chosen to be the characteristic peaks in data analysis. The ratio of the integrated peak area remained constant (lopinavir/lauroglycol=0.71), which supports that lopinavir and lauroglycol are distributed in the crystals in a homogeneous fashion. With a calibration curve constructed on the mixtures of known amounts of lopinavir and lauroglycol, the lopinavir/lauroglycol single crystals was calculated to have about 8.65-about 10.07% (w/w) or about 18.73-about 21.38% (molar %) of lauroglycol.

The variation in composition demonstrated that lauroglycol molecules are not strongly bonded to lopinavir in the crystal lattice. Instead, lauroglycol molecules are filled in the channels in the crystal lattice. Therefore, the composition of lopinavir and lauroglycol may vary from batch to batch.

Figure 42:
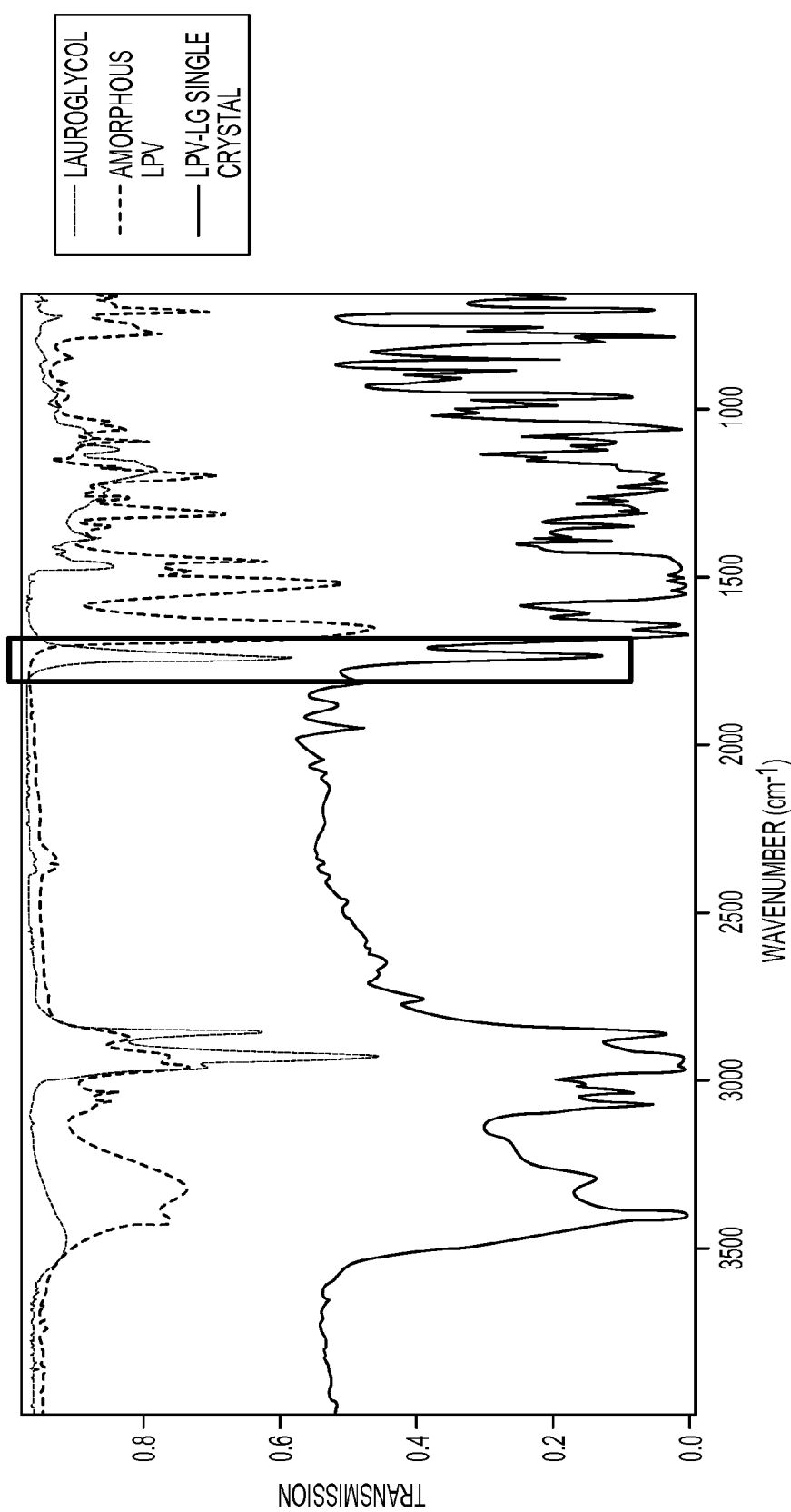
FIG. 42 shows IR spectra of liquid lauroglycol, amorphous lopinavir, and the single crystal of crystalline lopinavir/lauroglycol adduct.
Figure 43:
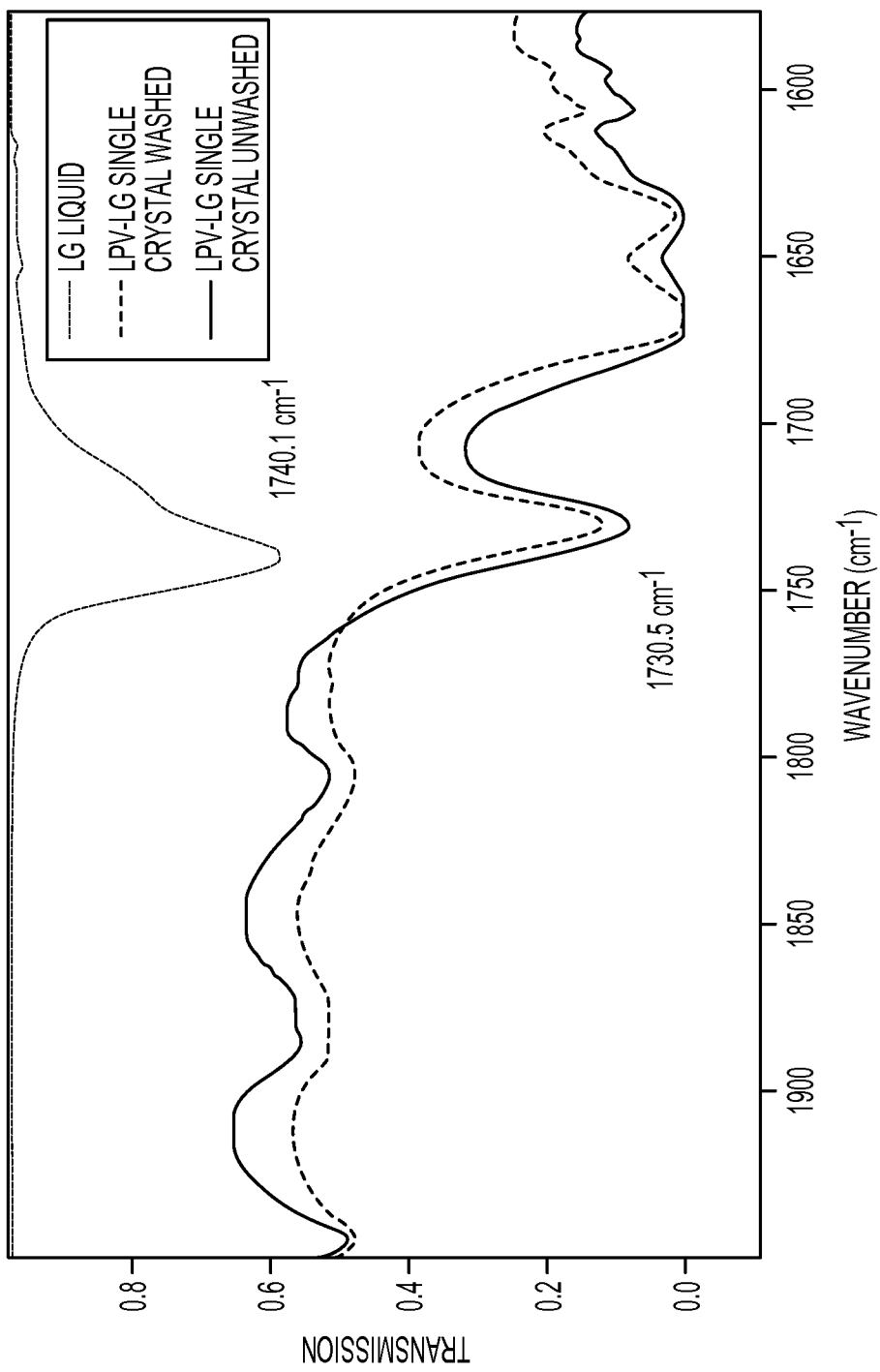
FIG. 43 shows IR spectra of liquid lauroglycol, washed single crystal of crystalline lopinavir/lauroglycol adduct, and unwashed single crystal of crystalline lopinavir/lauroglycol adduct.

2.5 Infrared Characterization of Single Crystals of Crystalline Lopinavir/Lauroglycol Adduct FIG. 42 shows the IR patterns of liquid lauroglycol, amorphous lopinavir, and single crystals of crystalline lopinavir/lauroglycol adduct. The stretching motion of carbonyl group in lauroglycol has its characteristic infrared peak at 1740 $cm^{-1}$. This peak was used to differentiate the local environment of lauroglycol molecules in neat liquid or in lopinavir/lauroglycol single crystals (FIG. 42). This characteristic peak of lauroglycol shifted to a lower frequency in single crystals of lopinavir/lauroglycol. In their neat liquid phase, lauroglycol molecules have less constrain in its vibration due to the large inter-molecular distance. The frequency of the carbonyl stretching corresponds to its intrinsic property. However, when lauroglycol molecules are incorporated in crystal lattice with lopinavir, certain constrain may be present on the molecule. Therefore, the vibration of the carbonyl group becomes weaker, which leads to a red shift of its IR frequency. The shift of infrared frequency of lauroglycol suggests different local environments of lauroglycol in its liquid phase and in the single crystal (FIG. 43). Small peak shift also suggests a weak interaction between lauroglycol and lopinavir molecules, which is consistent with the conclusion made with the XRPD pattern and single crystal structure.

Figure 11:
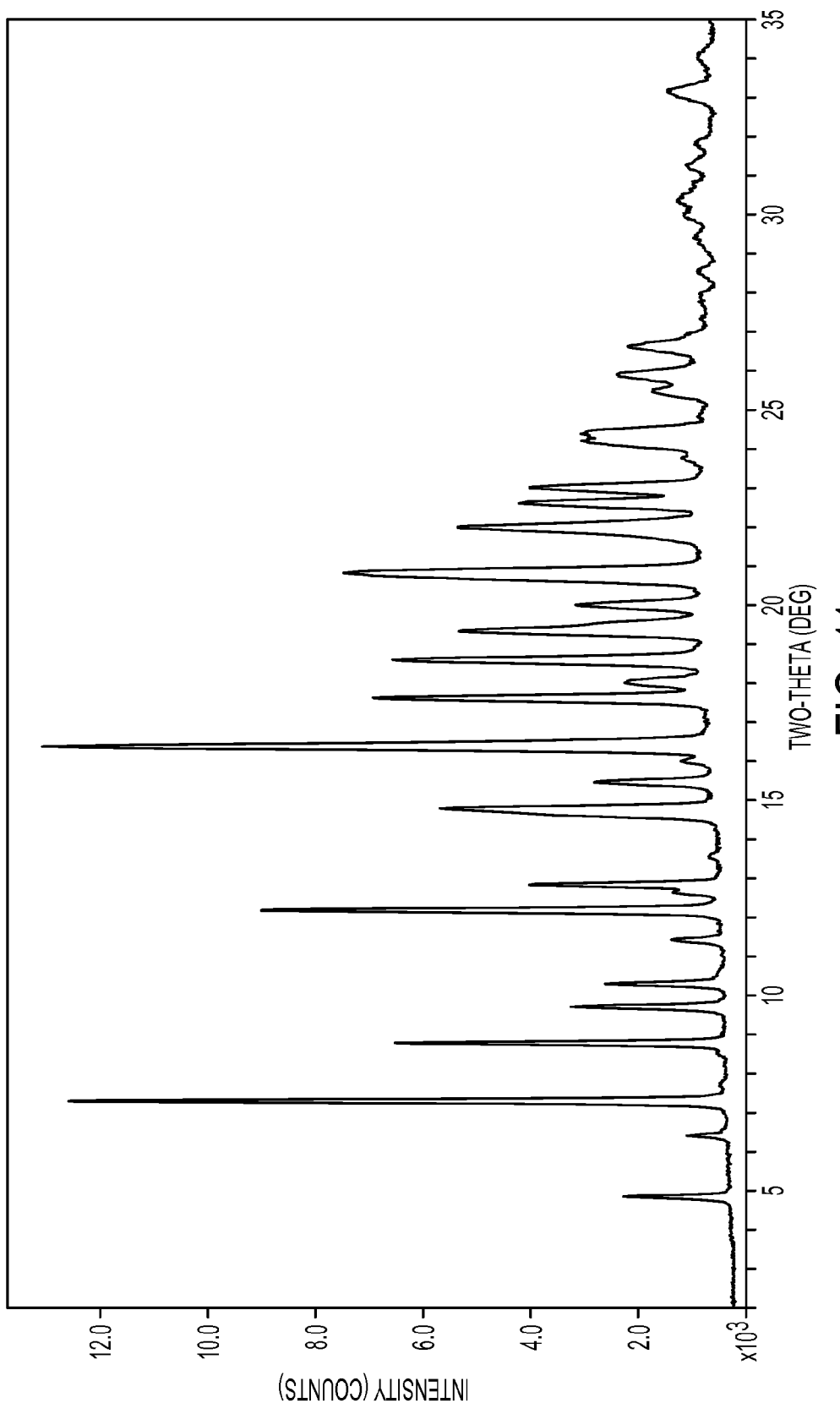
FIG. 11 shows an XRPD pattern of a crystalline adduct of lopinavir/Plurol oleique.
Figure 12:
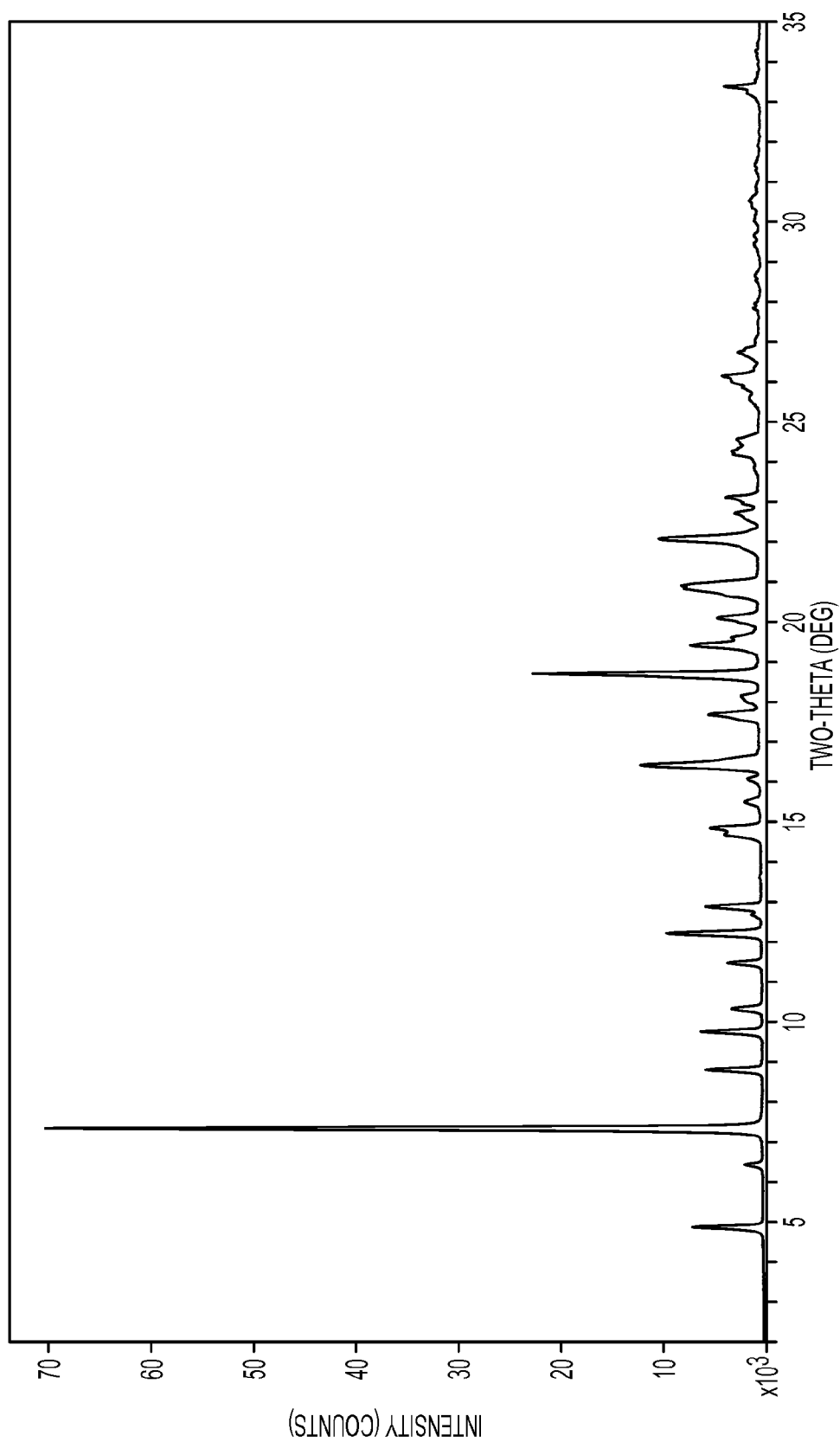
FIG. 12 shows an XRPD pattern of a crystalline adduct of lopinavir/Oleic acid.
Figure 13:
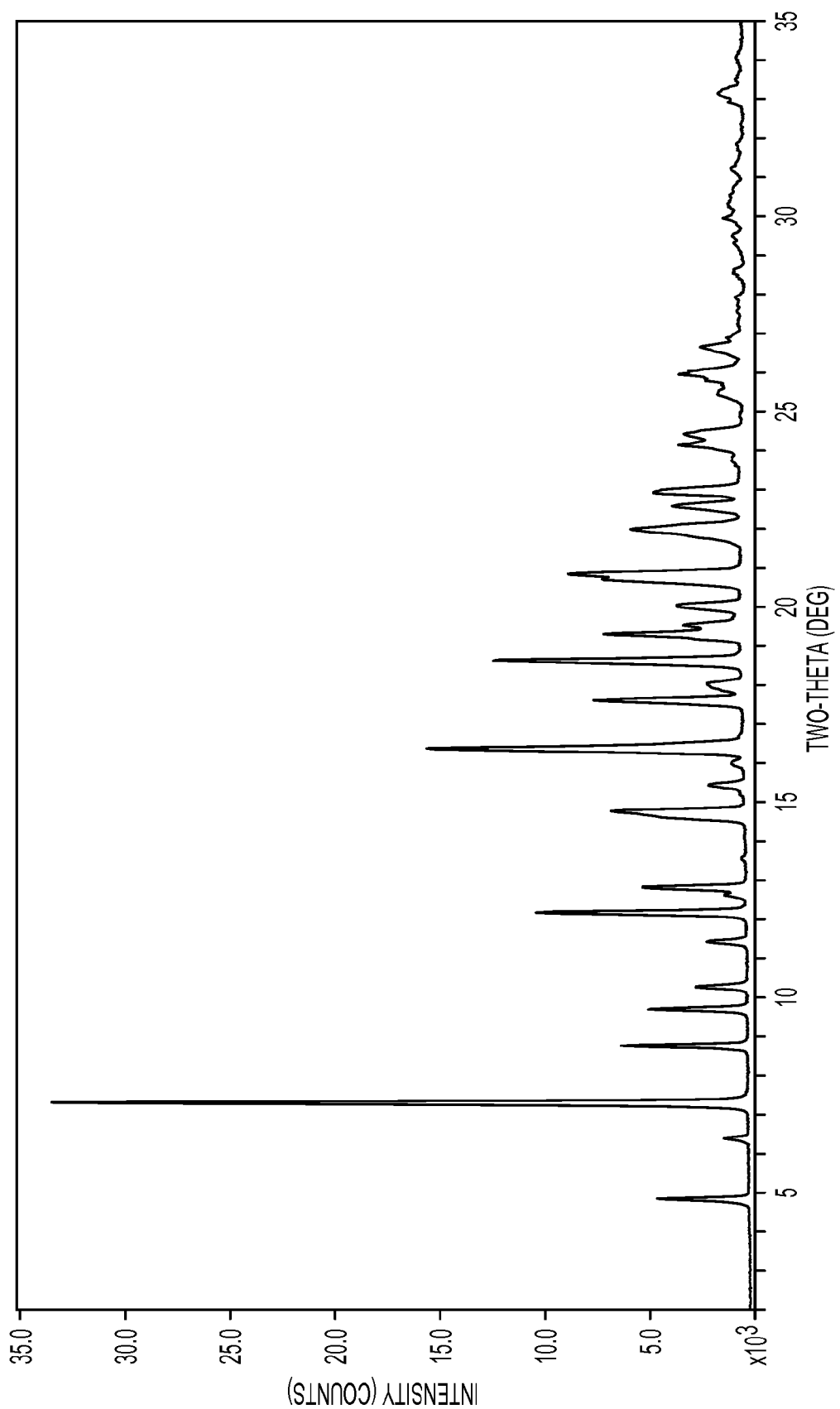
FIG. 13 shows an XRPD pattern of a crystalline adduct of lopinavir/Lauroglycol Type I.
Figure 14:
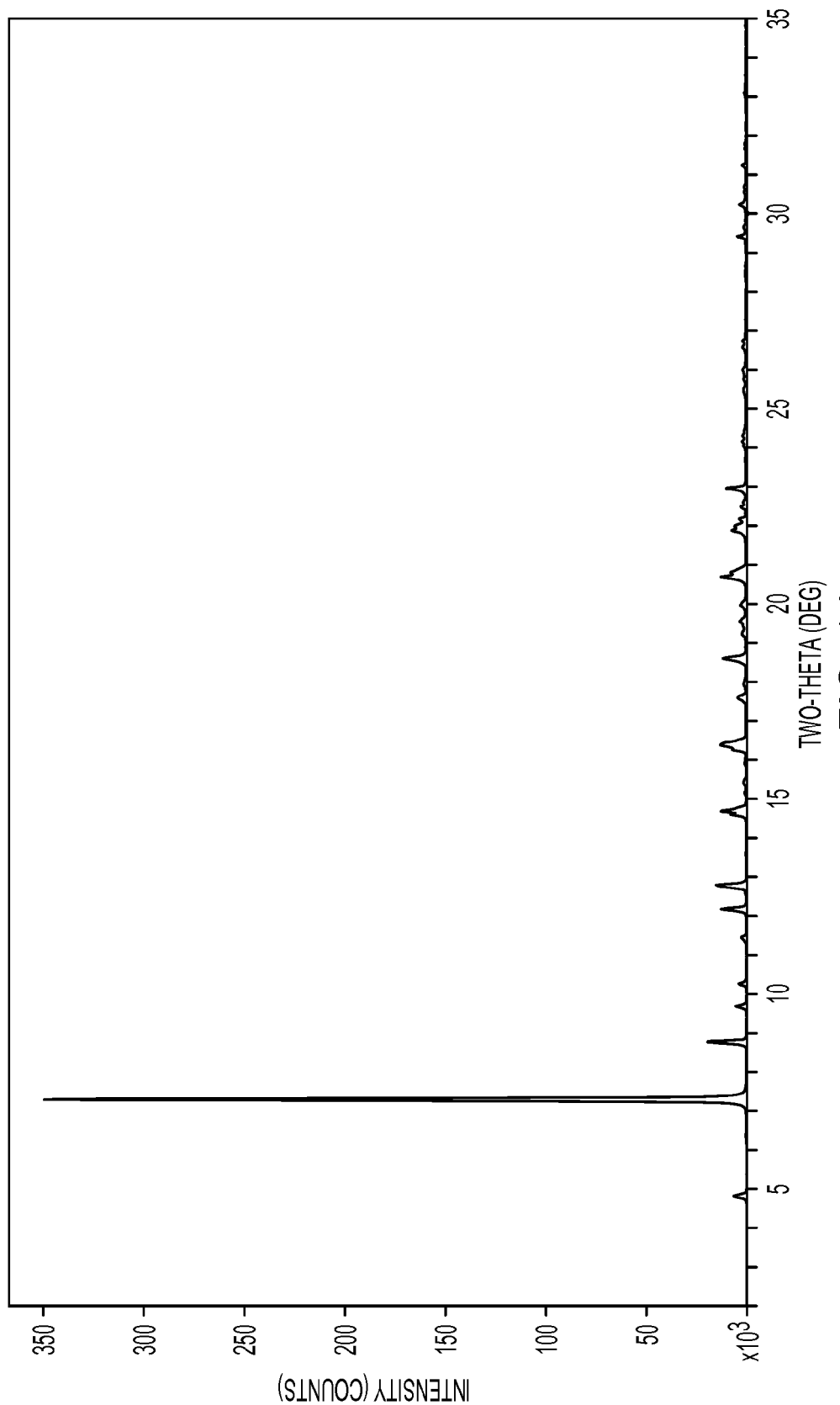
FIG. 14 shows an XRPD pattern of a crystalline adduct of lopinavir/Lauroglycol FCC.
Figure 15:
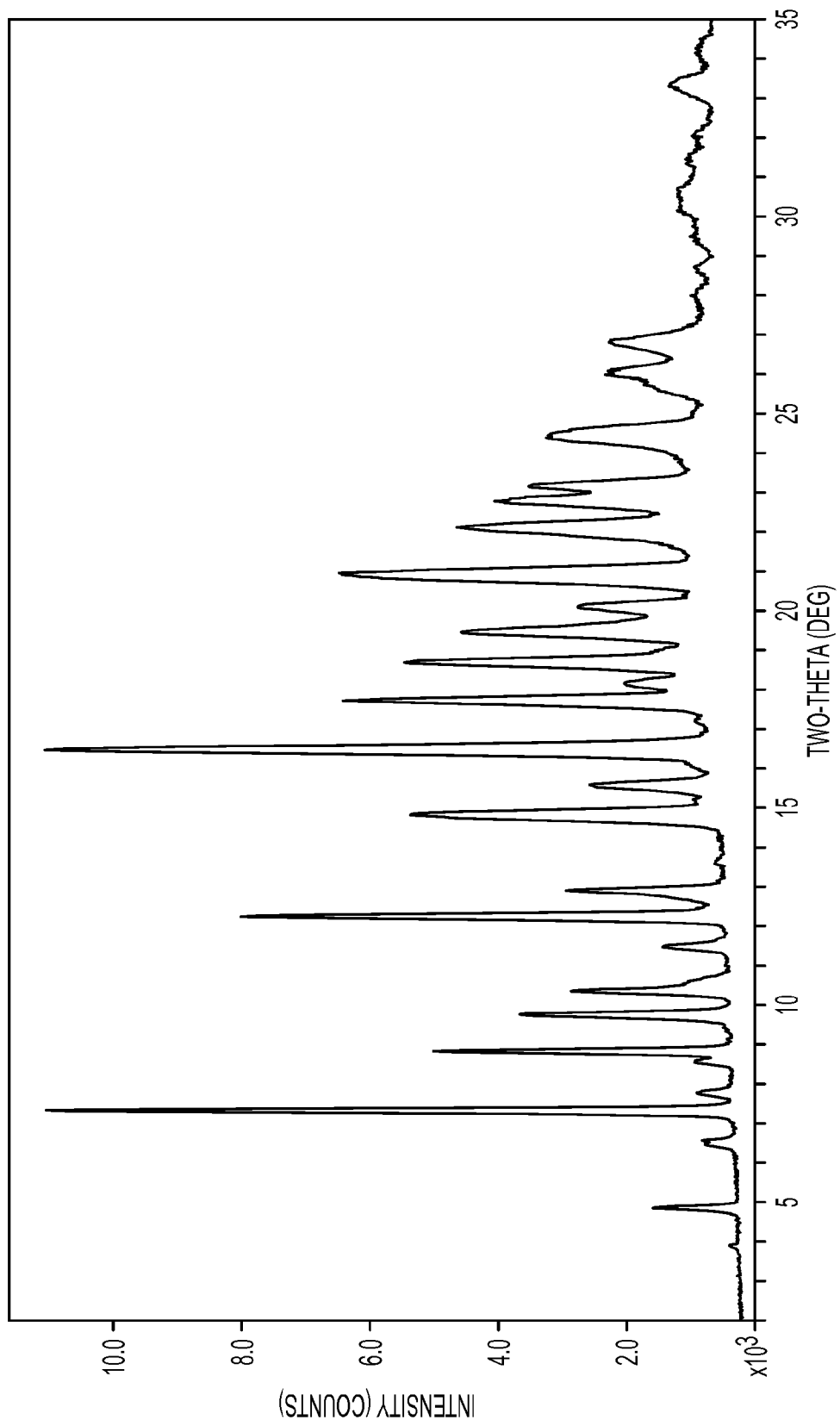
FIG. 15 shows an XRPD pattern of a crystalline adduct of lopinavir/Cremophor RH40.
Figure 16:
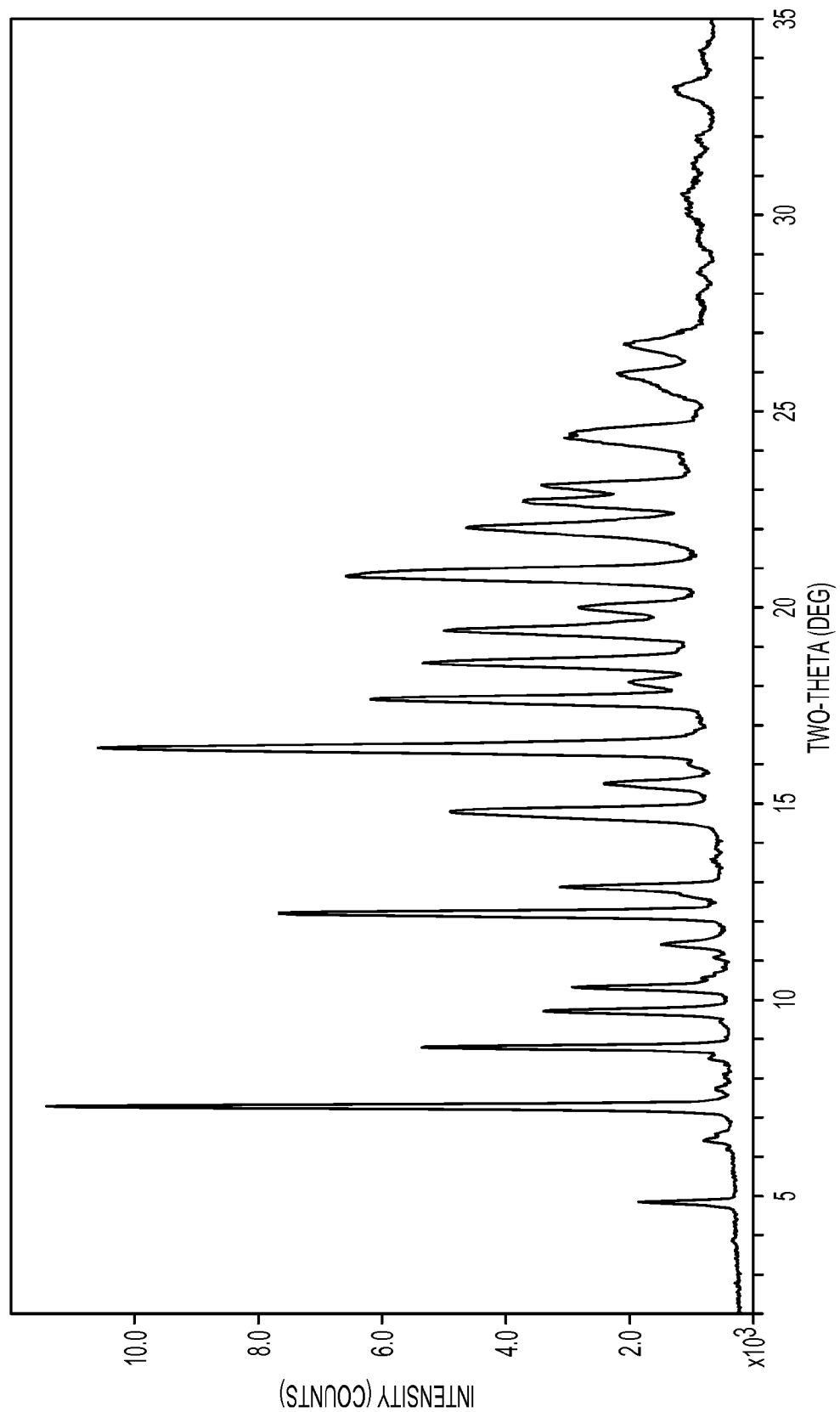
FIG. 16 shows an XRPD pattern of a crystalline adduct of lopinavir/Cremophor EL.
Figure 17:
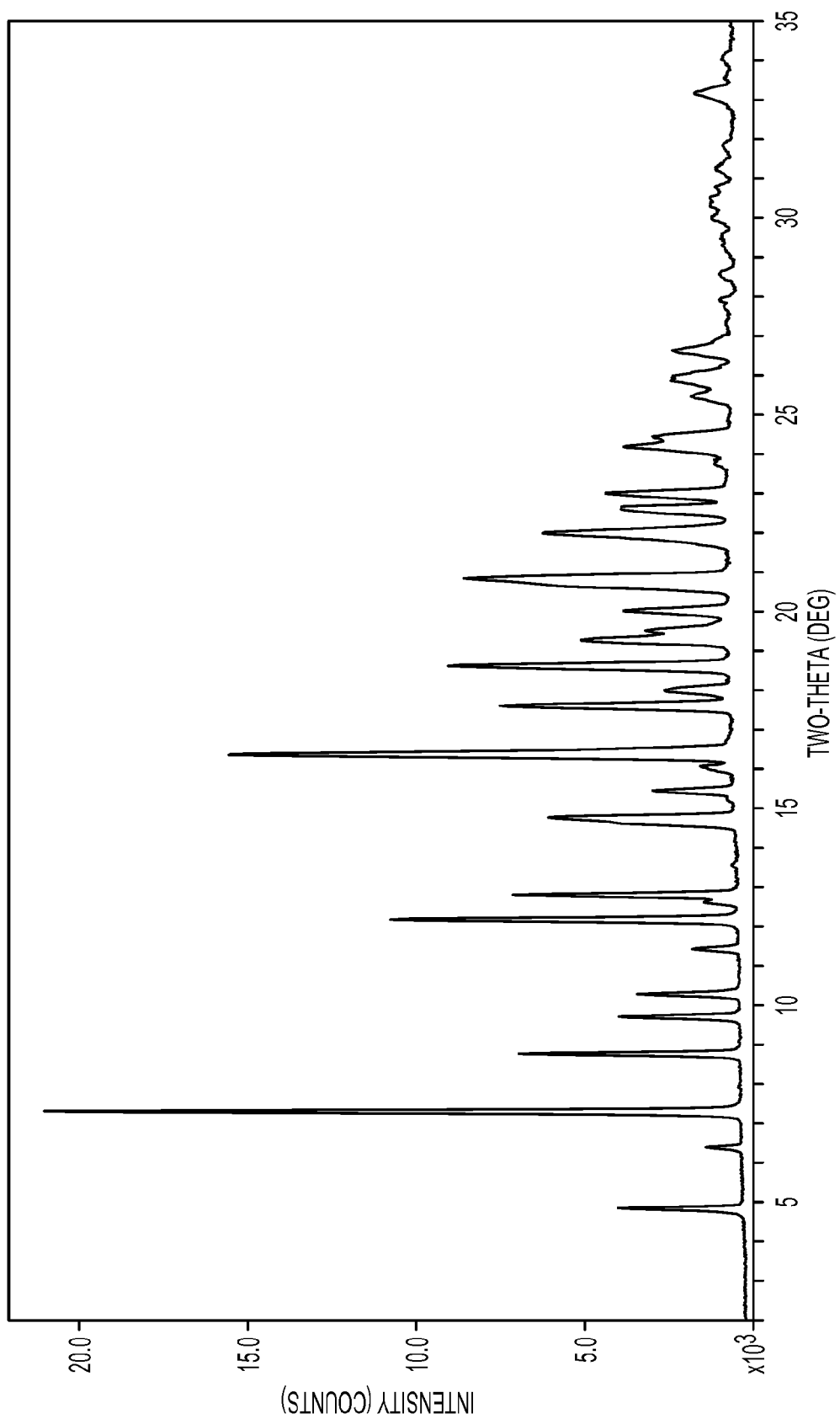
FIG. 17 shows an XRPD pattern of a crystalline adduct of lopinavir/Capryol 90.
Figure 18:
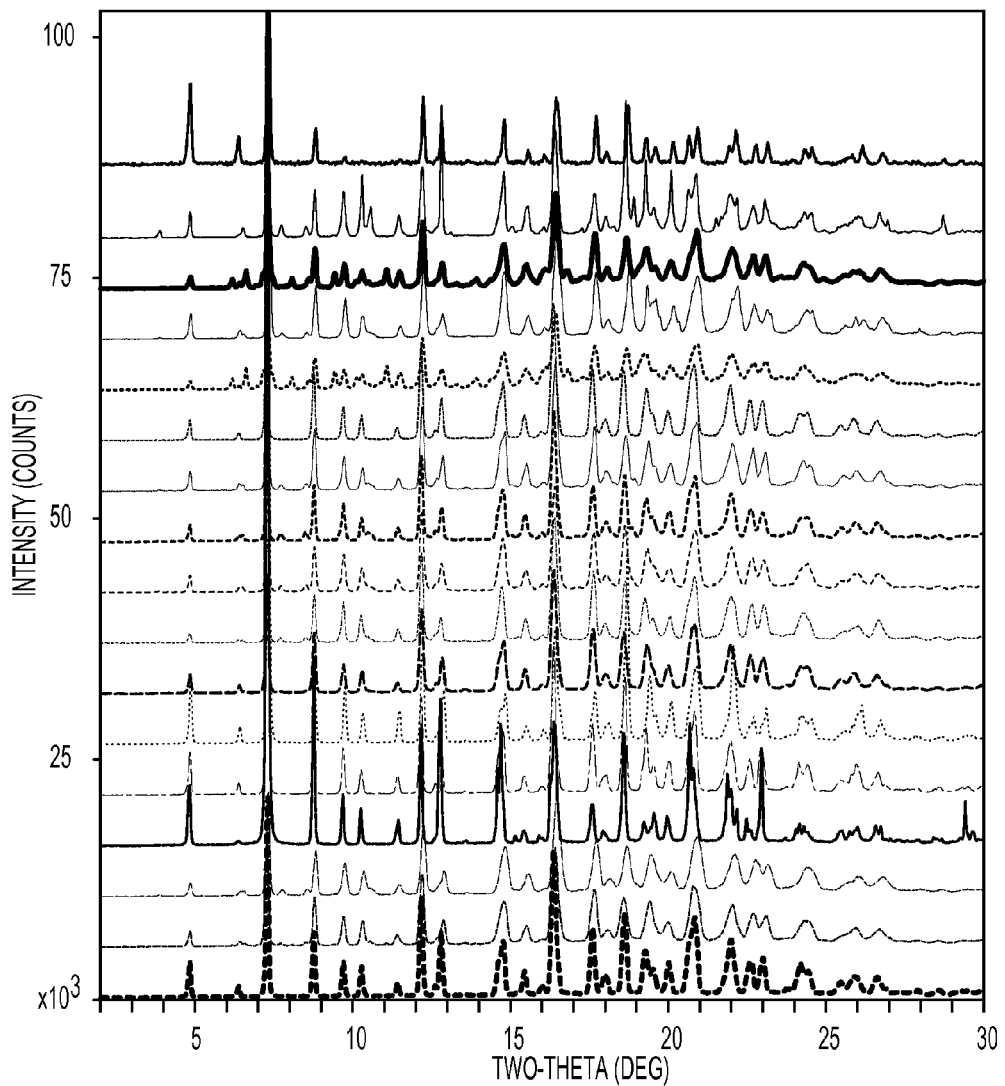
FIG. 18 shows an overlay of XRPD patterns of a Type III lopinavir crystal solvate (lopinavir/EtOAc solvate) and crystalline lopinavir/surfactant adducts of the invention, including lopinavir/VitE TPGS, lopinavir/Tween 80, lopinavir/Tween 65, lopinavir/Tween 20, lopinavir/Span 80, lopinavir/Span 40, lopinavir/Span 20, lopinavir/Solutol HS15, lopinavir/Pluronic F68, lopinavir/Plurol oleique, lopinavir/Oleic acid, lopinavir/Lauroglycol Type I, lopinavir/Lauroglycol FCC, lopinavir/Cremophor RH40, lopinavir/Cremophor EL, and lopinavir/Capryol 90.
Figure 44:
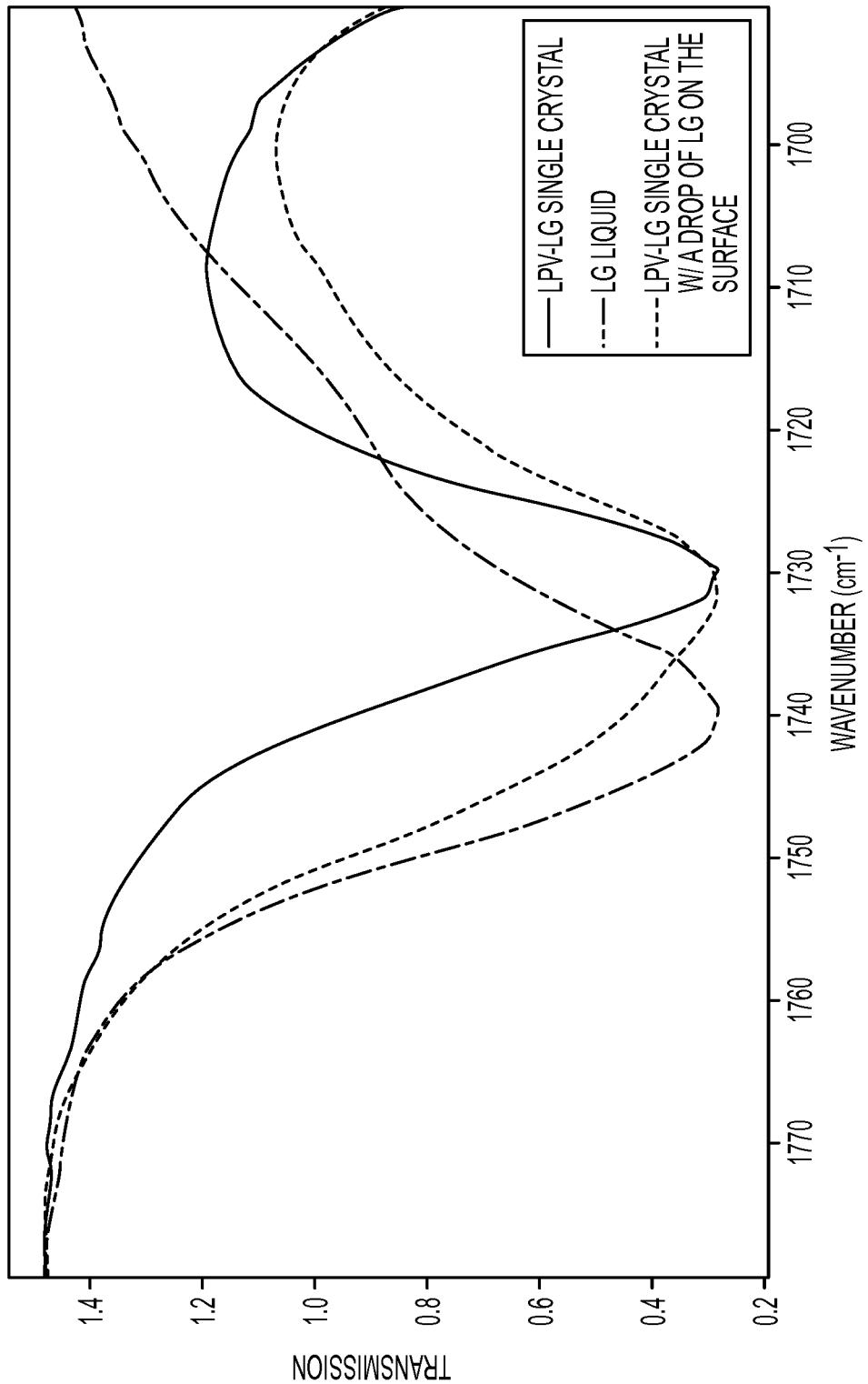
FIG. 44 shows IR spectra of liquid lauroglycol, single crystal of crystalline lopinavir/lauroglycol adduct, and single crystal of crystalline lopinavir/lauroglycol adduct with a drop of lauroglycol on the surface.

When a drop of liquid lauroglycol was added to cover the single crystal, the characteristic peak of lauroglycol was found to broaden into higher frequency (FIG. 44). This is due to overlap of carbonyl stretching of lauroglycol in both liquid phase and lopinavir/lauroglycol crystal. The peak position of lauroglycol in single crystals remains unchanged at lower frequency of 1730 $cm^{-1}$ with or without liquid lauroglycol on the surface (FIG. 11). This observation suggests that the majority of the vibrational band was due to carbonyl stretching of lauroglycol in crystal. There are a larger number of lauroglycol molecules in the single crystal than in the liquid covering the crystal along the infrared beam path. This result agrees with the conclusion that a significant amount of lauroglycol molecules are located in the crystal lattice.

The findings on lopinavir/lauroglycol single crystals may also apply to the other lopinavir/surfactant crystals due to the fact that amorphous lopinavir crystallizes into Type III crystal in neat surfactants.

2.6 Characterization of Bulk Single Crystals

Figure 45:
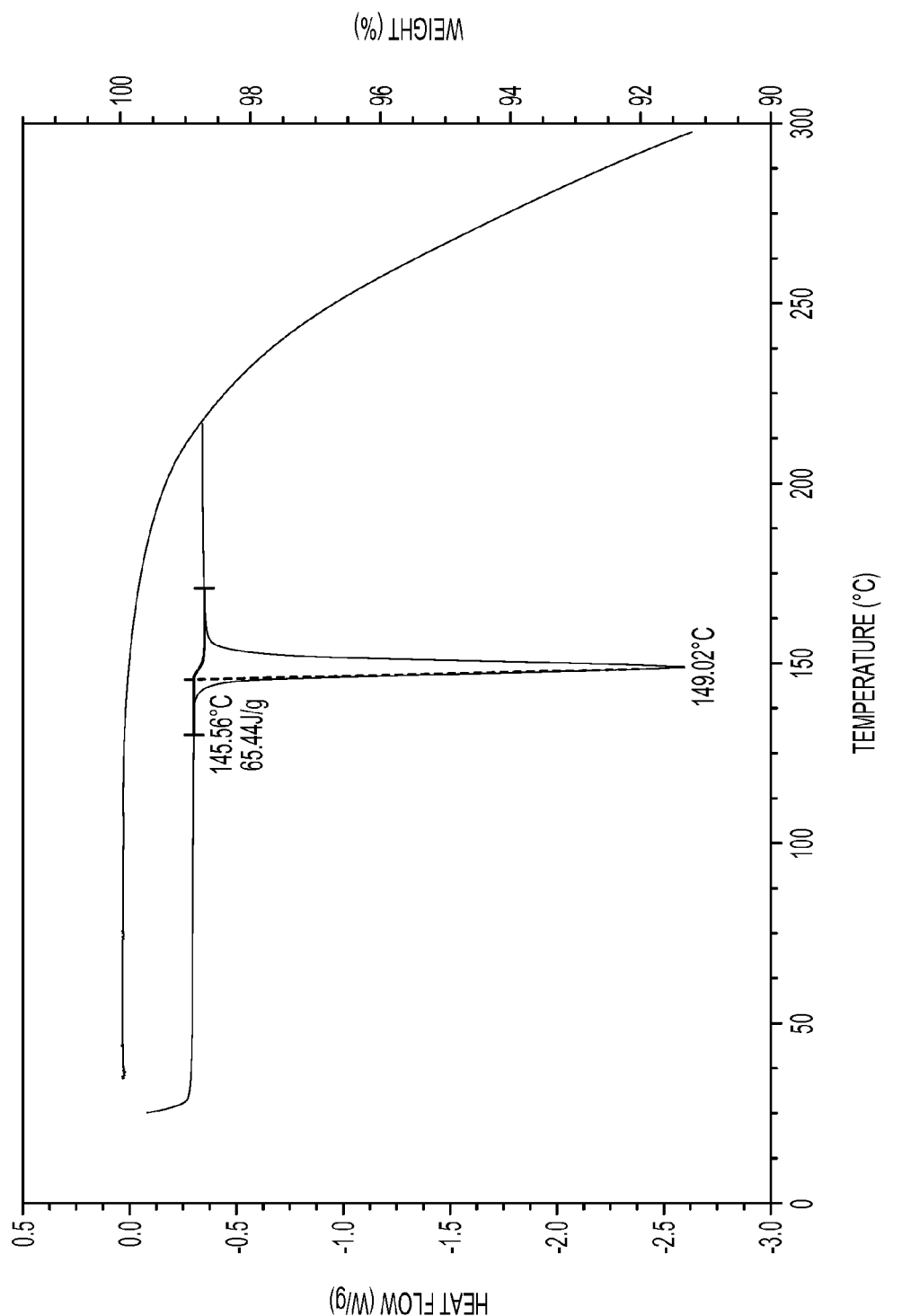
FIG. 45 shows a DSC and TGA curve of single crystals of crystalline lopinavir/lauroglycol adduct.
Figure 46:
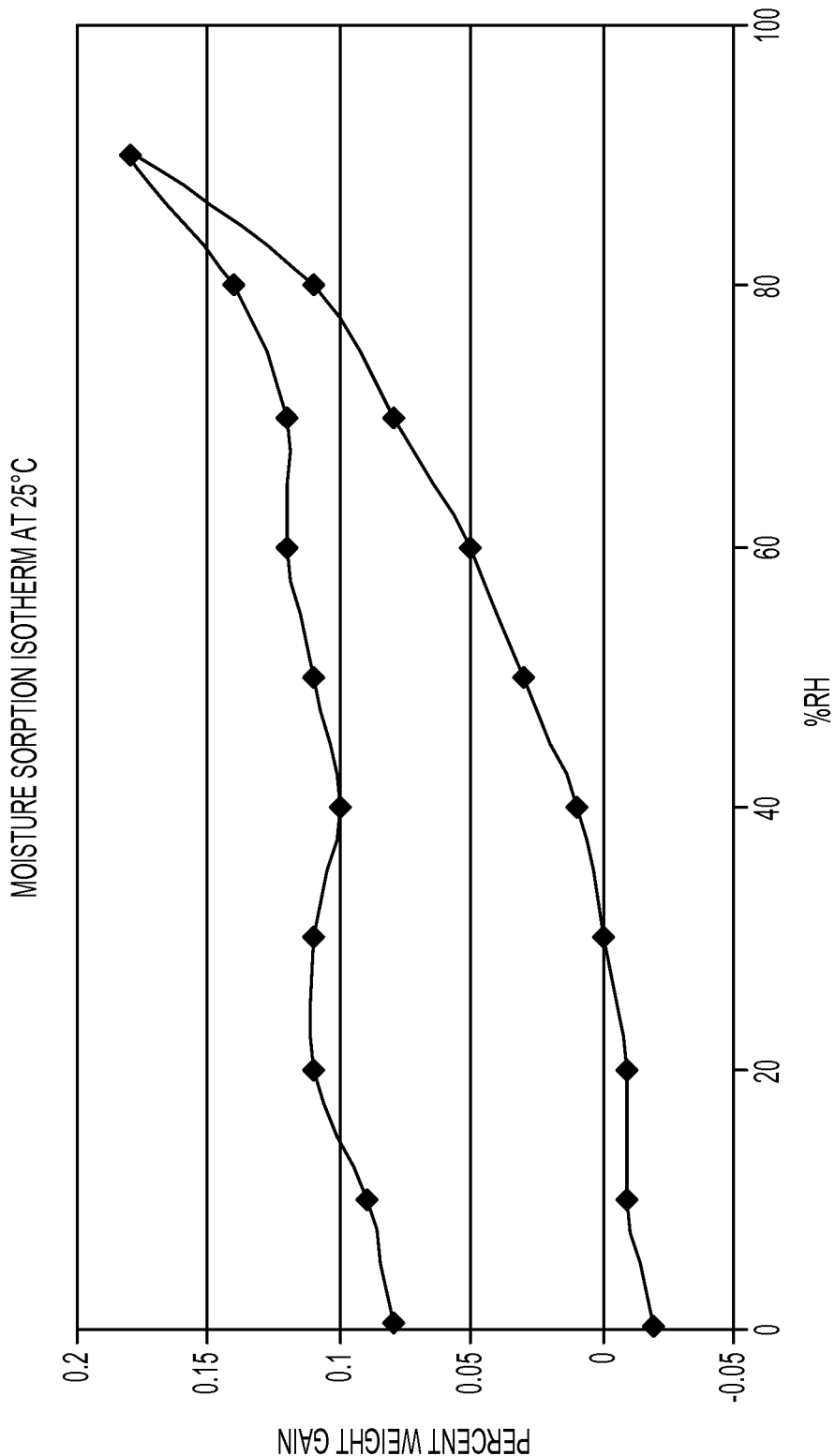
FIG. 46 shows a moisture sorption isotherm of single crystals of crystalline lopinavir/lauroglycol adduct.

Single crystals of crystalline lopinavir/lauroglycol adduct washed by heptane were used for solid state characterization. The crystals melted at 145.5° C. A weight loss following melting may be due to evaporation of lauroglycol or degradation (FIG. 45). When exposed to moisture, lopinavir/lauroglycol crystals pick up only 0.2% (w/w) water at 90% RH at 25° C. (FIG. 46). Therefore, the crystalline lopinavir/lauroglycol adduct is not hygroscopic.

This data establishes that lauroglycol is in the crystal lattice of crystalline lopinavir/lauroglycol adduct. Furthermore, lauroglycol molecules are located in the crystal lattice, but are not located at a well-defined position in the crystal lattice, as would be expected in the conventional cocrystals. There also was not a strong interaction between lopinavir and surfactant molecules.

The claimed invention is:

1. A single crystal of crystalline lopinavir/surfactant adduct characterized by an XRPD pattern having peaks at 4.8, 7.3, 8.8, 9.7, 10.3, 12.2, 12.8, 14.7, 16.4, 17.6, 18.6, 20.0, 21.9, 22.5, and 23.0°2θ±0.2°2θ.

2. A single crystal of crystalline lopinavir/surfactant adduct according to claim 1, wherein the surfactant is selected from at least one of VitE TPGS, a polysorbate, a sorbitan fatty acid ester, a polyoxyethylene ester, a poloxamer or a copolymer of ethylene oxide and propylene oxide, polyglyceryl-3 oleate, a fatty acid, a propylene glycol laurate, a polyoxyethylene hydrogenated castor oil, a polyethoxylated castor oil, and a propylene glycol monocaprylate.

3. A single crystal of crystalline lopinavir/surfactant adduct characterized by an IR spectrum having a peak at 1730 $cm^{-1}$.

4. A single crystal of crystalline lopinavir/surfactant adduct characterized by a Raman spectrum having peaks at 3398, 3066, 3042, 2925, 2968, 1660, 1643, 1606, 1585, 1446, 1381, 1346, 1267, 1238, 1209, 1033, 1004, 958, 883, 791, 754, 697, 622, and 532 $cm^{-1}$±1 $cm^{-1}$.

5. A single crystal of crystalline lopinavir/surfactant adduct according to claim 1, wherein the single crystal of crystalline lopinavir/surfactant adduct is substantially pure.

6. A pharmaceutical composition comprising an effective amount of a single crystal of crystalline lopinavir/surfactant adduct according to claim 1.

7. The pharmaceutical composition of claim 6, wherein at least 50% of lopinavir in the composition is in the form of the single crystal of crystalline lopinavir/surfactant adduct.

8. The pharmaceutical composition of claim 6, wherein at least 75% of lopinavir in the composition is in the form of the single crystal of crystalline lopinavir/surfactant adduct.

9. The pharmaceutical composition of claim 6, wherein at least 95% of lopinavir in the composition is in the form of the single crystal of crystalline lopinavir/surfactant adduct.

\* \* \* \* \*